(12) United States Patent
Sode et al.

(10) Patent No.: US 12,123,046 B2
(45) Date of Patent: Oct. 22, 2024

(54) FUSION PROTEIN OF FLAVIN ADENINE DINUCLEOTIDE-GLUCOSE DEHYDROGENASE AND CYTOCHROME MOLECULE

(71) Applicants: ULTIZYME INTERNATIONAL LTD., Tokyo (JP); I-SENS, INC., Seoul (KR)

(72) Inventors: Koji Sode, Tokyo (JP); Youngjea Kang, Seoul (KR); Kazushige Mori, Tokyo (JP); Katsuhiro Kojima, Tokyo (JP); Junko Shimazaki, Tokyo (JP)

(73) Assignees: ULTIZYME INTERNATIONAL LTD., Tokyo (JP); I-SENS, INC., Seoul (KR)

( * ) Notice: Subject to any disclaimer, the term of this patent is extended or adjusted under 35 U.S.C. 154(b) by 1049 days.

(21) Appl. No.: 16/979,161

(22) PCT Filed: Mar. 8, 2019

(86) PCT No.: PCT/JP2019/009235
§ 371 (c)(1),
(2) Date: Sep. 8, 2020

(87) PCT Pub. No.: WO2019/172400
PCT Pub. Date: Sep. 12, 2019

(65) Prior Publication Data
US 2020/0399671 A1    Dec. 24, 2020

(30) Foreign Application Priority Data

Mar. 8, 2018   (JP) .................................. 2018-042275

(51) Int. Cl.
*C12Q 1/00* (2006.01)
*C07K 14/80* (2006.01)
(Continued)

(52) U.S. Cl.
CPC .............. *C12Q 1/006* (2013.01); *C07K 14/80* (2013.01); *C12N 9/0006* (2013.01); *C12N 15/62* (2013.01);
(Continued)

(58) Field of Classification Search
CPC .. C07K 14/80; C07K 2319/00; C07K 14/245; C12N 9/0006; C12N 9/0008; C12Y 101/05; C12Y 101/01047
See application file for complete search history.

(56) References Cited

U.S. PATENT DOCUMENTS

| 6,180,366 | B1 | 1/2001 | Royer et al. |
| 6,432,672 | B1 | 8/2002 | Selten et al. |
| 2011/0045513 | A1* | 2/2011 | Takenaka ............... C07K 14/80 435/14 |

FOREIGN PATENT DOCUMENTS

| CN | 1257546 | 6/2000 |
| CN | 1309711 | 8/2001 |

(Continued)

OTHER PUBLICATIONS

Allen et al. (A Cytochrome b562 Variant with a c-Type Cytochrome CXXCH Heme-binding Motif as a Probe of the *Escherichia coli* Cytochrome c Maturation System, vol. 278, No. 52, Issue of Dec. 26, 2003, pp. 52075-52083) (Year: 2003).*

(Continued)

*Primary Examiner* — Louise W Humphrey
*Assistant Examiner* — Alexander M Duryee
(74) *Attorney, Agent, or Firm* — Ladas & Parry, LLP

(57) ABSTRACT

The purpose of the present invention is to provide a fungus-derived FADGH that has a direct electron transfer ability. Provided is a fusion protein comprising a fungus-derived (Continued)

BFU/b562:

MTDSTLNYDYIIVGAGTSGLVIANRLSELNVTVAVIEAGDSGYNNPNVTNPSGYGSA
FGTDIDWAYQSINQKYAGNKTQTLRAGKVIGGTSTINGMAYTRAEDVQIDAWEAIGN
DGWNWANLFPYYKKSQTLEIPTTTQAEAGATYDASCNGFDGPLKVGWLNSLRDPN
NFHTTLRDTYAALGVPSNDDVNCGKMVGYSRYPATYDSALNVRHDAGRAYYYPIAN
RTNLHLYPNTLAQRITWKSNTDTPTANGIEVLPNDSSTPYTIYANSEVILSAGALASP
LLLELSGIGNPSILNEHKISVVVDLPTVGENLQDQTNTGLAYNSSGKTSFSGAGTLVA
YPSAAQVFGSEVQNISAHVLQSLPSYAEQVSAASGNITKATDLLEFFKVQHDLIFSTT
HPVPMAEILIIPSATSFSSEYWALLPFARGSIHITSSVAGEPAAINPNYYMFDWDITSQ
ISTAKFIRSVFETSPFSSFVGSETKPGLNTVPANATEAEWFEWVKTAYRSNFHPVGT
AAMMPREVGGVVDSKLKVYGTANVRVVDASILPMQVCGHLVSTLYAVAERAADLIK
EDIVAGKARMPEFVAQRTGQLLQGVKYADLEDNMETLNDNLKVIEKADNAAQVKD
ALTKMRAAALDAQKATPPKLEDKSPDSPEMKDFRHGFDILVGQIDDALKLANEGKV
KEAQAAAEQLKTTRNAYHQKYR (SEQ ID NO: 1)

FADGDH or a mutant thereof and a cytochrome molecule connected to the N-terminus of the FADGDH or variant thereof.

12 Claims, 18 Drawing Sheets

Specification includes a Sequence Listing.

(51) Int. Cl.
*C12N 9/04* (2006.01)
*C12N 15/62* (2006.01)
*C12Q 1/32* (2006.01)
(52) U.S. Cl.
CPC ............ *C12Q 1/32* (2013.01); *C07K 2319/00* (2013.01); *C12Y 101/05* (2013.01)

(56) References Cited

FOREIGN PATENT DOCUMENTS

| | | |
|---|---|---|
| CN | 102414319 | 4/2012 |
| EP | 1 078 081 | 2/2001 |
| EP | 2 192 402 | 6/2010 |
| EP | 2 298 913 | 3/2011 |
| EP | 2 426 200 | 3/2012 |
| EP | 2 589 655 | 5/2013 |
| EP | 2 589 659 | 5/2013 |
| JP | 8-275780 | 10/1996 |
| JP | 2001-518798 | 10/2001 |
| JP | 2002-515253 | 5/2002 |
| JP | 2012-210212 | 11/2012 |
| JP | 5303084 | 6/2013 |
| JP | 2014-207911 | 11/2014 |
| KR | 10-2012-0023038 | 3/2012 |
| WO | 98/46772 | 10/1998 |
| WO | 99/60137 | 11/1999 |
| WO | 2010/126139 | 11/2010 |
| WO | 2009/037838 | 1/2011 |
| WO | 2017/094776 | 6/2017 |

OTHER PUBLICATIONS

Office Action dated on Nov. 30, 2021 for Korean Patent Application No. 10-2020-7025929.

International Preliminary Report on Patentability (Chapter I) for PCT/JP2019/009235 issued on Sep. 8, 2020 and its English translation from WIPO (now published as WO2019/172400).

Examination Report dated on Oct. 22, 2021 for Australian Patent Application No. 2019230713.

Examination Report No. 2 dated on Aug. 24, 2022 for Australian Patent Application No. 2019230713.

Hiromi Yoshida et al.: "Structural analysis of fungus-derived FAD glucose dehydrogenase", Nature Scientific Reports, 2015, vol. 5, No. 1, pp. 1-13.

Koji Sode et al.: "Novel fungal FAD glucose dehydrogenase derived from Aspergillus niger for glucose enzyme sensor strips", Biosensors and Bioelectronics, 2017, vol. 87, pp. 305-311.

Extended European Search Report dated on Dec. 3, 2021 for European Patent Application No. 19763648.3.

Algovitay et al, "Highly Efficient Flavin-Adenine Dinucleotide Glucose Dehydrogenase Fused to a Minimal Cytochrome C Domain", Journal of the American Chemical Society, vol. 139, No. 48, doi:10.1021/jacs.7b07011, ISSN 0002-7863, Dec. 6, 2017, pp. 17217-17220, URL: https://pubs.acs.org/doi/pdf/10.1021/jacs.7b07011, XP055853359 [I] 1-12 * abstract * * p. 17218; figure 1 * DOI: http://dx.doi.org/10.1021/jacs.7b07011.

Ito Kohei et al, "Designer fungus FAD glucose dehydrogenase capable of direct electron transfer", Biosensors and Bioelectronics, Elsevier Science Ltd, UK, Amsterdam, NL, Jul. 26, 2018, vol. 123, doi:10.1016/J.BIOS.2018.07.027, ISSN 0956-5663, pp. 114-123, XP085514329 [XP] 1-12 * the whole document * DOI: http://dx.doi.org/10.1016/j.bios.2018.07.027.

Kishida et al, "Comparison of Direct and Mediated Electron Transfer in Electrodes with Novel Fungal Flavin Adenine Dinucleotide Glucose Dehydrogenase", Anal. Sci., Jul. 1, 2018, vol. 34, No. 7, doi:10.2116/analsci.17P613, pp. 783-787, XP055653326 [XP] 1-12 * the whole document * DOI: http://dx.doi.org/10.2116/analsci.17P613.

International Search Report for PCT/JP2019/009235 mailed on Jun. 11, 2019 and its English translation from WIPO (now published as WO 2019/172400).

Written Opinion of the International Searching Authority for PCT/JP2019/009235 mailed on Jun. 11, 2019 and its English translation from WIPO (now published as WO 2019/172400).

J. Am. Chem. Soc., Algov et al. "Highly efficient flavin-adenine dinucleotide glucose dehydrogenase fused to a minimal cytochrome c domain", Sep. 15, 2017, pp. 1-5.

* cited by examiner

FIG. 1

BFU/b562:

MTDSTLNYDYIVGAGTSGLVIANRLSELNVTVAVIEAGDSGYNNPNVTNPSGYGSA
FGTDIDWAYQSINQKYAGNKTQTLRAGKVIGGTSTINGMAYTRAEDVQIDAWEAIGN
DGWNWANLFPYYKKSQTLEIPTTQAEAGATYDASCNGFDGPLKVGWLNSLRDPN
NFHTTLRDTIYAALGVPSNDDVNCGKMVGYSRYPATYDSALNVRHDAGRAYYYPIAN
RTNLHLYPNTLAQRITFWKSNTDTPTANGIEVLPNDSSTPYTIYANSEVILSAGALASP
LLLELSGIGNPSILNEHKISVVVDLPTVGENLQDQTNTGLAYNSSGKTSFSGAGTLVA
YPSAAQVFGSEVQNISAHVLQSLPSYAEQVSAASGNITKATDLLEFFKVQHDLIFSTT
HPVPMAEILIPSATSFSSEYWALLPFARGSIHITSSVAGEPAAINPNYYMFDWDITSQ
ISTAKFIRSVFETSPFSSFVGSETKPGLNTVPANATEAEWFEWVKTAYRSNFHPVGT
AAMMPREVGGVVDSKLKVYGTANVRVVDASILPMQVCGHLVSTLYAVAERAADLIK
EDI\[VAGKARMPEFVAQRTGQLLQGVKY\]ADLEDNMETLNDNLKVIEKADNAAQVKD
ALTKMRAAALDAQKATPPKLEDKSPDSPEMKDFRHGFDILVGQIDDALKLANEGKV
KEAQAAAEQLKTTRNAYHQKYR (SEQ ID NO: 1)

FIG. 2A b562/BFU:

MADLEDNMETLNDNLKVIEKADNAAQVKDALTKMRAAALDAQKATPPKLEDKS

PDSPEMKDFRHGFDILVGQIDDALKLANEGKVKEAQAAAEQLKTRNAYHQKYR

NGDSGNPTTTSTKPTSTSSSVTTGPTVSATPDYIIVGAGTSGLVIANRLSELNVTV

AVIEAGDSGYNNPNVTNPSGYGSAFGTDIDWAYQSINQKYAGNKTQTLRAGKVIG

GTSTNGMAYTRAEDVQIDAWEAIGNDGWNWANLFPYYKKSQTLEIPTTQAEA

GATYDASCNGFDGPLKVGWLNSLRDPNNFHTTLRDTYAALGVPSNDDVNCGKM

VGYSRYPATYDSALNVRHDAGRAYYYPIANRTNLHLYPNTLAQRITWKSNTDTPT

ANGIEVLPNDSSTPYTYANSEVILSAGALASPLLLELSGIGNPSILNEHKISVVVD

LPTVGENLQDQTNTGLAYNSSGKTSFSGAGTLVAYPSAAQVFGSEVQNISAHVLQ

SLPSYAEQVSAASGNITKATDLLEFFKVQHDLIFSTTHPVPMAEILIIPSATSFSSEY

WALLPFARGSIHITSSVAGEPAAINPNYYMFDWDITSQISTAKFIRSVFETSPFSSF

VGSETKPGLNTVPANATEAEWFEWVKTAYRSNFHPVGTAAMMPREVGGVVDSK

LKVYGTANVRVVDASILPMQVCGHLVSTLYAVAERAADLIKEDI (SEQ ID NO: 2)

FIG. 2B b562/BFU Wild-type:

MADLEDNMETLNDNLKVIEKADNAAQVKDALTKMRAAALDAQKATPPKLEDKS
PDSPEMKDFRHGFDILVGQIDDALKLANEGKVKEAQAAAEQLKTRNAYHQKYR
NGDSGNPTTSTKPTSTSSSVTTGPTVSATPDYIIVGAGTSGLVIANRLSELNVTV
AVIEAGDSGYNNPNVTNPSGYGSAFGTDIDWAYQSINQKYAGNKTQTLRAGKVIG
GTSTNGMAYTRAEDVQIDAWEAIGNDGWNWANLFPYYKSQTLEIPTTQAEAG
ATYDASANGFDGPLKVGWLNSLEDTNNFHTTLNDTYAALGVPSNDDVNTGKMV
GYSRYPATYDSALNVRHDAGRAYYYPLANRTNLHLYPNTLAQRITWKSNTDTPTAN
GIEVLPNDSSTPYTIYANSEVILSAGALASPLLLELSGIGNPSILNEHNISVVVDLPT
VGENLQDQTNTGLAYNSSGNTSFSGAGTLVAYPSAAQVFGSEVQNISAHVLQSLPS
YAEQVSAASGNITKATDLLEFFKVQHDLIFSTTHPVPMAEILIPSATSFSSEYWALL
PFARGSIHITSSVAGEPAAINPNYYMFDWDITSQISTAKFIRSVFETSPFSSFVGSET
KPGLNTVSANATEAEWFDWVKTAYRSNFHPVSTAAMMPREVGGVVDSKLKVYGT
ANVRVVDASILPMQVSGHLVSTLYAVAERAADLIKEDI (SEQ ID NO: 13)

FIG. 6A

PcCDH heme—AfGDH:

QSASQFTDPTTGFQFTGITDPVHDVTYGFVFPPLATSGAQSTEFIGEVVAPIASKWIGIALGG

AMNNDLLIVAWANGNQIVSSTRWATGYVQPTAYTGTATLTTLPETTINSTHWKWVFRCQGC

TEWNNGGGIDVTSQGVLAWAFSNVAVDDPSDPQSTFSEHTDFGFFGIDYSTDSANYQNYLN

GDSGNPTTSTKPTSTSSSVTTGPTVSKL KNTTTYDYIVGGGTSGLVVANRLSENPDVSVL

LLEAGASVFNNPDVTNANGYGLAFGSAIDWQYQSINQSYAGGKQQVLRAGKALGGTSTIN

GMAYTRAEDVQIDVWQKLGNEGWTWKDLLPYYLKSENLTAPTSSQVAAGAAYNPAVNGKE

GPLKVGWSGSLASGNLSVALNRTFQAAGVPWVEDVNGGKMRGFNIYPSTLDVDLNVREDA

ARAYYFPYDDRKNLHLLENTTANRLFWKNGSAEEAIADGVEITSADGKVTRVHAKKEVIIS

AGALRSPLILELSGVGNPTILKKNNITPRVDLPTVGENLQDQFNNGMAGEGYGVLAGASTV

TYPSISDVFGNETDSIVASLRSQLSDYAAATVKVSNGHMKQEDLERLYQLQFDLIVKDKVPI

AEILFHPGGGNAVSSEFWGLLPFARGNIHISSNDPTAPAAINPNYFMFEWDGKSQAGIAKYI

RKILRSAPLNKLIAKETKPGLSEIPATAADEKWVEWLKANYRSNFHPVGTAAMMPRSIGGV

VDNRLRVYGTSNVRVVDASVLPFQVCGHLVSTLYAVAERASDLIKEDAKSA (SEQ ID NO: 3)

FIG. 6B

PcCDH_heme—AfGDH Glu346Lys:

QSASQFTDPTTGFQFTGITDPVHDVTYGFVFPPLATSGAQSTEFIGEVVAPLASKWIGIALGGAMNNDLLLYAWANGNQIVSSTRWATGYVQP
TAYTGTATLTTLPETTINSTHWKWVFRCQGCTEWNNGGIDVTSQGVLAWAFSNVAVDDPSDPQSTFSEHTDFGFFGIDYSTDSANYQNYL
N[GDSGNPTTTSTKPTSTSSSVTTGPTVSK]KNTTTYDYIVGGGTSGLVANRLSENPDVSVLLLEAGASVFNNPDVTNANGYGLAFGSAID
WQYQSINQSYAGGKQQVLRAGKALGGTSTINGMAYTRAEDVQIDVWQKLGNEGWTWKDLLPYYLKSENLTAPTSSQVAAGAAYNPAVNGK
EGPLKVGWSGSLASGNLSVALNRFFQAAGVPWVEDVNGGKMRGFNIYPSTLDVIDLNVREDAARAYYFPYDDRKNLHLLENTTANRLFWK
NGSAEEAIADGVEITSADGKVTRVHAKKEVIISAGALRSPLILELSGVGNPTILKKNNITPRVDLPTVGENLQDQFNNGMAGKGYGVLAGAS
TVTYPSISDVFGNETDSIVASLRSQLSDYAAATVKVSNGHMKQEDLERLYQLQFDLLVKDKVPLAEILFHPGGGNAVSSEFWGLLPFARGNIH
ISSNDPTAPAAINPNYFMFEWDCKSQAGIAKYIRKILRSAPLNKLIAKETKPGLSEIPATAADEKWVEWLKANYRSNFHPVGTAAMMPRSIGG
GVVDNRLRVYGTSNVRVVDASVLPFQVCGHLVSTLYAVAERASDLIKEDAKSA (SEQ ID NO: 14)

PcCDH_heme—AfGDH Glu346Arg:

QSASQFTDPTTGFQFTGITDPVHDVTYGFVFPPLATSGAQSTEFIGEVVAPLASKWIGIALGGAMNNDLLLYAWANGNQIVSSTRWATGYVQP
TAYTGTATLTTLPETTINSTHWKWVFRCQGCTEWNNGGIDVTSQGVLAWAFSNVAVDDPSDPQSTFSEHTDFGFFGIDYSTDSANYQNYL
N[GDSGNPTTTSTKPTSTSSSVTTGPTVSK]KNTTTYDYIVGGGTSGLVANRLSENPDVSVLLLEAGASVFNNPDVTNANGYGLAFGSAID
WQYQSINQSYAGGKQQVLRAGKALGGTSTINGMAYTRAEDVQIDVWQKLGNEGWTWKDLLPYYLKSENLTAPTSSQVAAGAAYNPAVNGK
EGPLKVGWSGSLASGNLSVALNRFFQAAGVPWVEDVNGGKMRGFNIYPSTLDVIDLNVREDAARAYYFPYDDRKNLHLLENTTANRLFWK
NGSAEEAIADGVEITSADGKVTRVHAKKEVIISAGALRSPLILELSGVGNPTILKKNNITPRVDLPTVGENLQDQFNNGMAGRGYGVLAGAS
TVTYPSISDVFGNETDSIVASLRSQLSDYAAATVKVSNGHMKQEDLERLYQLQFDLLVKDKVPLAEILFHPGGGNAVSSEFWGLLPFARGNIH
SSNDPTAPAAINPNYFMFEWDCKSQAGIAKYIRKILRSAPLNKLIAKETKPGLSEIPATAADEKWVEWLKANYRSNFHPVGTAAMMPRSIGG
VVDNRLRVYGTSNVRVVDASVLPFQVCGHLVSTLYAVAERASDLIKEDAKSA (SEQ ID NO: 15)

FIG. 6C

PcCDH heme—AfGDH Asn430Lys:

QSASQFTDPTTGFQFTGITDPVHDVTYGFVFPPLATSGAQSTEFIGEVVAPIASKWIGIALGGAMNNDLLYAWANGNQIVSSTRWATGYVQP
TAYTGTATLTTLPETTINSTHWIKWVFRCQGCTEWNNGGGIDVTSQGVLAWAFSNVAVDDPSDPQSTFSEHTDFGFFGIDYSTDSANYQNYL
N[DSGNPTTSTKPTSTSSSVTTGPTVSK]KNTTTYDYIVGGGTSGLVANRLSENPDVSVLLEAGASVFNNPDVTNANGYGLAFGSAID
WQIYQSINQSYAGGKQQVLRAGKALGGTSTINGMAYTRAEDVQIDVWQKLGNEGWTWKDLLPYYLKSENLTAPTSSQVAAGAAYNPAVNG
KEGPLKVGWSGSLASGNLSVALNRTFQAAGYPWVEDVNGGKMRGFNIYPSTLDVDLNVREDAARAYYFPYDDRKNLHLLENTTANRLFW
KNGSAEEALADGVEITSADGKVTRVHAKKEVIISAGALRSPLILELSGVGNPTILKKNNITPRVDLPTVGENLQDQFNNGMAGEGYGVLAGA
STVTYPSISDVFGNETDSIVASLRSQLSDYAAATVKVSNGHIMKQEDLERLYQLQFDLIVKDKVPLAEILFIPGGGKAVSSEFWGLLPFARGNI
HISSNDPTAPAAINPNYFMFEWDGKSQAGHAKYIRKILRSAPLNKLIAKEFTKPGLSEIPATAADEKWVEWLKANYRSNFHPVGTAAMMPRSI
GGVVDNRLRVYGTSNVRVVDASVLPFQVCGHLVSTLYAVAERASDLIKEDAKSA (SEQ ID NO: 16)

PcCDH heme—AfGDH Asn430Arg:

QSASQFTDPTTGFQFTGITDPVHDVTYGFVFPPLATSGAQSTEFIGEVVAPIASKWIGIALGGAMNNDLLYAWANGNQIVSSTRWATGYVQP
TAYTGTATLTTLPETTINSTHWIKWVFRCQGCTEWNNGGGIDVTSQGVLAWAFSNVAVDDPSDPQSTFSEHTDFGFFGIDYSTDSANYQNYL
N[DSGNPTTSTKPTSTSSSVTTGPTVSK]KNTTTYDYIVGGGTSGLVANRLSENPDVSVLLEAGASVFNNPDVTNANGYGLAFGSAID
WQIYQSINQSYAGGKQQVLRAGKALGGTSTINGMAYTRAEDVQIDVWQKLGNEGWTWKDLLPYYLKSENLTAPTSSQVAAGAAYNPAVNG
KEGPLKVGWSGSLASGNLSVALNRTFQAAGYPWVEDVNGGKMRGFNIYPSTLDVDLNVREDAARAYYFPYDDRKNLHLLENTTANRLFW
KNGSAEEALADGVEITSADGKVTRVHAKKEVIISAGALRSPLILELSGVGNPTILKKNNITPRVDLPTVGENLQDQFNNGMAGEGYGVLAGA
STVTYPSISDVFGNETDSIVASLRSQLSDYAAATVKVSNGHIMKQEDLERLYQLQFDLIVKDKVPLAEILFHPGGGRAVSSEFWGLLPFARGNI
HISSNDPTAPAAINPNYFMFEWDGKSQAGHAKYIRKILRSAPLNKLIAKEFTKPGLSEIPATAADEKWVEWLKANYRSNFHPVGTAAMMPRSI
GGVVDNRLRVYGTSNVRVVDASVLPFQVCGHLVSTLYAVAERASDLIKEDAKSA (SEQ ID NO: 17)

FIG. 6D

PcCDH heme—AfGDH Thr498Lys:

QSASQFTDPTTGFQFTGITDPVHDVTYGFVFPPLATSGAQSTEFIGEVVAPIASKWIGIALGGAMNNDLLYAWANGNQIVSSTRWATGYVQPTAYTGTATLFTLPETTINSTHWKWVFRCQGCTEWNNGGGIDVTSQGVLAWAFSNVAVDDPSDPQSTFSEHTDFGFFGIDYSTDSANYQNYLN*HDSGNPTTTSFKPTSTSSSVTTGPTVSKI*KNTTTYDYIVVGGGTSGLVVANRLSENPDVSVLLEAGASVFNNPDVTNANGYGLAFGSAIDWQYQSINQSYAGGKQQVLRAGKALGGTSTINGMAYTRAEDVQIDVWQKLGNEGWTWKDLLPYYLKSENLTAPTSSQVAAGAAYNPAVNGKEGPLKVGWSGGSLASGNLSVALNRTFQAAGVPWVEDVNGGKMRGFNIYPSTLDVDLNVREDAARAYYFPYDDRKNLILLENTTANRLFWKNGSAEEAIADGVEITSADGKVTRVHAKKEVIISAGALRSPLILELSGVGNPTILKKNNITPRVDLPTVGENLQDQFNNGMAGEGYGVLAGASTVTYPSISDVFGNETDSIVASLRSQLSDYAAATVKVSNGHMKQEDLERLYQLQFDLIVKDKVPIAEILFHPGGGNAVSSEFWGLLPFARGNIHISSNDPTAPAAINPNYFMFEWDGKSQAGIAKYIRKILRSAPLNKLIAKEKKPGLSEIPATAADEKWVEWLKANYRSNFHPVGTAAMMPRSIGGVVDNRLRVYGTSNVRVVDASVLPFQVCGHLVSTLYAVAERASDLIKEDAKSA (SEQ ID NO: 18)

PcCDH heme—AfGDH Thr498Arg:

QSASQFTDPTTGFQFTGITDPVHDVTYGFVFPPLATSGAQSTEFIGEVVAPIASKWIGIALGGAMNNDLLYAWANGNQIVSSTRWATGYVQPTAYTGTATLFTLPETTINSTHWKWVFRCQGCTEWNNGGGIDVTSQGVLAWAFSNVAVDDPSDPQSTFSEHTDFGFFGIDYSTDSANYQNYLN*HDSGNPTTTSTKPTSTSSSVTTGPTVSKI*KNTTTYDYIVVGGGTSGLVVANRLSENPDVSVLLEAGASVFNNPDVTNANGYGLAFGSAIDWQYQSINQSYAGGKQQVLRAGKALGGTSTINGMAYTRAEDVQIDVWQKLGNEGWTWKDLLPYYLKSENLTAPTSSQVAAGAAYNPAVNGKEGPLKVGWSGGSLASGNLSVALNRTFQAAGVPWVEDVNGGKMRGFNIYPSTLDVDLNVREDAARAYYFPYDDRKNLILLENTTANRLFWKNGSAEEAIADGVEITSADGKVTRVHAKKEVIISAGALRSPLILELSGVGNPTILKKNNITPRVDLPTVGENLQDQFNNGMAGEGYGVLAGASTVTYPSISDVFGNETDSIVASLRSQLSDYAAATVKVSNGHMKQEDLERLYQLQFDLIVKDKVPIAEILFHPGGGNAVSSEFWGLLPFARGNIHISSNDPTAPAAINPNYFMFEWDGKSQAGIAKYIRKILRSAPLNKLIAKERKPGLSEIPATAADEKWVEWLKANYRSNFHPVGTAAMMPRSIGGVVDNRLRVYGTSNVRVVDASVLPFQVCGHLVSTLYAVAERASDLIKEDAKSA (SEQ ID NO: 19)

FIG. 6E

PcCDH heme—AfGDH Glu504Lys:

QSASQFTDPTTGFQFTGITDPVHDVTYGFVFPPLATSGAQSTEFIGEVVAPIASKWIGIALGGAMNNDLLYAWANGNQIVSSTRWATGYVQP
TAYTGTATLTTLPETTINSTHWKWVFRCQGCTEWNNGGHDVTSQGVLAWAFSNVAVDDPSDPQSTFSEHTDFGFFGIDYSTDSANYQNYL
NHDSGNPTTTSTKPTSTSSSVTTGPTVSKLKNTTTYDYIVGGGTSGLVVANRLSENPDVSVLLLEAGASVFNNPDVTNANGYGLAFGSAID
WQYQSINQSYAGGKQQVLRAGKALGGTSTINGMAYTRAEDVQIDVWQKLGNEGWTWKDLLPYYLKSENLTAPTSSQVAAGAAYNPAVNGK
EGPLKVGWSGSLASGNLSVALNRTFQAAGVPWVEDVNGGKMRGFNIYPSTLDVDLNVREDAARAYYFPYDDRKNLHLLENTTANRLFWK
NGSAEEAIADGVEITSADGKVTRVHAKKEVIISAGALRSPLILELSGVGNPTILKKNNITPRVDLPTVGENLQDQFNNGMAGEGYGVLAGAS
TVTYPSISDVFGNETDSIVASLRSQLSDYAAATVKVSNGHMKQEDLERLYQLQFDLIVKDKVPIAEILFHPGGGNAVSSEFWGLLPFARGNIH
ISSNDPTAPAAINPNYFMFEWDGKSQAGIAKYIRKILRSAPLNKLIAKETKPGLSKIPATAADEKWVEWLKANYRSNFHPVGTAAMMPRSIG
GVVDNRLRVYGTSNVRVVDASVLPFQVCGHLVSTLYAVAERASDLIKEDAKSA (SEQ ID NO: 20)

PcCDH heme—AfGDH Glu504Arg:

QSASQFTDPTTGFQFTGITDPVHDVTYGFVFPPLATSGAQSTEFIGEVVAPIASKWIGIALGGAMNNDLLYAWANGNQIVSSTRWATGYVQP
TAYTGTATLTTLPETTINSTHWKWVFRCQGCTEWNNGGHDVTSQGVLAWAFSNVAVDDPSDPQSTFSEHTDFGFFGIDYSTDSANYQNYL
NHDSGNPTTTSTKPTSTSSSVTTGPTVSKLKNTTTYDYIVGGGTSGLVVANRLSENPDVSVLLLEAGASVFNNPDVTNANGYGLAFGSAID
WQYQSINQSYAGGKQQVLRAGKALGGTSTINGMAYTRAEDVQIDVWQKLGNEGWTWKDLLPYYLKSENLTAPTSSQVAAGAAYNPAVNGK
EGPLKVGWSGSLASGNLSVALNRTFQAAGVPWVEDVNGGKMRGFNIYPSTLDVDLNVREDAARAYYFPYDDRKNLHLLENTTANRLFWK
NGSAEEAIADGVEITSADGKVTRVHAKKEVIISAGALRSPLILELSGVGNPTILKKNNITPRVDLPTVGENLQDQFNNGMAGEGYGVLAGAS
TVTYPSISDVFGNETDSIVASLRSQLSDYAAATVKVSNGHMKQEDLERLYQLQFDLIVKDKVPIAEILFHPGGGNAVSSEFWGLLPFARGNIH
ISSNDPTAPAAINPNYFMFEWDGKSQAGIAKYIRKILRSAPLNKLIAKETKPGLSRIPATAADEKWVEWLKANYRSNFHPVGTAAMMPRSIG
GVVDNRLRVYGTSNVRVVDASVLPFQVCGHLVSTLYAVAERASDLIKEDAKSA (SEQ ID NO: 21)

SEQUENCE LISTING

```
<160> NUMBER OF SEQ ID NOS: 34

<210> SEQ ID NO 1
<211> LENGTH: 704
<212> TYPE: PRT
<213> ORGANISM: Artificial Sequence
<220> FEATURE:
<223> OTHER INFORMATION: fugion protein

<400> SEQUENCE: 1

Met Thr Asp Ser Thr Leu Asn Tyr Asp Tyr Ile Ile Val Gly Ala Gly
1               5                   10                  15

Thr Ser Gly Leu Val Ile Ala Asn Arg Leu Ser Glu Leu Asn Val Thr
            20                  25                  30

Val Ala Val Ile Glu Ala Gly Asp Ser Gly Tyr Asn Asn Pro Asn Val
        35                  40                  45
```

```
Thr Asn Pro Ser Gly Tyr Gly Ser Ala Phe Gly Thr Asp Ile Asp Trp
     50                  55                  60

Ala Tyr Gln Ser Ile Asn Gln Lys Tyr Ala Gly Asn Lys Thr Gln Thr
 65                  70                  75                  80

Leu Arg Ala Gly Lys Val Ile Gly Gly Thr Ser Thr Ile Asn Gly Met
                 85                  90                  95

Ala Tyr Thr Arg Ala Glu Asp Val Gln Ile Asp Ala Trp Glu Ala Ile
            100                 105                 110

Gly Asn Asp Gly Trp Asn Trp Ala Asn Leu Phe Pro Tyr Tyr Lys Lys
        115                 120                 125

Ser Gln Thr Leu Glu Ile Pro Thr Thr Thr Gln Ala Glu Ala Gly Ala
130                 135                 140

Thr Tyr Asp Ala Ser Cys Asn Gly Phe Asp Gly Pro Leu Lys Val Gly
145                 150                 155                 160

Trp Leu Asn Ser Leu Arg Asp Pro Asn Asn Phe His Thr Thr Leu Arg
                165                 170                 175

Asp Thr Tyr Ala Ala Leu Gly Val Pro Ser Asn Asp Asp Val Asn Cys
            180                 185                 190

Gly Lys Met Val Gly Tyr Ser Arg Tyr Pro Ala Thr Tyr Asp Ser Ala
        195                 200                 205

Leu Asn Val Arg His Asp Ala Gly Arg Ala Tyr Tyr Tyr Pro Ile Ala
210                 215                 220

Asn Arg Thr Asn Leu His Leu Tyr Pro Asn Thr Leu Ala Gln Arg Ile
225                 230                 235                 240

Thr Trp Lys Ser Asn Thr Asp Thr Pro Thr Ala Asn Gly Ile Glu Val
                245                 250                 255

Leu Pro Asn Asp Ser Ser Thr Pro Tyr Thr Ile Tyr Ala Asn Ser Glu
            260                 265                 270

Val Ile Leu Ser Ala Gly Ala Leu Ala Ser Pro Leu Leu Leu Glu Leu
        275                 280                 285

Ser Gly Ile Gly Asn Pro Ser Ile Leu Asn Glu His Lys Ile Ser Val
290                 295                 300

Val Val Asp Leu Pro Thr Val Gly Glu Asn Leu Gln Asp Gln Thr Asn
305                 310                 315                 320

Thr Gly Leu Ala Tyr Asn Ser Ser Gly Lys Thr Ser Phe Ser Gly Ala
                325                 330                 335

Gly Thr Leu Val Ala Tyr Pro Ser Ala Ala Gln Val Phe Gly Ser Glu
            340                 345                 350

Val Gln Asn Ile Ser Ala His Val Leu Gln Ser Leu Pro Ser Tyr Ala
        355                 360                 365

Glu Gln Val Ser Ala Ala Ser Gly Asn Ile Thr Lys Ala Thr Asp Leu
370                 375                 380

Leu Glu Phe Phe Lys Val Gln His Asp Leu Ile Phe Ser Thr Thr His
385                 390                 395                 400

Pro Val Pro Met Ala Glu Ile Leu Ile Ile Pro Ser Ala Thr Ser Phe
                405                 410                 415

Ser Ser Glu Tyr Trp Ala Leu Leu Pro Phe Ala Arg Gly Ser Ile His
            420                 425                 430

Ile Thr Ser Ser Val Ala Gly Glu Pro Ala Ala Ile Asn Pro Asn Tyr
        435                 440                 445

Tyr Met Phe Asp Trp Asp Ile Thr Ser Gln Ile Ser Thr Ala Lys Phe
450                 455                 460
```

```
Ile Arg Ser Val Phe Glu Thr Ser Pro Phe Ser Phe Val Gly Ser
465                 470                 475                 480

Glu Thr Lys Pro Gly Leu Asn Thr Val Pro Ala Asn Ala Thr Glu Ala
            485                 490                 495

Glu Trp Phe Glu Trp Val Lys Thr Ala Tyr Arg Ser Asn Phe His Pro
            500                 505                 510

Val Gly Thr Ala Ala Met Met Pro Arg Glu Val Gly Val Val Asp
        515                 520                 525

Ser Lys Leu Lys Val Tyr Gly Thr Ala Asn Val Arg Val Val Asp Ala
    530                 535                 540

Ser Ile Leu Pro Met Gln Val Cys Gly His Leu Val Ser Thr Leu Tyr
545                 550                 555                 560

Ala Val Ala Glu Arg Ala Ala Asp Leu Ile Lys Glu Asp Ile Val Ala
            565                 570                 575

Gly Lys Ala Arg Met Pro Glu Phe Val Ala Gln Arg Thr Gly Gln Leu
        580                 585                 590

Leu Gln Gly Val Lys Tyr Ala Asp Leu Glu Asp Asn Met Glu Thr Leu
    595                 600                 605

Asn Asp Asn Leu Lys Val Ile Glu Lys Ala Asp Asn Ala Ala Gln Val
610                 615                 620

Lys Asp Ala Leu Thr Lys Met Arg Ala Ala Ala Leu Asp Ala Gln Lys
625                 630                 635                 640

Ala Thr Pro Pro Lys Leu Glu Asp Lys Ser Pro Asp Ser Pro Glu Met
            645                 650                 655

Lys Asp Phe Arg His Gly Phe Asp Ile Leu Val Gly Gln Ile Asp Asp
        660                 665                 670

Ala Leu Lys Leu Ala Asn Glu Gly Lys Val Lys Glu Ala Gln Ala Ala
    675                 680                 685

Ala Glu Gln Leu Lys Thr Thr Arg Asn Ala Tyr His Gln Lys Tyr Arg
690                 695                 700

<210> SEQ ID NO 2
<211> LENGTH: 705
<212> TYPE: PRT
<213> ORGANISM: Artificial Sequence
<220> FEATURE:
<223> OTHER INFORMATION: fugion protein

<400> SEQUENCE: 2

Met Ala Asp Leu Glu Asp Asn Met Glu Thr Leu Asn Asp Asn Leu Lys
1               5                   10                  15

Val Ile Glu Lys Ala Asp Asn Ala Ala Gln Val Lys Asp Ala Leu Thr
            20                  25                  30

Lys Met Arg Ala Ala Ala Leu Asp Ala Gln Lys Ala Thr Pro Pro Lys
        35                  40                  45

Leu Glu Asp Lys Ser Pro Asp Ser Pro Glu Met Lys Asp Phe Arg His
    50                  55                  60

Gly Phe Asp Ile Leu Val Gly Gln Ile Asp Asp Ala Leu Lys Leu Ala
65                  70                  75                  80

Asn Glu Gly Lys Val Lys Glu Ala Gln Ala Ala Ala Glu Gln Leu Lys
            85                  90                  95

Thr Thr Arg Asn Ala Tyr His Gln Lys Tyr Arg Asn Gly Asp Ser Gly
        100                 105                 110

Asn Pro Thr Thr Thr Ser Thr Lys Pro Thr Ser Thr Ser Ser Ser Val
    115                 120                 125
```

```
Thr Thr Gly Pro Thr Val Ser Ala Thr Pro Tyr Asp Tyr Ile Ile Val
        130                 135                 140
Gly Ala Gly Thr Ser Gly Leu Val Ile Ala Asn Arg Leu Ser Glu Leu
145                 150                 155                 160
Asn Val Thr Val Ala Val Ile Glu Ala Gly Asp Ser Gly Tyr Asn Asn
                165                 170                 175
Pro Asn Val Thr Asn Pro Ser Gly Tyr Gly Ser Ala Phe Gly Thr Asp
            180                 185                 190
Ile Asp Trp Ala Tyr Gln Ser Ile Asn Gln Lys Tyr Ala Gly Asn Lys
        195                 200                 205
Thr Gln Thr Leu Arg Ala Gly Lys Val Ile Gly Gly Thr Ser Thr Ile
    210                 215                 220
Asn Gly Met Ala Tyr Thr Arg Ala Glu Asp Val Gln Ile Asp Ala Trp
225                 230                 235                 240
Glu Ala Ile Gly Asn Asp Gly Trp Asn Trp Ala Asn Leu Phe Pro Tyr
                245                 250                 255
Tyr Lys Lys Ser Gln Thr Leu Glu Ile Pro Thr Thr Thr Gln Ala Glu
            260                 265                 270
Ala Gly Ala Thr Tyr Asp Ala Ser Cys Asn Gly Phe Asp Gly Pro Leu
        275                 280                 285
Lys Val Gly Trp Leu Asn Ser Leu Arg Asp Pro Asn Asn Phe His Thr
    290                 295                 300
Thr Leu Arg Asp Thr Tyr Ala Ala Leu Gly Val Pro Ser Asn Asp Asp
305                 310                 315                 320
Val Asn Cys Gly Lys Met Val Gly Tyr Ser Arg Tyr Pro Ala Thr Tyr
                325                 330                 335
Asp Ser Ala Leu Asn Val Arg His Asp Ala Gly Arg Ala Tyr Tyr Tyr
            340                 345                 350
Pro Ile Ala Asn Arg Thr Asn Leu His Leu Tyr Pro Asn Thr Leu Ala
        355                 360                 365
Gln Arg Ile Thr Trp Lys Ser Asn Thr Asp Thr Pro Thr Ala Asn Gly
    370                 375                 380
Ile Glu Val Leu Pro Asn Asp Ser Ser Thr Pro Tyr Thr Ile Tyr Ala
385                 390                 395                 400
Asn Ser Glu Val Ile Leu Ser Ala Gly Ala Leu Ala Ser Pro Leu Leu
                405                 410                 415
Leu Glu Leu Ser Gly Ile Gly Asn Pro Ser Ile Leu Asn Glu His Lys
            420                 425                 430
Ile Ser Val Val Val Asp Leu Pro Thr Val Gly Glu Asn Leu Gln Asp
        435                 440                 445
Gln Thr Asn Thr Gly Leu Ala Tyr Asn Ser Ser Gly Lys Thr Ser Phe
    450                 455                 460
Ser Gly Ala Gly Thr Leu Val Ala Tyr Pro Ser Ala Ala Gln Val Phe
465                 470                 475                 480
Gly Ser Glu Val Gln Asn Ile Ser Ala His Val Leu Gln Ser Leu Pro
                485                 490                 495
Ser Tyr Ala Glu Gln Val Ser Ala Ala Ser Gly Asn Ile Thr Lys Ala
            500                 505                 510
Thr Asp Leu Leu Glu Phe Phe Lys Val Gln His Asp Leu Ile Phe Ser
        515                 520                 525
Thr Thr His Pro Val Pro Met Ala Glu Ile Leu Ile Ile Pro Ser Ala
    530                 535                 540
Thr Ser Phe Ser Ser Glu Tyr Trp Ala Leu Leu Pro Phe Ala Arg Gly
```

```
545                 550                 555                 560
Ser Ile His Ile Thr Ser Ser Val Ala Gly Glu Pro Ala Ala Ile Asn
                565                 570                 575

Pro Asn Tyr Tyr Met Phe Asp Trp Asp Ile Thr Ser Gln Ile Ser Thr
                580                 585                 590

Ala Lys Phe Ile Arg Ser Val Phe Glu Thr Ser Pro Phe Ser Ser Phe
                595                 600                 605

Val Gly Ser Glu Thr Lys Pro Gly Leu Asn Thr Val Pro Ala Asn Ala
    610                 615                 620

Thr Glu Ala Glu Trp Phe Glu Trp Val Lys Thr Ala Tyr Arg Ser Asn
625                 630                 635                 640

Phe His Pro Val Gly Thr Ala Ala Met Met Pro Arg Glu Val Gly Gly
                645                 650                 655

Val Val Asp Ser Lys Leu Lys Val Tyr Gly Thr Ala Asn Val Arg Val
                660                 665                 670

Val Asp Ala Ser Ile Leu Pro Met Gln Val Cys Gly His Leu Val Ser
                675                 680                 685

Thr Leu Tyr Ala Val Ala Glu Arg Ala Ala Asp Leu Ile Lys Glu Asp
    690                 695                 700

Ile
705

<210> SEQ ID NO 3
<211> LENGTH: 785
<212> TYPE: PRT
<213> ORGANISM: Artificial Sequence
<220> FEATURE:
<223> OTHER INFORMATION: fugion protein

<400> SEQUENCE: 3

Gln Ser Ala Ser Gln Phe Thr Asp Pro Thr Thr Gly Phe Gln Phe Thr
1               5                   10                  15

Gly Ile Thr Asp Pro Val His Asp Val Thr Tyr Gly Phe Val Phe Pro
                20                  25                  30

Pro Leu Ala Thr Ser Gly Ala Gln Ser Thr Glu Phe Ile Gly Glu Val
            35                  40                  45

Val Ala Pro Ile Ala Ser Lys Trp Ile Gly Ile Ala Leu Gly Gly Ala
    50                  55                  60

Met Asn Asn Asp Leu Leu Leu Val Ala Trp Ala Asn Gly Asn Gln Ile
65                  70                  75                  80

Val Ser Ser Thr Arg Trp Ala Thr Gly Tyr Val Gln Pro Thr Ala Tyr
                85                  90                  95

Thr Gly Thr Ala Thr Leu Thr Thr Leu Pro Glu Thr Thr Ile Asn Ser
            100                 105                 110

Thr His Trp Lys Trp Val Phe Arg Cys Gln Gly Cys Thr Glu Trp Asn
        115                 120                 125

Asn Gly Gly Gly Ile Asp Val Thr Ser Gln Gly Val Leu Ala Trp Ala
    130                 135                 140

Phe Ser Asn Val Ala Val Asp Asp Pro Ser Asp Pro Gln Ser Thr Phe
145                 150                 155                 160

Ser Glu His Thr Asp Phe Gly Phe Phe Gly Ile Asp Tyr Ser Thr Asp
                165                 170                 175

Ser Ala Asn Tyr Gln Asn Tyr Leu Asn Gly Asp Ser Gly Asn Pro Thr
            180                 185                 190

Thr Thr Ser Thr Lys Pro Thr Ser Thr Ser Ser Ser Val Thr Thr Gly
```

-continued

```
            195                 200                 205
Pro Thr Val Ser Lys Leu Lys Asn Thr Thr Tyr Asp Tyr Ile Val
    210                 215                 220
Val Gly Gly Gly Thr Ser Gly Leu Val Val Ala Asn Arg Leu Ser Glu
225                 230                 235                 240
Asn Pro Asp Val Ser Val Leu Leu Leu Glu Ala Gly Ala Ser Val Phe
                245                 250                 255
Asn Asn Pro Asp Val Thr Asn Ala Asn Gly Tyr Gly Leu Ala Phe Gly
                260                 265                 270
Ser Ala Ile Asp Trp Gln Tyr Gln Ser Ile Asn Gln Ser Tyr Ala Gly
            275                 280                 285
Gly Lys Gln Gln Val Leu Arg Ala Gly Lys Ala Leu Gly Gly Thr Ser
290                 295                 300
Thr Ile Asn Gly Met Ala Tyr Thr Arg Ala Glu Asp Val Gln Ile Asp
305                 310                 315                 320
Val Trp Gln Lys Leu Gly Asn Glu Gly Trp Thr Trp Lys Asp Leu Leu
                325                 330                 335
Pro Tyr Tyr Leu Lys Ser Glu Asn Leu Thr Ala Pro Thr Ser Ser Gln
                340                 345                 350
Val Ala Gly Ala Ala Tyr Asn Pro Ala Val Asn Gly Lys Glu Gly
            355                 360                 365
Pro Leu Lys Val Gly Trp Ser Gly Ser Leu Ala Ser Gly Asn Leu Ser
            370                 375                 380
Val Ala Leu Asn Arg Thr Phe Gln Ala Ala Gly Val Pro Trp Val Glu
385                 390                 395                 400
Asp Val Asn Gly Gly Lys Met Arg Gly Phe Asn Ile Tyr Pro Ser Thr
                405                 410                 415
Leu Asp Val Asp Leu Asn Val Arg Glu Asp Ala Ala Arg Ala Tyr Tyr
                420                 425                 430
Phe Pro Tyr Asp Asp Arg Lys Asn Leu His Leu Leu Glu Asn Thr Thr
            435                 440                 445
Ala Asn Arg Leu Phe Trp Lys Asn Gly Ser Ala Glu Glu Ala Ile Ala
    450                 455                 460
Asp Gly Val Glu Ile Thr Ser Ala Asp Gly Lys Val Thr Arg Val His
465                 470                 475                 480
Ala Lys Lys Glu Val Ile Ile Ser Ala Gly Ala Leu Arg Ser Pro Leu
                485                 490                 495
Ile Leu Glu Leu Ser Gly Val Gly Asn Pro Thr Ile Leu Lys Lys Asn
                500                 505                 510
Asn Ile Thr Pro Arg Val Asp Leu Pro Thr Val Gly Glu Asn Leu Gln
            515                 520                 525
Asp Gln Phe Asn Asn Gly Met Ala Gly Glu Gly Tyr Gly Val Leu Ala
    530                 535                 540
Gly Ala Ser Thr Val Thr Tyr Pro Ser Ile Ser Asp Val Phe Gly Asn
545                 550                 555                 560
Glu Thr Asp Ser Ile Val Ala Ser Leu Arg Ser Gln Leu Ser Asp Tyr
                565                 570                 575
Ala Ala Ala Thr Val Lys Val Ser Asn Gly His Met Lys Gln Glu Asp
            580                 585                 590
Leu Glu Arg Leu Tyr Gln Leu Gln Phe Asp Leu Ile Val Lys Asp Lys
            595                 600                 605
Val Pro Ile Ala Glu Ile Leu Phe His Pro Gly Gly Gly Asn Ala Val
            610                 615                 620
```

```
Ser Ser Glu Phe Trp Gly Leu Leu Pro Phe Ala Arg Gly Asn Ile His
625                 630                 635                 640

Ile Ser Ser Asn Asp Pro Thr Ala Pro Ala Ile Asn Pro Asn Tyr
        645                 650                 655

Phe Met Phe Glu Trp Asp Gly Lys Ser Gln Ala Gly Ile Ala Lys Tyr
            660                 665                 670

Ile Arg Lys Ile Leu Arg Ser Ala Pro Leu Asn Lys Leu Ile Ala Lys
            675                 680                 685

Glu Thr Lys Pro Gly Leu Ser Glu Ile Pro Ala Thr Ala Ala Asp Glu
690                 695                 700

Lys Trp Val Glu Trp Leu Lys Ala Asn Tyr Arg Ser Asn Phe His Pro
705                 710                 715                 720

Val Gly Thr Ala Ala Met Met Pro Arg Ser Ile Gly Gly Val Val Asp
            725                 730                 735

Asn Arg Leu Arg Val Tyr Gly Thr Ser Asn Val Arg Val Val Asp Ala
            740                 745                 750

Ser Val Leu Pro Phe Gln Val Cys Gly His Leu Val Ser Thr Leu Tyr
            755                 760                 765

Ala Val Ala Glu Arg Ala Ser Asp Leu Ile Lys Glu Asp Ala Lys Ser
    770                 775                 780

Ala
785

<210> SEQ ID NO 4
<211> LENGTH: 593
<212> TYPE: PRT
<213> ORGANISM: Aspergillus flavus

<400> SEQUENCE: 4

Met Leu Phe Ser Leu Ala Phe Leu Ser Ala Leu Ser Leu Ala Thr Ala
1               5                   10                  15

Ser Pro Ala Gly Arg Ala Lys Asn Thr Thr Tyr Asp Tyr Ile Val
            20                  25                  30

Val Gly Gly Gly Thr Ser Gly Leu Val Val Ala Asn Arg Leu Ser Glu
        35                  40                  45

Asn Pro Asp Val Ser Val Leu Leu Glu Gly Ala Ser Val Phe
    50                  55                  60

Asn Asn Pro Asp Val Thr Asn Ala Asn Gly Tyr Gly Leu Ala Phe Gly
65                  70                  75                  80

Ser Ala Ile Asp Trp Gln Tyr Gln Ser Ile Asn Gln Ser Tyr Ala Gly
            85                  90                  95

Gly Lys Gln Gln Val Leu Arg Ala Gly Lys Ala Leu Gly Gly Thr Ser
            100                 105                 110

Thr Ile Asn Gly Met Ala Tyr Thr Arg Ala Glu Asp Val Gln Ile Asp
        115                 120                 125

Val Trp Gln Lys Leu Gly Asn Glu Gly Trp Thr Trp Lys Asp Leu Leu
    130                 135                 140

Pro Tyr Tyr Leu Lys Ser Glu Asn Leu Thr Ala Pro Thr Ser Ser Gln
145                 150                 155                 160

Val Ala Ala Gly Ala Ala Tyr Asn Pro Val Asn Gly Lys Glu Gly
                165                 170                 175

Pro Leu Lys Val Gly Trp Ser Gly Ser Leu Ala Ser Gly Asn Leu Ser
            180                 185                 190

Val Ala Leu Asn Arg Thr Phe Gln Ala Ala Gly Val Pro Trp Val Glu
```

```
                195                 200                 205
Asp Val Asn Gly Gly Lys Met Arg Gly Phe Asn Ile Tyr Pro Ser Thr
210                 215                 220

Leu Asp Val Asp Leu Asn Val Arg Glu Asp Ala Ala Arg Ala Tyr Tyr
225                 230                 235                 240

Phe Pro Tyr Asp Asp Arg Lys Asn Leu His Leu Leu Glu Asn Thr Thr
                245                 250                 255

Ala Asn Arg Leu Phe Trp Lys Asn Gly Ser Ala Glu Glu Ala Ile Ala
            260                 265                 270

Asp Gly Val Glu Ile Thr Ser Ala Asp Gly Lys Val Thr Arg Val His
        275                 280                 285

Ala Lys Lys Glu Val Ile Ile Ser Ala Gly Ala Leu Arg Ser Pro Leu
290                 295                 300

Ile Leu Glu Leu Ser Gly Val Gly Asn Pro Thr Ile Leu Lys Lys Asn
305                 310                 315                 320

Asn Ile Thr Pro Arg Val Asp Leu Pro Thr Val Gly Glu Asn Leu Gln
                325                 330                 335

Asp Gln Phe Asn Asn Gly Met Ala Gly Glu Gly Tyr Gly Val Leu Ala
            340                 345                 350

Gly Ala Ser Thr Val Thr Tyr Pro Ser Ile Ser Asp Val Phe Gly Asn
        355                 360                 365

Glu Thr Asp Ser Ile Val Ala Ser Leu Arg Ser Gln Leu Ser Asp Tyr
370                 375                 380

Ala Ala Ala Thr Val Lys Val Ser Asn Gly His Met Lys Gln Glu Asp
385                 390                 395                 400

Leu Glu Arg Leu Tyr Gln Leu Gln Phe Asp Leu Ile Val Lys Asp Lys
                405                 410                 415

Val Pro Ile Ala Glu Ile Leu Phe His Pro Gly Gly Asn Ala Val
            420                 425                 430

Ser Ser Glu Phe Trp Gly Leu Leu Pro Phe Ala Arg Gly Asn Ile His
        435                 440                 445

Ile Ser Ser Asn Asp Pro Thr Ala Pro Ala Ala Ile Asn Pro Asn Tyr
450                 455                 460

Phe Met Phe Glu Trp Asp Gly Lys Ser Gln Ala Gly Ile Ala Lys Tyr
465                 470                 475                 480

Ile Arg Lys Ile Leu Arg Ser Ala Pro Leu Asn Lys Leu Ile Ala Lys
                485                 490                 495

Glu Thr Lys Pro Gly Leu Ser Glu Ile Pro Ala Thr Ala Ala Asp Glu
            500                 505                 510

Lys Trp Val Glu Trp Leu Lys Ala Asn Tyr Arg Ser Asn Phe His Pro
        515                 520                 525

Val Gly Thr Ala Ala Met Met Pro Arg Ser Ile Gly Gly Val Val Asp
530                 535                 540

Asn Arg Leu Arg Val Tyr Gly Thr Ser Asn Val Arg Val Val Asp Ala
545                 550                 555                 560

Ser Val Leu Pro Phe Gln Val Cys Gly His Leu Val Ser Thr Leu Tyr
                565                 570                 575

Ala Val Ala Glu Arg Ala Ser Asp Leu Ile Lys Glu Asp Ala Lys Ser
            580                 585                 590

Ala

<210> SEQ ID NO 5
<211> LENGTH: 574
```

<212> TYPE: PRT
<213> ORGANISM: Botryothinia fuckeliana

<400> SEQUENCE: 5

```
Met Thr Asp Ser Thr Leu Asn Tyr Asp Tyr Ile Ile Val Gly Ala Gly
1               5                   10                  15

Thr Ser Gly Leu Val Ile Ala Asn Arg Leu Ser Glu Leu Asn Val Thr
            20                  25                  30

Val Ala Val Ile Glu Ala Gly Asp Ser Gly Tyr Asn Asn Pro Asn Val
        35                  40                  45

Thr Asn Pro Ser Gly Tyr Gly Ser Ala Phe Gly Thr Asp Ile Asp Trp
    50                  55                  60

Ala Tyr Gln Ser Ile Asn Gln Lys Tyr Ala Gly Asn Lys Thr Gln Thr
65                  70                  75                  80

Leu Arg Ala Gly Lys Val Ile Gly Gly Thr Ser Thr Ile Asn Gly Met
                85                  90                  95

Ala Tyr Thr Arg Ala Glu Asp Val Gln Ile Asp Ala Trp Glu Ala Ile
            100                 105                 110

Gly Asn Asp Gly Trp Asn Trp Ala Asn Leu Phe Pro Tyr Tyr Lys Lys
        115                 120                 125

Ser Gln Thr Leu Glu Ile Pro Thr Thr Thr Gln Ala Glu Ala Gly Ala
    130                 135                 140

Thr Tyr Asp Ala Ser Ala Asn Gly Phe Asp Gly Pro Leu Lys Val Gly
145                 150                 155                 160

Trp Leu Asn Ser Leu Glu Asp Thr Asn Asn Phe His Thr Thr Leu Asn
                165                 170                 175

Asp Thr Tyr Ala Ala Leu Gly Val Pro Ser Asn Asp Val Asn Thr
            180                 185                 190

Gly Lys Met Val Gly Tyr Ser Arg Tyr Pro Ala Thr Tyr Asp Ser Ala
        195                 200                 205

Leu Asn Val Arg His Asp Ala Gly Arg Ala Tyr Tyr Tyr Pro Ile Ala
    210                 215                 220

Asn Arg Thr Asn Leu His Leu Tyr Pro Asn Thr Leu Ala Gln Arg Ile
225                 230                 235                 240

Thr Trp Lys Ser Asn Thr Asp Thr Pro Thr Ala Asn Gly Ile Glu Val
                245                 250                 255

Leu Pro Asn Asp Ser Ser Thr Pro Tyr Thr Ile Tyr Ala Asn Ser Glu
            260                 265                 270

Val Ile Leu Ser Ala Gly Ala Leu Ala Ser Pro Leu Leu Leu Glu Leu
        275                 280                 285

Ser Gly Ile Gly Asn Pro Ser Ile Leu Asn Glu His Asn Ile Ser Val
    290                 295                 300

Val Val Asp Leu Pro Thr Val Gly Glu Asn Leu Gln Asp Gln Thr Asn
305                 310                 315                 320

Thr Gly Leu Ala Tyr Asn Ser Ser Gly Asn Thr Ser Phe Ser Gly Ala
                325                 330                 335

Gly Thr Leu Val Ala Tyr Pro Ser Ala Ala Gln Val Phe Gly Ser Glu
            340                 345                 350

Val Gln Asn Ile Ser Ala His Val Leu Gln Ser Leu Pro Ser Tyr Ala
        355                 360                 365

Glu Gln Val Ser Ala Ala Ser Gly Asn Ile Thr Lys Ala Thr Asp Leu
    370                 375                 380

Leu Glu Phe Phe Lys Val Gln His Asp Leu Ile Phe Ser Thr Thr His
385                 390                 395                 400
```

```
Pro Val Pro Met Ala Glu Ile Leu Ile Ile Pro Ser Ala Thr Ser Phe
                405                 410                 415

Ser Ser Glu Tyr Trp Ala Leu Leu Pro Phe Ala Arg Gly Ser Ile His
        420                 425                 430

Ile Thr Ser Ser Val Ala Gly Glu Pro Ala Ala Ile Asn Pro Asn Tyr
            435                 440                 445

Tyr Met Phe Asp Trp Asp Ile Thr Ser Gln Ile Ser Thr Ala Lys Phe
        450                 455                 460

Ile Arg Ser Val Phe Glu Thr Ser Pro Phe Ser Ser Phe Val Gly Ser
465                 470                 475                 480

Glu Thr Lys Pro Gly Leu Asn Thr Val Ser Ala Asn Ala Thr Glu Ala
                485                 490                 495

Glu Trp Phe Asp Trp Val Lys Thr Ala Tyr Arg Ser Asn Phe His Pro
                500                 505                 510

Val Ser Thr Ala Ala Met Met Pro Arg Glu Val Gly Gly Val Val Asp
            515                 520                 525

Ser Lys Leu Lys Val Tyr Gly Thr Ala Asn Val Arg Val Val Asp Ala
        530                 535                 540

Ser Ile Leu Pro Met Gln Val Ser Gly His Leu Val Ser Thr Leu Tyr
545                 550                 555                 560

Ala Val Ala Glu Arg Ala Ala Asp Leu Ile Lys Glu Asp Ile
                565                 570

<210> SEQ ID NO 6
<211> LENGTH: 641
<212> TYPE: PRT
<213> ORGANISM: Mucor prainii

<400> SEQUENCE: 6

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Ser Thr Asp Thr Tyr
            20                  25                  30

Asp Tyr Val Ile Val Gly Gly Gly Val Ala Gly Leu Ala Leu Ala Ser
            35                  40                  45

Arg Ile Ser Glu Asn Lys Asp Val Thr Val Ala Val Leu Glu Ser Gly
50                  55                  60

Pro Asn Ala Asn Asp Arg Phe Val Val Tyr Ala Pro Gly Met Tyr Gly
65                  70                  75                  80

Gln Ala Val Gly Thr Asp Leu Cys Pro Leu Ile Pro Thr Thr Pro Gln
            85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
        115                 120                 125

Lys Asp Tyr Asp Ala Trp Glu Glu Leu Gly Asn Pro Gly Trp Asn Gly
130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
            165                 170                 175

Gly Lys Lys Gly Pro Ile Asp Val Ser Phe Thr Asn Tyr Glu Phe Ser
        180                 185                 190

Gln Ser Ala Ser Trp Asn Ala Ser Leu Glu Thr Leu Asp Phe Thr Ala
```

```
            195                 200                 205
Leu Pro Asp Ile Leu Asn Gly Thr Leu Ala Gly Tyr Ser Thr Thr Pro
210                 215                 220

Asn Ile Leu Asp Pro Glu Thr Val Gln Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
                260                 265                 270

Leu Lys Ala Thr Gly Val Glu Trp Tyr Pro Thr Gly Asn Lys Asn Gln
            275                 280                 285

Lys Gln Ile Ile Lys Ala Arg Tyr Glu Val Ile Ile Ser Ser Gly Ala
290                 295                 300

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335

Gly Ser Asn Met Gln Asp His Val His Ala Ile Thr Val Ser Thr Thr
            340                 345                 350

Asn Ile Thr Gly Tyr Thr Thr Asn Ser Val Phe Val Asn Glu Thr Leu
            355                 360                 365

Ala Gln Glu Gln Arg Glu Glu Tyr Glu Ala Asn Lys Thr Gly Ile Trp
370                 375                 380

Ala Thr Thr Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
                405                 410                 415

Asn Ser Thr Asp Glu Trp Ala Asn Tyr Tyr Ala Ser Thr Asn Ala Ser
                420                 425                 430

Asn Val Glu Leu Leu Lys Lys Gln Tyr Ala Ile Val Ala Ser Arg Tyr
            435                 440                 445

Glu Glu Asn Tyr Leu Ser Pro Ile Glu Ile Asn Phe Thr Pro Gly Tyr
450                 455                 460

Glu Gly Ser Gly Asn Val Asp Leu Gln Asn Asn Lys Tyr Gln Thr Val
465                 470                 475                 480

Asn His Val Leu Ile Ala Pro Leu Ser Arg Gly Tyr Thr His Ile Asn
                485                 490                 495

Ser Ser Asp Val Glu Asp His Ser Val Ile Asn Pro Gln Tyr Tyr Ser
                500                 505                 510

His Pro Met Asp Ile Asp Val His Ile Ala Ser Thr Lys Leu Ala Arg
            515                 520                 525

Glu Ile Ile Thr Ala Ser Pro Gly Leu Gly Asp Ile Asn Ser Gly Glu
530                 535                 540

Ile Glu Pro Gly Met Asn Ile Thr Ser Glu Asp Leu Arg Ser Trp
545                 550                 555                 560

Leu Ser Asn Asn Val Arg Ser Asp Trp His Pro Val Gly Thr Cys Ala
                565                 570                 575

Met Leu Pro Lys Glu Leu Gly Gly Val Val Ser Pro Ala Leu Met Val
            580                 585                 590

Tyr Gly Thr Ser Asn Leu Arg Val Val Asp Ala Ser Ile Met Pro Leu
            595                 600                 605

Glu Val Ser Ser His Leu Met Gln Pro Thr Tyr Gly Ile Ala Glu Lys
610                 615                 620
```

```
Ala Ala Asp Ile Ile Lys Asn Phe Tyr Lys Thr Gln His Lys Asn Gln
625                 630                 635                 640

Asn

<210> SEQ ID NO 7
<211> LENGTH: 574
<212> TYPE: PRT
<213> ORGANISM: Artificial Sequence
<220> FEATURE:
<223> OTHER INFORMATION: synthetic

<400> SEQUENCE: 7

Met Thr Asp Ser Thr Leu Asn Tyr Asp Tyr Ile Ile Val Gly Ala Gly
1               5                   10                  15

Thr Ser Gly Leu Val Ile Ala Asn Arg Leu Ser Glu Leu Asn Val Thr
                20                  25                  30

Val Ala Val Ile Glu Ala Gly Asp Ser Gly Tyr Asn Asn Pro Asn Val
            35                  40                  45

Thr Asn Pro Ser Gly Tyr Gly Ser Ala Phe Gly Thr Asp Ile Asp Trp
        50                  55                  60

Ala Tyr Gln Ser Ile Asn Gln Lys Tyr Ala Gly Asn Lys Thr Gln Thr
65                  70                  75                  80

Leu Arg Ala Gly Lys Val Ile Gly Gly Thr Ser Thr Ile Asn Gly Met
                85                  90                  95

Ala Tyr Thr Arg Ala Glu Asp Val Gln Ile Asp Ala Trp Glu Ala Ile
            100                 105                 110

Gly Asn Asp Gly Trp Asn Trp Ala Asn Leu Phe Pro Tyr Tyr Lys Lys
        115                 120                 125

Ser Gln Thr Leu Glu Ile Pro Thr Thr Thr Gln Ala Glu Ala Gly Ala
    130                 135                 140

Thr Tyr Asp Ala Ser Cys Asn Gly Phe Asp Gly Pro Leu Lys Val Gly
145                 150                 155                 160

Trp Leu Asn Ser Leu Arg Asp Pro Asn Asn Phe His Thr Thr Leu Arg
                165                 170                 175

Asp Thr Tyr Ala Ala Leu Gly Val Pro Ser Asp Asp Val Asn Cys
            180                 185                 190

Gly Lys Met Val Gly Tyr Ser Arg Tyr Pro Ala Thr Tyr Asp Ser Ala
        195                 200                 205

Leu Asn Val Arg His Asp Ala Gly Arg Ala Tyr Tyr Pro Ile Ala
    210                 215                 220

Asn Arg Thr Asn Leu His Leu Tyr Pro Asn Thr Leu Ala Gln Arg Ile
225                 230                 235                 240

Thr Trp Lys Ser Asn Thr Asp Thr Pro Thr Ala Asn Gly Ile Glu Val
                245                 250                 255

Leu Pro Asn Asp Ser Ser Thr Pro Tyr Thr Ile Tyr Ala Asn Ser Glu
            260                 265                 270

Val Ile Leu Ser Ala Gly Ala Leu Ala Ser Pro Leu Leu Glu Leu
        275                 280                 285

Ser Gly Ile Gly Asn Pro Ser Ile Leu Asn Glu His Lys Ile Ser Val
    290                 295                 300

Val Val Asp Leu Pro Thr Val Gly Glu Asn Leu Gln Asp Gln Thr Asn
305                 310                 315                 320

Thr Gly Leu Ala Tyr Asn Ser Ser Gly Lys Thr Ser Phe Ser Gly Ala
                325                 330                 335
```

Gly Thr Leu Val Ala Tyr Pro Ser Ala Ala Gln Val Phe Gly Ser Glu
            340                 345                 350

Val Gln Asn Ile Ser Ala His Val Leu Gln Ser Leu Pro Ser Tyr Ala
    355                 360                 365

Glu Gln Val Ser Ala Ala Ser Gly Asn Ile Thr Lys Ala Thr Asp Leu
    370                 375                 380

Leu Glu Phe Phe Lys Val Gln His Asp Leu Ile Phe Ser Thr Thr His
385                 390                 395                 400

Pro Val Pro Met Ala Glu Ile Leu Ile Pro Ser Ala Thr Ser Phe
                405                 410                 415

Ser Ser Glu Tyr Trp Ala Leu Leu Pro Phe Ala Arg Gly Ser Ile His
        420                 425                 430

Ile Thr Ser Ser Val Ala Gly Glu Pro Ala Ala Ile Asn Pro Asn Tyr
        435                 440                 445

Tyr Met Phe Asp Trp Asp Ile Thr Ser Gln Ile Ser Thr Ala Lys Phe
    450                 455                 460

Ile Arg Ser Val Phe Glu Thr Ser Pro Phe Ser Ser Phe Val Gly Ser
465                 470                 475                 480

Glu Thr Lys Pro Gly Leu Asn Thr Val Pro Ala Asn Ala Thr Glu Ala
                485                 490                 495

Glu Trp Phe Glu Trp Val Lys Thr Ala Tyr Arg Ser Asn Phe His Pro
        500                 505                 510

Val Gly Thr Ala Ala Met Met Pro Arg Glu Val Gly Val Val Asp
        515                 520                 525

Ser Lys Leu Lys Val Tyr Gly Thr Ala Asn Val Arg Val Val Asp Ala
530                 535                 540

Ser Ile Leu Pro Met Gln Val Cys Gly His Leu Val Ser Thr Leu Tyr
545                 550                 555                 560

Ala Val Ala Glu Arg Ala Ala Asp Leu Ile Lys Glu Asp Ile
                565                 570

<210> SEQ ID NO 8
<211> LENGTH: 128
<212> TYPE: PRT
<213> ORGANISM: Escherichia coli

<400> SEQUENCE: 8

Met Arg Lys Ser Leu Leu Ala Ile Leu Ala Val Ser Ser Leu Val Phe
1               5                   10                  15

Ser Ser Ala Ser Phe Ala Ala Asp Leu Glu Asp Asn Met Glu Thr Leu
                20                  25                  30

Asn Asp Asn Leu Lys Val Ile Glu Lys Ala Asp Asn Ala Ala Gln Val
            35                  40                  45

Lys Asp Ala Leu Thr Lys Met Arg Ala Ala Ala Leu Asp Ala Gln Lys
        50                  55                  60

Ala Thr Pro Pro Lys Leu Glu Asp Lys Ser Pro Asp Ser Pro Glu Met
65                  70                  75                  80

Lys Asp Phe Arg His Gly Phe Asp Ile Leu Val Gly Gln Ile Asp Asp
                85                  90                  95

Ala Leu Lys Leu Ala Asn Glu Gly Lys Val Lys Glu Ala Gln Ala Ala
            100                 105                 110

Ala Glu Gln Leu Lys Thr Thr Arg Asn Ala Tyr His Gln Lys Tyr Arg
        115                 120                 125

<210> SEQ ID NO 9

```
<211> LENGTH: 185
<212> TYPE: PRT
<213> ORGANISM: Phanerochaete chrysosporium

<400> SEQUENCE: 9

Gln Ser Ala Ser Gln Phe Thr Asp Pro Thr Thr Gly Phe Gln Phe Thr
1               5                   10                  15

Gly Ile Thr Asp Pro Val His Asp Val Thr Tyr Gly Phe Val Phe Pro
            20                  25                  30

Pro Leu Ala Thr Ser Gly Ala Gln Ser Thr Glu Phe Ile Gly Glu Val
        35                  40                  45

Val Ala Pro Ile Ala Ser Lys Trp Ile Gly Ile Ala Leu Gly Gly Ala
    50                  55                  60

Met Asn Asn Asp Leu Leu Val Ala Trp Ala Asn Gly Asn Gln Ile
65                  70                  75                  80

Val Ser Ser Thr Arg Trp Ala Thr Gly Tyr Val Gln Pro Thr Ala Tyr
                85                  90                  95

Thr Gly Thr Ala Thr Leu Thr Thr Leu Pro Glu Thr Thr Ile Asn Ser
            100                 105                 110

Thr His Trp Lys Trp Val Phe Arg Cys Gln Gly Cys Thr Glu Trp Asn
        115                 120                 125

Asn Gly Gly Gly Ile Asp Val Thr Ser Gln Gly Val Leu Ala Trp Ala
    130                 135                 140

Phe Ser Asn Val Ala Val Asp Asp Pro Ser Asp Pro Gln Ser Thr Phe
145                 150                 155                 160

Ser Glu His Thr Asp Phe Gly Phe Phe Gly Ile Asp Tyr Ser Thr Asp
                165                 170                 175

Ser Ala Asn Tyr Gln Asn Tyr Leu Asn
            180                 185

<210> SEQ ID NO 10
<211> LENGTH: 2112
<212> TYPE: DNA
<213> ORGANISM: Artificial Sequence
<220> FEATURE:
<223> OTHER INFORMATION: DNA coding for fugion protein

<400> SEQUENCE: 10
gctgatcttg aagacaatat ggaaaccctc aacgacaatt taaaagtgat cgaaaaagcg      60
gataacgcgg cgcaagtcaa agacgcgtta acgaagatgc gcgccgcagc gctggatgcg     120
caaaaagcaa cgccgccgaa gctcgaagat aaatcaccgg acagcccgga atgaaagat     180
ttccgccacg gtttcgacat tctggtcggt cagattgacg acgcgctgaa gctggcaaat     240
gaaggtaaag taaagaagc gcaggctgct cagagcaac tgaaaacgac ccgcaacgcc      300
tatcaccaga agtatcgtaa cggcgactcc ggcaaccta cgaccacgag caccaagccc      360
acaagcacga gcagctcagt cacgactgga cccactgttt ctgctacacc ttatgattac      420
atcattgttg gcgctggcac tagcggtctg gtaattgcaa atcgcctgtc tgagctgaac      480
gtcactgtag ctgttatcga ggccggtgat tctggctata ataatccgaa cgtgactaac      540
ccgtccggtt acggttctgc cttcggcact gatatcgatt gggcctatca agcattaat      600
cagaaatacg caggcaacaa aactcaaact ctgcgcgcag gtaaggtgat tggtggcact      660
tccactatca atggtatggc ctacactcgc gcagaggatg tgcagatcga tgcttgggaa      720
gcgattggta tgatggctg aactgggcc aacctgtttc cgtactacaa gaaatcccag      780
actctggaaa ttcctaccac tactcaagct gaagctggcg ctacctacga tgccagctgc      840
```

```
aatggctttg acggtcctct gaaggtaggt tggctgaaca gcctgcgtga tccgaacaat      900
tttcacacta ctctgcgtga tacctacgct gcactgggtg ttccatccaa cgatgacgtc      960
aattgcggca agatggttgg ctacagccgc tatccggcta cctacgatag cgcactgaac     1020
gtgcgccatg acgcaggtcg tgcatactac tatcctattg caaaccgcac caacctgcat     1080
ctgtacccaa acactctggc tcagcgtatc acttggaagt ctaacactga tactccaact     1140
gcgaatggta tcgaggtcct gccgaacgac tctagcactc catacaccat ctatgccaat     1200
tccgaggtca tcctgagcgc tggtgccctg gcgtctccac tgctgctgga actgtctggt     1260
atcggtaatc cgtccatcct gaacgagcac aaaatctctg ttgtggtcga tctgccgacc     1320
gttggtgaga atctgcaaga ccagaccaat actggtctgg cctacaacag ctctggtaag     1380
acctccttct ctggtgccgg taccctggtg gcttacccgt ccgcagccca ggtcttcggc     1440
tctgaagtcc aaaatatctc cgcccatgtt ctgcaatccc tgcctagcta cgctgaacaa     1500
gtgtccgctg cgtccggtaa catcactaaa gccactgacc tgctggagtt cttcaaagtc     1560
caacatgacc tgattttctc taccacccac ccggtgccga tggctgagat tctgatcatt     1620
ccgtctgcaa ccagcttctc ctccgaatac tgggctctgc tgccgtttgc acgtggcagc     1680
atccacatta ctagctccgt agctggcgag ccggctgcta ttaacccgaa ctattacatg     1740
tttgactggg acatcactag ccagatcagc actgccaagt tcatccgctc cgtctttgag     1800
acttctccat ttagctcttt cgtgggctct gagaccaaac caggcctgaa cactgtaccg     1860
gctaatgcaa ccgaggcgga atggtttgaa tgggttaaga ctgcttaccg ttctaatttt     1920
cacccggtgg gtaccgcagc tatgatgcct cgtgaggttg gcggtgttgt ggattctaag     1980
ctgaaggtat acggcactgc aaacgtgcgc gtggttgatg cgtctatcct gccaatgcag     2040
gtatgtggcc atctggtgtc tacctgtac gctgtggccg aacgtgctgc agacctgatt     2100
aaggaggata tt                                                         2112
```

<210> SEQ ID NO 11
<211> LENGTH: 2358
<212> TYPE: DNA
<213> ORGANISM: Artificial Sequence
<220> FEATURE:
<223> OTHER INFORMATION: DNA coding for fugion protein

<400> SEQUENCE: 11

```
cagagtgcct cacagtttac cgaccctacc acaggattcc agttcactgg tatcaccgac       60
cctgttcatg acgtgaccta cggcttcgtt ttcccccctc tggccaccte cggagcgcaa      120
tccactgagt tcatcggaga ggttgttgcc cccatcgcat caaaatggat tggtattgcc      180
ctcggtggcg ccatgaacaa cgacctgcta cttgtggctt gggccaacgg caaccaaatt      240
gtttcctcca ctcgctgggc tactggctat gtacagccga ctgcatatac gggaactgcc      300
actttgacaa cactccctga cacaaccatc aactccacgc actggaagtg ggtcttcagg      360
tgtcagggct gcactgagtg gaacaatggc ggcggaatcg acgtcactag ccagggcgtt      420
ctggcgtggg cattctccaa cgtcgccgtc gacgacccct ccgacccgca gagtaccttc      480
agcgagcaca ccgacttcgg cttcttcgga attgactact cgaccgacag cgccaactac      540
cagaactacc ttaatggcga ctccggcaac cctacgacca cgagcaccaa gcccacaagc      600
acgagcagct cagtcacgac tggacccact gtttctaagc ttaagaacac tacgacatac      660
gactacatcg ttgtgggagg cggcacaagt ggtcttgtgg tcgcaaatcg cctttctgag      720
```

```
aaccccgatg tctccgttct tctgcttgag gccggtgctt ctgtgttcaa caacccggac    780
gtaaccaacg ctaacggtta tggattggcc tttggctcgg ccatcgactg gcagtaccag    840
tctattaacc aaagctatgc aggaggtaaa cagcaagttc tgcgtgctgg taaggccctt    900
ggaggaacca gtacaatcaa tggaatggcc tatacccgcg cagaggatgt ccagattgac    960
gtttggcaga acttggaaa cgaaggttgg acgtggaaag atctcctacc atactacctg    1020
aagagtgaaa acttgacggc ccctaccagc tctcaggttg ctgctggcgc tgcttataac    1080
cctgccgtga atggaaaaga aggtcctctc aaggtcggct ggtcgggaag cctggcctcc    1140
ggtaatctgt cagttgctct gaaccgtacg ttccaagccg ctggtgttcc atgggttgag    1200
gatgtcaatg gaggcaagat gcgtggcttc aacatctacc catccaccct cgacgttgac    1260
ctcaatgtcc gcaagatgc agcccgggca tactacttcc cttatgatga caggaagaac    1320
cttcacctgc tggagaacac cactgccaac cgccttttct ggaagaacgg ctctgctgag    1380
gaagctattg cggatggtgt cgagatcacc tccgctgatg gcaaggtcac tcgtgtgcat    1440
gcaaagaaag aggtcatcat ctctgctggt gccctgcggt ctcctctcat tctcgagctt    1500
tcaggagttg gaaacccaac catcctcaaa agaacaaca taaccccacg tgtcgatctc    1560
cccaccgttg gggagaacct ccaagaccag ttcaacaacg gcatggctgg cgaaggatac    1620
ggcgtccttg ccggtgcctc aaccgtgacc taccttcca tctccgacgt cttcggtaac    1680
gagactgact ctatcgttgc atctctccga tctcaactct ccgactacgc cgccgcgacc    1740
gtcaaggtca gcaacggcca catgaagcag gaggaccttg agcgcctcta ccagctccaa    1800
tttgacctca tcgtcaagga caaggtccct atcgccgaga tcctcttcca ccccggtggt    1860
ggaaacgccg tgtcctccga attctggggc ttgcttccct tcgcccgtgg caacatccac    1920
attagctcca atgacccgac tgctcccgcc gccatcaacc ctaactactt tatgttcgaa    1980
tgggacggca agagccaggc cggtatcgcc aagtacatca ggaagattct ccgcagcgca    2040
ccattgaaca aacttattgc gaaggaaacc aagcccggtc tctctgagat ccgccact    2100 gctgcggatg agaagtgggt tgaatggctc aaggctaact atcgttccaa cttccacccc    2160
gtcggaactg ctgccatgat gcctcgttcc attggtggcg ttgttgataa ccgtctccgg    2220
gtctatggta ccagcaatgt tcgcgtcgta gatgcgtctg tcctgcccct tccaggtttgc    2280 ggccacttgg ttagcacgct ttatgccgtt gccgagcgcg cttccgactt gattaaggag    2340
gatgcgaaga gtgcttag                                                  2358
```

<210> SEQ ID NO 12
<211> LENGTH: 31
<212> TYPE: PRT
<213> ORGANISM: Phanerochaete chrysosporium

<400> SEQUENCE: 12

Asn Gly Asp Ser Gly Asn Pro Thr Thr Thr Ser Thr Lys Pro Thr Ser
1               5                   10                  15

Thr Ser Ser Ser Val Thr Thr Gly Pro Thr Val Ser Ala Thr Pro
            20                  25                  30

<210> SEQ ID NO 13
<211> LENGTH: 705
<212> TYPE: PRT
<213> ORGANISM: Artificial Sequence
<220> FEATURE:
<223> OTHER INFORMATION: fugion protein

<400> SEQUENCE: 13

-continued

```
Met Ala Asp Leu Glu Asp Asn Met Glu Thr Leu Asn Asp Asn Leu Lys
1               5                   10                  15

Val Ile Glu Lys Ala Asp Asn Ala Ala Gln Val Lys Asp Ala Leu Thr
            20                  25                  30

Lys Met Arg Ala Ala Ala Leu Asp Ala Gln Lys Ala Thr Pro Pro Lys
        35                  40                  45

Leu Glu Asp Lys Ser Pro Asp Ser Pro Glu Met Lys Asp Phe Arg His
    50                  55                  60

Gly Phe Asp Ile Leu Val Gly Gln Ile Asp Asp Ala Leu Lys Leu Ala
65                  70                  75                  80

Asn Glu Gly Lys Val Lys Glu Ala Gln Ala Ala Glu Gln Leu Lys
                85                  90                  95

Thr Thr Arg Asn Ala Tyr His Gln Lys Tyr Arg Asn Gly Asp Ser Gly
                100                 105                 110

Asn Pro Thr Thr Thr Ser Thr Lys Pro Thr Ser Thr Ser Ser Ser Val
            115                 120                 125

Thr Thr Gly Pro Thr Val Ser Ala Thr Pro Tyr Asp Tyr Ile Ile Val
        130                 135                 140

Gly Ala Gly Thr Ser Gly Leu Val Ile Ala Asn Arg Leu Ser Glu Leu
145                 150                 155                 160

Asn Val Thr Val Ala Val Ile Glu Ala Gly Asp Ser Gly Tyr Asn Asn
                165                 170                 175

Pro Asn Val Thr Asn Pro Ser Gly Tyr Gly Ser Ala Phe Gly Thr Asp
            180                 185                 190

Ile Asp Trp Ala Tyr Gln Ser Ile Asn Gln Lys Tyr Ala Gly Asn Lys
        195                 200                 205

Thr Gln Thr Leu Arg Ala Gly Lys Val Ile Gly Gly Thr Ser Thr Ile
    210                 215                 220

Asn Gly Met Ala Tyr Thr Arg Ala Glu Asp Val Gln Ile Asp Ala Trp
225                 230                 235                 240

Glu Ala Ile Gly Asn Asp Gly Trp Asn Trp Ala Asn Leu Phe Pro Tyr
                245                 250                 255

Tyr Lys Lys Ser Gln Thr Leu Glu Ile Pro Thr Thr Thr Gln Ala Glu
            260                 265                 270

Ala Gly Ala Thr Tyr Asp Ala Ser Ala Asn Gly Phe Asp Gly Pro Leu
        275                 280                 285

Lys Val Gly Trp Leu Asn Ser Leu Glu Asp Thr Asn Asn Phe His Thr
    290                 295                 300

Thr Leu Asn Asp Thr Tyr Ala Ala Leu Gly Val Pro Ser Asn Asp Asp
305                 310                 315                 320

Val Asn Thr Gly Lys Met Val Gly Tyr Ser Arg Tyr Pro Ala Thr Tyr
                325                 330                 335

Asp Ser Ala Leu Asn Val Arg His Asp Ala Gly Arg Ala Tyr Tyr Tyr
            340                 345                 350

Pro Ile Ala Asn Arg Thr Asn Leu His Leu Tyr Pro Asn Thr Leu Ala
        355                 360                 365

Gln Arg Ile Thr Trp Lys Ser Asn Thr Asp Thr Pro Thr Ala Asn Gly
    370                 375                 380

Ile Glu Val Leu Pro Asn Asp Ser Ser Thr Pro Tyr Thr Ile Tyr Ala
385                 390                 395                 400

Asn Ser Glu Val Ile Leu Ser Ala Gly Ala Leu Ala Ser Pro Leu Leu
                405                 410                 415
```

```
Leu Glu Leu Ser Gly Ile Gly Asn Pro Ser Ile Leu Asn Glu His Asn
            420                 425                 430

Ile Ser Val Val Val Asp Leu Pro Thr Val Gly Glu Asn Leu Gln Asp
        435                 440                 445

Gln Thr Asn Thr Gly Leu Ala Tyr Asn Ser Ser Gly Asn Thr Ser Phe
    450                 455                 460

Ser Gly Ala Gly Thr Leu Val Ala Tyr Pro Ser Ala Ala Gln Val Phe
465                 470                 475                 480

Gly Ser Glu Val Gln Asn Ile Ser Ala His Val Leu Gln Ser Leu Pro
                485                 490                 495

Ser Tyr Ala Glu Gln Val Ser Ala Ala Ser Gly Asn Ile Thr Lys Ala
            500                 505                 510

Thr Asp Leu Leu Glu Phe Phe Lys Val Gln His Asp Leu Ile Phe Ser
        515                 520                 525

Thr Thr His Pro Val Pro Met Ala Glu Ile Leu Ile Ile Pro Ser Ala
    530                 535                 540

Thr Ser Phe Ser Ser Glu Tyr Trp Ala Leu Leu Pro Phe Ala Arg Gly
545                 550                 555                 560

Ser Ile His Ile Thr Ser Ser Val Ala Gly Glu Pro Ala Ala Ile Asn
                565                 570                 575

Pro Asn Tyr Tyr Met Phe Asp Trp Asp Ile Thr Ser Gln Ile Ser Thr
            580                 585                 590

Ala Lys Phe Ile Arg Ser Val Phe Glu Thr Ser Pro Phe Ser Ser Phe
        595                 600                 605

Val Gly Ser Glu Thr Lys Pro Gly Leu Asn Thr Val Ser Ala Asn Ala
    610                 615                 620

Thr Glu Ala Glu Trp Phe Asp Trp Val Lys Thr Ala Tyr Arg Ser Asn
625                 630                 635                 640

Phe His Pro Val Ser Thr Ala Ala Met Met Pro Arg Glu Val Gly Gly
                645                 650                 655

Val Val Asp Ser Lys Leu Lys Val Tyr Gly Thr Ala Asn Val Arg Val
            660                 665                 670

Val Asp Ala Ser Ile Leu Pro Met Gln Val Ser Gly His Leu Val Ser
        675                 680                 685

Thr Leu Tyr Ala Val Ala Glu Arg Ala Ala Asp Leu Ile Lys Glu Asp
    690                 695                 700

Ile
705

<210> SEQ ID NO 14
<211> LENGTH: 785
<212> TYPE: PRT
<213> ORGANISM: Artificial Sequence
<220> FEATURE:
<223> OTHER INFORMATION: fugion protein

<400> SEQUENCE: 14

Gln Ser Ala Ser Gln Phe Thr Asp Pro Thr Thr Gly Phe Gln Phe Thr
1               5                   10                  15

Gly Ile Thr Asp Pro Val His Asp Val Thr Tyr Gly Phe Val Phe Pro
            20                  25                  30

Pro Leu Ala Thr Ser Gly Ala Gln Ser Thr Glu Phe Ile Gly Glu Val
        35                  40                  45

Val Ala Pro Ile Ala Ser Lys Trp Ile Gly Ile Ala Leu Gly Gly Ala
    50                  55                  60
```

```
Met Asn Asn Asp Leu Leu Leu Val Ala Trp Ala Gly Asn Gln Ile
 65                  70                  75                  80

Val Ser Ser Thr Arg Trp Ala Thr Gly Tyr Val Gln Pro Thr Ala Tyr
             85                  90                  95

Thr Gly Thr Ala Thr Leu Thr Thr Leu Pro Glu Thr Thr Ile Asn Ser
            100                 105                 110

Thr His Trp Lys Trp Val Phe Arg Cys Gln Gly Cys Thr Glu Trp Asn
            115                 120                 125

Asn Gly Gly Ile Asp Val Thr Ser Gln Gly Val Leu Ala Trp Ala
130                 135                 140

Phe Ser Asn Val Ala Val Asp Asp Pro Ser Asp Pro Gln Ser Thr Phe
145                 150                 155                 160

Ser Glu His Thr Asp Phe Gly Phe Phe Gly Ile Asp Tyr Ser Thr Asp
                165                 170                 175

Ser Ala Asn Tyr Gln Asn Tyr Leu Asn Gly Asp Ser Gly Asn Pro Thr
                180                 185                 190

Thr Thr Ser Thr Lys Pro Thr Ser Thr Ser Ser Val Thr Thr Gly
            195                 200                 205

Pro Thr Val Ser Lys Leu Lys Asn Thr Thr Tyr Asp Tyr Ile Val
210                 215                 220

Val Gly Gly Gly Thr Ser Gly Leu Val Val Ala Asn Arg Leu Ser Glu
225                 230                 235                 240

Asn Pro Asp Val Ser Val Leu Leu Glu Ala Gly Ala Ser Val Phe
                245                 250                 255

Asn Asn Pro Asp Val Thr Asn Ala Asn Gly Tyr Gly Leu Ala Phe Gly
            260                 265                 270

Ser Ala Ile Asp Trp Gln Tyr Gln Ser Ile Asn Gln Ser Tyr Ala Gly
            275                 280                 285

Gly Lys Gln Gln Val Leu Arg Ala Gly Lys Ala Leu Gly Gly Thr Ser
            290                 295                 300

Thr Ile Asn Gly Met Ala Tyr Thr Arg Ala Glu Asp Val Gln Ile Asp
305                 310                 315                 320

Val Trp Gln Lys Leu Gly Asn Glu Gly Trp Thr Trp Lys Asp Leu Leu
                325                 330                 335

Pro Tyr Tyr Leu Lys Ser Glu Asn Leu Thr Ala Pro Thr Ser Ser Gln
                340                 345                 350

Val Ala Ala Gly Ala Ala Tyr Asn Pro Ala Val Asn Gly Lys Glu Gly
            355                 360                 365

Pro Leu Lys Val Gly Trp Ser Gly Ser Leu Ala Ser Gly Asn Leu Ser
            370                 375                 380

Val Ala Leu Asn Arg Thr Phe Gln Ala Ala Gly Val Pro Trp Val Glu
385                 390                 395                 400

Asp Val Asn Gly Gly Lys Met Arg Gly Phe Asn Ile Tyr Pro Ser Thr
                405                 410                 415

Leu Asp Val Asp Leu Asn Val Arg Glu Asp Ala Ala Arg Ala Tyr Tyr
                420                 425                 430

Phe Pro Tyr Asp Asp Arg Lys Asn Leu His Leu Leu Glu Asn Thr Thr
                435                 440                 445

Ala Asn Arg Leu Phe Trp Lys Asn Gly Ser Ala Glu Glu Ala Ile Ala
            450                 455                 460

Asp Gly Val Glu Ile Thr Ser Ala Asp Gly Lys Val Thr Arg Val His
465                 470                 475                 480

Ala Lys Lys Glu Val Ile Ile Ser Ala Gly Ala Leu Arg Ser Pro Leu
```

-continued

```
                485                 490                 495
Ile Leu Glu Leu Ser Gly Val Gly Asn Pro Thr Ile Leu Lys Lys Asn
            500                 505                 510
Asn Ile Thr Pro Arg Val Asp Leu Pro Thr Val Gly Glu Asn Leu Gln
        515                 520                 525
Asp Gln Phe Asn Asn Gly Met Ala Gly Lys Gly Tyr Gly Val Leu Ala
    530                 535                 540
Gly Ala Ser Thr Val Thr Tyr Pro Ser Ile Ser Asp Val Phe Gly Asn
545                 550                 555                 560
Glu Thr Asp Ser Ile Val Ala Ser Leu Arg Ser Gln Leu Ser Asp Tyr
                565                 570                 575
Ala Ala Ala Thr Val Lys Val Ser Asn Gly His Met Lys Gln Glu Asp
            580                 585                 590
Leu Glu Arg Leu Tyr Gln Leu Gln Phe Asp Leu Ile Val Lys Asp Lys
        595                 600                 605
Val Pro Ile Ala Glu Ile Leu Phe His Pro Gly Gly Gly Asn Ala Val
    610                 615                 620
Ser Ser Glu Phe Trp Gly Leu Leu Pro Phe Ala Arg Gly Asn Ile His
625                 630                 635                 640
Ile Ser Ser Asn Asp Pro Thr Ala Pro Ala Ala Ile Asn Pro Asn Tyr
                645                 650                 655
Phe Met Phe Glu Trp Asp Gly Lys Ser Gln Ala Gly Ile Ala Lys Tyr
            660                 665                 670
Ile Arg Lys Ile Leu Arg Ser Ala Pro Leu Asn Lys Leu Ile Ala Lys
        675                 680                 685
Glu Thr Lys Pro Gly Leu Ser Glu Ile Pro Ala Thr Ala Ala Asp Glu
    690                 695                 700
Lys Trp Val Glu Trp Leu Lys Ala Asn Tyr Arg Ser Asn Phe His Pro
705                 710                 715                 720
Val Gly Thr Ala Ala Met Met Pro Arg Ser Ile Gly Gly Val Val Asp
                725                 730                 735
Asn Arg Leu Arg Val Tyr Gly Thr Ser Asn Val Arg Val Val Asp Ala
            740                 745                 750
Ser Val Leu Pro Phe Gln Val Cys Gly His Leu Val Ser Thr Leu Tyr
        755                 760                 765
Ala Val Ala Glu Arg Ala Ser Asp Leu Ile Lys Glu Asp Ala Lys Ser
    770                 775                 780
Ala
785

<210> SEQ ID NO 15
<211> LENGTH: 785
<212> TYPE: PRT
<213> ORGANISM: Artificial Sequence
<220> FEATURE:
<223> OTHER INFORMATION: fugion protein

<400> SEQUENCE: 15

Gln Ser Ala Ser Gln Phe Thr Asp Pro Thr Thr Gly Phe Gln Phe Thr
1               5                   10                  15
Gly Ile Thr Asp Pro Val His Asp Val Thr Tyr Gly Phe Val Phe Pro
                20                  25                  30
Pro Leu Ala Thr Ser Gly Ala Gln Ser Thr Glu Phe Ile Gly Glu Val
            35                  40                  45
Val Ala Pro Ile Ala Ser Lys Trp Ile Gly Ile Ala Leu Gly Gly Ala
```

-continued

```
             50                  55                  60
Met Asn Asp Leu Leu Leu Val Ala Trp Ala Asn Gly Asn Gln Ile
 65                      70                  75                  80

Val Ser Ser Thr Arg Trp Ala Thr Gly Tyr Val Gln Pro Thr Ala Tyr
                     85                  90                  95

Thr Gly Thr Ala Thr Leu Thr Thr Leu Pro Glu Thr Thr Ile Asn Ser
                    100                 105                 110

Thr His Trp Lys Trp Val Phe Arg Cys Gln Gly Cys Thr Glu Trp Asn
                115                 120                 125

Asn Gly Gly Gly Ile Asp Val Thr Ser Gln Gly Val Leu Ala Trp Ala
            130                 135                 140

Phe Ser Asn Val Ala Val Asp Asp Pro Ser Asp Pro Gln Ser Thr Phe
145                 150                 155                 160

Ser Glu His Thr Asp Phe Gly Phe Phe Gly Ile Asp Tyr Ser Thr Asp
                165                 170                 175

Ser Ala Asn Tyr Gln Asn Tyr Leu Asn Gly Asp Ser Gly Asn Pro Thr
                180                 185                 190

Thr Thr Ser Thr Lys Pro Thr Ser Thr Ser Ser Val Thr Thr Gly
                195                 200                 205

Pro Thr Val Ser Lys Leu Lys Asn Thr Thr Thr Tyr Asp Tyr Ile Val
    210                 215                 220

Val Gly Gly Gly Thr Ser Gly Leu Val Val Ala Asn Arg Leu Ser Glu
225                 230                 235                 240

Asn Pro Asp Val Ser Val Leu Leu Glu Ala Gly Ala Ser Val Phe
                    245                 250                 255

Asn Asn Pro Asp Val Thr Asn Ala Asn Gly Tyr Gly Leu Ala Phe Gly
                260                 265                 270

Ser Ala Ile Asp Trp Gln Tyr Gln Ser Ile Asn Gln Ser Tyr Ala Gly
            275                 280                 285

Gly Lys Gln Gln Val Leu Arg Ala Gly Lys Ala Leu Gly Gly Thr Ser
    290                 295                 300

Thr Ile Asn Gly Met Ala Tyr Thr Arg Ala Glu Asp Val Gln Ile Asp
305                 310                 315                 320

Val Trp Gln Lys Leu Gly Asn Glu Gly Trp Thr Trp Lys Asp Leu Leu
                325                 330                 335

Pro Tyr Tyr Leu Lys Ser Glu Asn Leu Thr Ala Pro Thr Ser Ser Gln
                340                 345                 350

Val Ala Ala Gly Ala Ala Tyr Asn Pro Ala Val Asn Gly Lys Glu Gly
            355                 360                 365

Pro Leu Lys Val Gly Trp Ser Gly Ser Leu Ala Ser Gly Asn Leu Ser
    370                 375                 380

Val Ala Leu Asn Arg Thr Phe Gln Ala Ala Gly Val Pro Trp Val Glu
385                 390                 395                 400

Asp Val Asn Gly Gly Lys Met Arg Gly Phe Asn Ile Tyr Pro Ser Thr
                405                 410                 415

Leu Asp Val Asp Leu Asn Val Arg Glu Asp Ala Ala Arg Ala Tyr Tyr
                420                 425                 430

Phe Pro Tyr Asp Asp Arg Lys Asn Leu His Leu Leu Glu Asn Thr Thr
                435                 440                 445

Ala Asn Arg Leu Phe Trp Lys Asn Gly Ser Ala Glu Glu Ala Ile Ala
    450                 455                 460

Asp Gly Val Glu Ile Thr Ser Ala Asp Gly Lys Val Thr Arg Val His
465                 470                 475                 480
```

Ala Lys Lys Glu Val Ile Ile Ser Ala Gly Ala Leu Arg Ser Pro Leu
                485                 490                 495

Ile Leu Glu Leu Ser Gly Val Gly Asn Pro Thr Ile Leu Lys Lys Asn
                500                 505                 510

Asn Ile Thr Pro Arg Val Asp Leu Pro Thr Val Gly Glu Asn Leu Gln
                515                 520                 525

Asp Gln Phe Asn Asn Gly Met Ala Gly Arg Gly Tyr Gly Val Leu Ala
                530                 535                 540

Gly Ala Ser Thr Val Thr Tyr Pro Ser Ile Ser Asp Val Phe Gly Asn
545                 550                 555                 560

Glu Thr Asp Ser Ile Val Ala Ser Leu Arg Ser Gln Leu Ser Asp Tyr
                565                 570                 575

Ala Ala Ala Thr Val Lys Val Ser Asn Gly His Met Lys Gln Glu Asp
                580                 585                 590

Leu Glu Arg Leu Tyr Gln Leu Gln Phe Asp Leu Ile Val Lys Asp Lys
                595                 600                 605

Val Pro Ile Ala Glu Ile Leu Phe His Pro Gly Gly Gly Asn Ala Val
                610                 615                 620

Ser Ser Glu Phe Trp Gly Leu Leu Pro Phe Ala Arg Gly Asn Ile His
625                 630                 635                 640

Ile Ser Ser Asn Asp Pro Thr Ala Pro Ala Ile Asn Pro Asn Tyr
                645                 650                 655

Phe Met Phe Glu Trp Asp Gly Lys Ser Gln Ala Gly Ile Ala Lys Tyr
                660                 665                 670

Ile Arg Lys Ile Leu Arg Ser Ala Pro Leu Asn Lys Leu Ile Ala Lys
                675                 680                 685

Glu Thr Lys Pro Gly Leu Ser Glu Ile Pro Ala Thr Ala Ala Asp Glu
                690                 695                 700

Lys Trp Val Glu Trp Leu Lys Ala Asn Tyr Arg Ser Asn Phe His Pro
705                 710                 715                 720

Val Gly Thr Ala Ala Met Met Pro Arg Ser Ile Gly Gly Val Asp
                725                 730                 735

Asn Arg Leu Arg Val Tyr Gly Thr Ser Asn Val Arg Val Asp Ala
                740                 745                 750

Ser Val Leu Pro Phe Gln Val Cys Gly His Leu Val Ser Thr Leu Tyr
                755                 760                 765

Ala Val Ala Glu Arg Ala Ser Asp Leu Ile Lys Glu Asp Ala Lys Ser
                770                 775                 780

Ala
785

<210> SEQ ID NO 16
<211> LENGTH: 785
<212> TYPE: PRT
<213> ORGANISM: Artificial Sequence
<220> FEATURE:
<223> OTHER INFORMATION: fugion protein

<400> SEQUENCE: 16

Gln Ser Ala Ser Gln Phe Thr Asp Pro Thr Gly Phe Gln Phe Thr
1               5                   10                  15

Gly Ile Thr Asp Pro Val His Asp Val Thr Tyr Gly Phe Val Phe Pro
                20                  25                  30

Pro Leu Ala Thr Ser Gly Ala Gln Ser Thr Glu Phe Ile Gly Glu Val
                35                  40                  45

-continued

```
Val Ala Pro Ile Ala Ser Lys Trp Ile Gly Ile Ala Leu Gly Gly Ala
 50              55                  60

Met Asn Asn Asp Leu Leu Val Ala Trp Ala Asn Gly Asn Gln Ile
 65                  70                  75                  80

Val Ser Ser Thr Arg Trp Ala Thr Gly Tyr Val Gln Pro Thr Ala Tyr
                 85                  90                  95

Thr Gly Thr Ala Thr Leu Thr Thr Leu Pro Glu Thr Thr Ile Asn Ser
            100                 105                 110

Thr His Trp Lys Trp Val Phe Arg Cys Gln Gly Cys Thr Glu Trp Asn
            115                 120                 125

Asn Gly Gly Ile Asp Val Thr Ser Gln Gly Val Leu Ala Trp Ala
130                 135                 140

Phe Ser Asn Val Ala Val Asp Asp Pro Ser Asp Pro Gln Ser Thr Phe
145                 150                 155                 160

Ser Glu His Thr Asp Phe Gly Phe Phe Gly Ile Asp Tyr Ser Thr Asp
                165                 170                 175

Ser Ala Asn Tyr Gln Asn Tyr Leu Asn Gly Asp Ser Gly Asn Pro Thr
            180                 185                 190

Thr Thr Ser Thr Lys Pro Thr Ser Thr Ser Ser Val Thr Thr Gly
            195                 200                 205

Pro Thr Val Ser Lys Leu Lys Asn Thr Thr Tyr Asp Tyr Ile Val
210                 215                 220

Val Gly Gly Gly Thr Ser Gly Leu Val Val Ala Asn Arg Leu Ser Glu
225                 230                 235                 240

Asn Pro Asp Val Ser Val Leu Leu Glu Ala Gly Ala Ser Val Phe
                245                 250                 255

Asn Asn Pro Asp Val Thr Asn Ala Asn Gly Tyr Gly Leu Ala Phe Gly
            260                 265                 270

Ser Ala Ile Asp Trp Gln Tyr Gln Ser Ile Asn Gln Ser Tyr Ala Gly
            275                 280                 285

Gly Lys Gln Gln Val Leu Arg Ala Gly Lys Ala Leu Gly Gly Thr Ser
290                 295                 300

Thr Ile Asn Gly Met Ala Tyr Thr Arg Ala Glu Asp Val Gln Ile Asp
305                 310                 315                 320

Val Trp Gln Lys Leu Gly Asn Glu Gly Trp Thr Trp Lys Asp Leu Leu
                325                 330                 335

Pro Tyr Tyr Leu Lys Ser Glu Asn Leu Thr Ala Pro Thr Ser Ser Gln
            340                 345                 350

Val Ala Ala Gly Ala Ala Tyr Asn Pro Ala Val Asn Gly Lys Glu Gly
            355                 360                 365

Pro Leu Lys Val Gly Trp Ser Gly Ser Leu Ala Ser Gly Asn Leu Ser
370                 375                 380

Val Ala Leu Asn Arg Thr Phe Gln Ala Ala Gly Val Pro Trp Val Glu
385                 390                 395                 400

Asp Val Asn Gly Gly Lys Met Arg Gly Phe Asn Ile Tyr Pro Ser Thr
                405                 410                 415

Leu Asp Val Asp Leu Asn Val Arg Glu Asp Ala Ala Arg Ala Tyr Tyr
            420                 425                 430

Phe Pro Tyr Asp Asp Arg Lys Asn Leu His Leu Leu Glu Asn Thr Thr
            435                 440                 445

Ala Asn Arg Leu Phe Trp Lys Asn Gly Ser Ala Glu Glu Ala Ile Ala
450                 455                 460
```

```
Asp Gly Val Glu Ile Thr Ser Ala Asp Gly Lys Val Thr Arg Val His
465                 470                 475                 480

Ala Lys Lys Glu Val Ile Ser Ala Gly Ala Leu Arg Ser Pro Leu
                485                 490                 495

Ile Leu Glu Leu Ser Gly Val Gly Asn Pro Thr Ile Leu Lys Lys Asn
            500                 505                 510

Asn Ile Thr Pro Arg Val Asp Leu Pro Thr Val Gly Glu Asn Leu Gln
            515                 520                 525

Asp Gln Phe Asn Asn Gly Met Ala Gly Glu Gly Tyr Gly Val Leu Ala
530                 535                 540

Gly Ala Ser Thr Val Thr Tyr Pro Ser Ile Ser Asp Val Phe Gly Asn
545                 550                 555                 560

Glu Thr Asp Ser Ile Val Ala Ser Leu Arg Ser Gln Leu Ser Asp Tyr
                565                 570                 575

Ala Ala Ala Thr Val Lys Val Ser Asn Gly His Met Lys Gln Glu Asp
            580                 585                 590

Leu Glu Arg Leu Tyr Gln Leu Gln Phe Asp Leu Ile Val Lys Asp Lys
            595                 600                 605

Val Pro Ile Ala Glu Ile Leu Phe His Pro Gly Gly Lys Ala Val
610                 615                 620

Ser Glu Phe Trp Gly Leu Leu Pro Phe Ala Arg Gly Asn Ile His
625                 630                 635                 640

Ile Ser Ser Asn Asp Pro Thr Ala Pro Ala Ala Ile Asn Pro Asn Tyr
                645                 650                 655

Phe Met Phe Glu Trp Asp Gly Lys Ser Gln Ala Gly Ile Ala Lys Tyr
            660                 665                 670

Ile Arg Lys Ile Leu Arg Ser Ala Pro Leu Asn Lys Leu Ile Ala Lys
            675                 680                 685

Glu Thr Lys Pro Gly Leu Ser Glu Ile Pro Ala Thr Ala Ala Asp Glu
690                 695                 700

Lys Trp Val Glu Trp Leu Lys Ala Asn Tyr Arg Ser Asn Phe His Pro
705                 710                 715                 720

Val Gly Thr Ala Ala Met Met Pro Arg Ser Ile Gly Gly Val Val Asp
                725                 730                 735

Asn Arg Leu Arg Val Tyr Gly Thr Ser Asn Val Arg Val Val Asp Ala
            740                 745                 750

Ser Val Leu Pro Phe Gln Val Cys Gly His Leu Val Ser Thr Leu Tyr
            755                 760                 765

Ala Val Ala Glu Arg Ala Ser Asp Leu Ile Lys Glu Asp Ala Lys Ser
        770                 775                 780

Ala
785

<210> SEQ ID NO 17
<211> LENGTH: 785
<212> TYPE: PRT
<213> ORGANISM: Artificial Sequence
<220> FEATURE:
<223> OTHER INFORMATION: fugion protein

<400> SEQUENCE: 17

Gln Ser Ala Ser Gln Phe Thr Asp Pro Thr Thr Gly Phe Gln Phe Thr
1               5                   10                  15

Gly Ile Thr Asp Pro Val His Asp Val Thr Tyr Gly Phe Val Phe Pro
            20                  25                  30
```

```
Pro Leu Ala Thr Ser Gly Ala Gln Ser Thr Glu Phe Ile Gly Glu Val
        35                  40                  45

Val Ala Pro Ile Ala Ser Lys Trp Ile Gly Ile Ala Leu Gly Gly Ala
50                  55                  60

Met Asn Asn Asp Leu Leu Leu Val Ala Trp Ala Asn Gly Asn Gln Ile
65                  70                  75                  80

Val Ser Ser Thr Arg Trp Ala Thr Gly Tyr Val Gln Pro Thr Ala Tyr
                85                  90                  95

Thr Gly Thr Ala Thr Leu Thr Thr Leu Pro Glu Thr Thr Ile Asn Ser
                100                 105                 110

Thr His Trp Lys Trp Val Phe Arg Cys Gln Gly Cys Thr Glu Trp Asn
                115                 120                 125

Asn Gly Gly Gly Ile Asp Val Thr Ser Gln Gly Val Leu Ala Trp Ala
                130                 135                 140

Phe Ser Asn Val Ala Val Asp Asp Pro Ser Asp Pro Gln Ser Thr Phe
145                 150                 155                 160

Ser Glu His Thr Asp Phe Gly Phe Phe Gly Ile Asp Tyr Ser Thr Asp
                165                 170                 175

Ser Ala Asn Tyr Gln Asn Tyr Leu Asn Gly Asp Ser Gly Asn Pro Thr
                180                 185                 190

Thr Thr Ser Thr Lys Pro Thr Ser Thr Ser Ser Val Thr Thr Gly
                195                 200                 205

Pro Thr Val Ser Lys Leu Lys Asn Thr Thr Thr Tyr Asp Tyr Ile Val
    210                 215                 220

Val Gly Gly Gly Thr Ser Gly Leu Val Val Ala Asn Arg Leu Ser Glu
225                 230                 235                 240

Asn Pro Asp Val Ser Val Leu Leu Glu Ala Gly Ala Ser Val Phe
                245                 250                 255

Asn Asn Pro Asp Val Thr Asn Ala Asn Gly Tyr Gly Leu Ala Phe Gly
                260                 265                 270

Ser Ala Ile Asp Trp Gln Tyr Gln Ser Ile Asn Gln Ser Tyr Ala Gly
                275                 280                 285

Gly Lys Gln Gln Val Leu Arg Ala Gly Lys Ala Leu Gly Gly Thr Ser
    290                 295                 300

Thr Ile Asn Gly Met Ala Tyr Thr Arg Ala Glu Asp Val Gln Ile Asp
305                 310                 315                 320

Val Trp Gln Lys Leu Gly Asn Glu Gly Trp Thr Trp Lys Asp Leu Leu
                325                 330                 335

Pro Tyr Tyr Leu Lys Ser Glu Asn Leu Thr Ala Pro Thr Ser Ser Gln
                340                 345                 350

Val Ala Ala Gly Ala Ala Tyr Asn Pro Ala Val Asn Gly Lys Glu Gly
                355                 360                 365

Pro Leu Lys Val Gly Trp Ser Gly Ser Leu Ala Ser Gly Asn Leu Ser
    370                 375                 380

Val Ala Leu Asn Arg Thr Phe Gln Ala Ala Gly Val Pro Trp Val Glu
385                 390                 395                 400

Asp Val Asn Gly Gly Lys Met Arg Gly Phe Asn Ile Tyr Pro Ser Thr
                405                 410                 415

Leu Asp Val Asp Leu Asn Val Arg Glu Asp Ala Ala Arg Ala Tyr Tyr
                420                 425                 430

Phe Pro Tyr Asp Asp Arg Lys Asn Leu His Leu Leu Glu Asn Thr Thr
                435                 440                 445

Ala Asn Arg Leu Phe Trp Lys Asn Gly Ser Ala Glu Glu Ala Ile Ala
```

```
                450             455             460
Asp Gly Val Glu Ile Thr Ser Ala Asp Gly Lys Val Thr Arg Val His
465                 470                 475                 480

Ala Lys Lys Glu Val Ile Ile Ser Ala Gly Ala Leu Arg Ser Pro Leu
                485                 490                 495

Ile Leu Glu Leu Ser Gly Val Gly Asn Pro Thr Ile Leu Lys Lys Asn
                500                 505                 510

Asn Ile Thr Pro Arg Val Asp Leu Pro Thr Val Gly Glu Asn Leu Gln
                515                 520                 525

Asp Gln Phe Asn Asn Gly Met Ala Gly Glu Gly Tyr Gly Val Leu Ala
            530                 535                 540

Gly Ala Ser Thr Val Thr Tyr Pro Ser Ile Ser Asp Val Phe Gly Asn
545                 550                 555                 560

Glu Thr Asp Ser Ile Val Ala Ser Leu Arg Ser Gln Leu Ser Asp Tyr
                565                 570                 575

Ala Ala Ala Thr Val Lys Val Ser Asn Gly His Met Lys Gln Glu Asp
            580                 585                 590

Leu Glu Arg Leu Tyr Gln Leu Gln Phe Asp Leu Ile Val Lys Asp Lys
            595                 600                 605

Val Pro Ile Ala Glu Ile Leu Phe His Pro Gly Gly Arg Ala Val
610                 615                 620

Ser Ser Glu Phe Trp Gly Leu Leu Pro Phe Ala Arg Gly Asn Ile His
625                 630                 635                 640

Ile Ser Ser Asn Asp Pro Thr Ala Pro Ala Ile Asn Pro Asn Tyr
            645                 650                 655

Phe Met Phe Glu Trp Asp Gly Lys Ser Gln Ala Gly Ile Ala Lys Tyr
                660                 665                 670

Ile Arg Lys Ile Leu Arg Ser Ala Pro Leu Asn Lys Leu Ile Ala Lys
            675                 680                 685

Glu Thr Lys Pro Gly Leu Ser Glu Ile Pro Ala Thr Ala Ala Asp Glu
            690                 695                 700

Lys Trp Val Glu Trp Leu Lys Ala Asn Tyr Arg Ser Asn Phe His Pro
705                 710                 715                 720

Val Gly Thr Ala Ala Met Met Pro Arg Ser Ile Gly Gly Val Val Asp
                725                 730                 735

Asn Arg Leu Arg Val Tyr Gly Thr Ser Asn Val Arg Val Val Asp Ala
            740                 745                 750

Ser Val Leu Pro Phe Gln Val Cys Gly His Leu Val Ser Thr Leu Tyr
            755                 760                 765

Ala Val Ala Glu Arg Ala Ser Asp Leu Ile Lys Glu Asp Ala Lys Ser
            770                 775                 780

Ala
785

<210> SEQ ID NO 18
<211> LENGTH: 785
<212> TYPE: PRT
<213> ORGANISM: Artificial Sequence
<220> FEATURE:
<223> OTHER INFORMATION: fugion protein

<400> SEQUENCE: 18

Gln Ser Ala Ser Gln Phe Thr Asp Pro Thr Thr Gly Phe Gln Phe Thr
1               5                   10                  15

Gly Ile Thr Asp Pro Val His Asp Val Thr Tyr Gly Phe Val Phe Pro
```

20                  25                  30
Pro Leu Ala Thr Ser Gly Ala Gln Ser Thr Glu Phe Ile Gly Glu Val
                35                  40                  45
Val Ala Pro Ile Ala Ser Lys Trp Ile Gly Ile Ala Leu Gly Gly Ala
 50                  55                  60
Met Asn Asn Asp Leu Leu Val Ala Trp Ala Asn Gly Asn Gln Ile
 65                  70                  75                  80
Val Ser Ser Thr Arg Trp Ala Thr Gly Tyr Val Gln Pro Thr Ala Tyr
                85                  90                  95
Thr Gly Thr Ala Thr Leu Thr Thr Leu Pro Glu Thr Thr Ile Asn Ser
                100                 105                 110
Thr His Trp Lys Trp Val Phe Arg Cys Gln Gly Cys Thr Glu Trp Asn
                115                 120                 125
Asn Gly Gly Ile Asp Val Thr Ser Gln Gly Val Leu Ala Trp Ala
 130                 135                 140
Phe Ser Asn Val Ala Val Asp Asp Pro Ser Asp Pro Gln Ser Thr Phe
 145                 150                 155                 160
Ser Glu His Thr Asp Phe Gly Phe Phe Gly Ile Asp Tyr Ser Thr Asp
                165                 170                 175
Ser Ala Asn Tyr Gln Asn Tyr Leu Asn Gly Asp Ser Gly Asn Pro Thr
                180                 185                 190
Thr Thr Ser Thr Lys Pro Thr Ser Thr Ser Ser Val Thr Thr Gly
                195                 200                 205
Pro Thr Val Ser Lys Leu Lys Asn Thr Thr Thr Tyr Asp Tyr Ile Val
 210                 215                 220
Val Gly Gly Gly Thr Ser Gly Leu Val Val Ala Asn Arg Leu Ser Glu
 225                 230                 235                 240
Asn Pro Asp Val Ser Val Leu Leu Glu Ala Gly Ala Ser Val Phe
                245                 250                 255
Asn Asn Pro Asp Val Thr Asn Ala Asn Gly Tyr Gly Leu Ala Phe Gly
                260                 265                 270
Ser Ala Ile Asp Trp Gln Tyr Gln Ser Ile Asn Gln Ser Tyr Ala Gly
                275                 280                 285
Gly Lys Gln Gln Val Leu Arg Ala Gly Lys Ala Leu Gly Gly Thr Ser
                290                 295                 300
Thr Ile Asn Gly Met Ala Tyr Thr Arg Ala Glu Asp Val Gln Ile Asp
 305                 310                 315                 320
Val Trp Gln Lys Leu Gly Asn Glu Gly Trp Thr Trp Lys Asp Leu Leu
                325                 330                 335
Pro Tyr Tyr Leu Lys Ser Glu Asn Leu Thr Ala Pro Thr Ser Ser Gln
                340                 345                 350
Val Ala Ala Gly Ala Ala Tyr Asn Pro Ala Val Asn Gly Lys Glu Gly
                355                 360                 365
Pro Leu Lys Val Gly Trp Ser Gly Ser Leu Ala Ser Gly Asn Leu Ser
                370                 375                 380
Val Ala Leu Asn Arg Thr Phe Gln Ala Ala Gly Val Pro Trp Val Glu
 385                 390                 395                 400
Asp Val Asn Gly Gly Lys Met Arg Gly Phe Asn Ile Tyr Pro Ser Thr
                405                 410                 415
Leu Asp Val Asp Leu Asn Val Arg Glu Asp Ala Ala Arg Ala Tyr Tyr
                420                 425                 430
Phe Pro Tyr Asp Asp Arg Lys Asn Leu His Leu Leu Glu Asn Thr Thr
                435                 440                 445

```
Ala Asn Arg Leu Phe Trp Lys Asn Gly Ser Ala Glu Glu Ala Ile Ala
    450                 455                 460

Asp Gly Val Glu Ile Thr Ser Ala Asp Gly Lys Val Thr Arg Val His
465                 470                 475                 480

Ala Lys Lys Glu Val Ile Ile Ser Ala Gly Ala Leu Arg Ser Pro Leu
                485                 490                 495

Ile Leu Glu Leu Ser Gly Val Gly Asn Pro Thr Ile Leu Lys Lys Asn
            500                 505                 510

Asn Ile Thr Pro Arg Val Asp Leu Pro Thr Val Gly Glu Asn Leu Gln
        515                 520                 525

Asp Gln Phe Asn Asn Gly Met Ala Gly Glu Gly Tyr Gly Val Leu Ala
    530                 535                 540

Gly Ala Ser Thr Val Thr Tyr Pro Ser Ile Ser Asp Val Phe Gly Asn
545                 550                 555                 560

Glu Thr Asp Ser Ile Val Ala Ser Leu Arg Ser Gln Leu Ser Asp Tyr
                565                 570                 575

Ala Ala Ala Thr Val Lys Val Ser Asn Gly His Met Lys Gln Glu Asp
            580                 585                 590

Leu Glu Arg Leu Tyr Gln Leu Gln Phe Asp Leu Ile Val Lys Asp Lys
        595                 600                 605

Val Pro Ile Ala Glu Ile Leu Phe His Pro Gly Gly Gly Asn Ala Val
    610                 615                 620

Ser Ser Glu Phe Trp Gly Leu Leu Pro Phe Ala Arg Gly Asn Ile His
625                 630                 635                 640

Ile Ser Ser Asn Asp Pro Thr Ala Pro Ala Ala Ile Asn Pro Asn Tyr
                645                 650                 655

Phe Met Phe Glu Trp Asp Gly Lys Ser Gln Ala Gly Ile Ala Lys Tyr
            660                 665                 670

Ile Arg Lys Ile Leu Arg Ser Ala Pro Leu Asn Lys Leu Ile Ala Lys
        675                 680                 685

Glu Lys Lys Pro Gly Leu Ser Glu Ile Pro Ala Thr Ala Ala Asp Glu
    690                 695                 700

Lys Trp Val Glu Trp Leu Lys Ala Asn Tyr Arg Ser Asn Phe His Pro
705                 710                 715                 720

Val Gly Thr Ala Ala Met Met Pro Arg Ser Ile Gly Gly Val Val Asp
                725                 730                 735

Asn Arg Leu Arg Val Tyr Gly Thr Ser Asn Val Arg Val Val Asp Ala
            740                 745                 750

Ser Val Leu Pro Phe Gln Val Cys Gly His Leu Val Ser Thr Leu Tyr
        755                 760                 765

Ala Val Ala Glu Arg Ala Ser Asp Leu Ile Lys Glu Asp Ala Lys Ser
    770                 775                 780

Ala
785

<210> SEQ ID NO 19
<211> LENGTH: 785
<212> TYPE: PRT
<213> ORGANISM: Artificial Sequence
<220> FEATURE:
<223> OTHER INFORMATION: fugion protein

<400> SEQUENCE: 19

Gln Ser Ala Ser Gln Phe Thr Asp Pro Thr Thr Gly Phe Gln Phe Thr
1               5                   10                  15
```

```
Gly Ile Thr Asp Pro Val His Asp Val Thr Tyr Gly Phe Val Phe Pro
             20                  25                  30

Pro Leu Ala Thr Ser Gly Ala Gln Ser Thr Glu Phe Ile Gly Glu Val
             35                  40                  45

Val Ala Pro Ile Ala Ser Lys Trp Ile Gly Ile Ala Leu Gly Gly Ala
 50                  55                  60

Met Asn Asp Leu Leu Leu Val Ala Trp Ala Asn Gly Asn Gln Ile
 65                  70                  75                  80

Val Ser Ser Thr Arg Trp Ala Thr Gly Tyr Val Gln Pro Thr Ala Tyr
                 85                  90                  95

Thr Gly Thr Ala Thr Leu Thr Thr Leu Pro Glu Thr Thr Ile Asn Ser
                100                 105                 110

Thr His Trp Lys Trp Val Phe Arg Cys Gln Gly Cys Thr Glu Trp Asn
             115                 120                 125

Asn Gly Gly Gly Ile Asp Val Thr Ser Gln Gly Val Leu Ala Trp Ala
             130                 135                 140

Phe Ser Asn Val Ala Val Asp Asp Pro Ser Asp Pro Gln Ser Thr Phe
145                 150                 155                 160

Ser Glu His Thr Asp Phe Gly Phe Phe Gly Ile Asp Tyr Ser Thr Asp
                 165                 170                 175

Ser Ala Asn Tyr Gln Asn Tyr Leu Asn Gly Asp Ser Gly Asn Pro Thr
             180                 185                 190

Thr Thr Ser Thr Lys Pro Thr Ser Thr Ser Ser Val Thr Thr Gly
             195                 200                 205

Pro Thr Val Ser Lys Leu Lys Asn Thr Thr Thr Tyr Asp Tyr Ile Val
     210                 215                 220

Val Gly Gly Gly Thr Ser Gly Leu Val Val Ala Asn Arg Leu Ser Glu
225                 230                 235                 240

Asn Pro Asp Val Ser Val Leu Leu Glu Ala Gly Ala Ser Val Phe
             245                 250                 255

Asn Asn Pro Asp Val Thr Asn Ala Asn Gly Tyr Gly Leu Ala Phe Gly
             260                 265                 270

Ser Ala Ile Asp Trp Gln Tyr Gln Ser Ile Asn Gln Ser Tyr Ala Gly
             275                 280                 285

Gly Lys Gln Gln Val Leu Arg Ala Gly Lys Ala Leu Gly Gly Thr Ser
     290                 295                 300

Thr Ile Asn Gly Met Ala Tyr Thr Arg Ala Glu Asp Val Gln Ile Asp
305                 310                 315                 320

Val Trp Gln Lys Leu Gly Asn Glu Gly Trp Thr Trp Lys Asp Leu Leu
                 325                 330                 335

Pro Tyr Tyr Leu Lys Ser Glu Asn Leu Thr Ala Pro Thr Ser Ser Gln
             340                 345                 350

Val Ala Ala Gly Ala Ala Tyr Asn Pro Ala Val Asn Gly Lys Glu Gly
             355                 360                 365

Pro Leu Lys Val Gly Trp Ser Gly Leu Ala Ser Gly Asn Leu Ser
     370                 375                 380

Val Ala Leu Asn Arg Thr Phe Gln Ala Ala Gly Val Pro Trp Val Glu
385                 390                 395                 400

Asp Val Asn Gly Gly Lys Met Arg Gly Phe Asn Ile Tyr Pro Ser Thr
                 405                 410                 415

Leu Asp Val Asp Leu Asn Val Arg Glu Asp Ala Ala Arg Ala Tyr Tyr
             420                 425                 430
```

```
Phe Pro Tyr Asp Asp Arg Lys Asn Leu His Leu Leu Glu Asn Thr Thr
            435                 440                 445
Ala Asn Arg Leu Phe Trp Lys Asn Gly Ser Ala Glu Glu Ala Ile Ala
450                 455                 460
Asp Gly Val Glu Ile Thr Ser Ala Asp Gly Lys Val Thr Arg Val His
465                 470                 475                 480
Ala Lys Lys Glu Val Ile Ile Ser Ala Gly Ala Leu Arg Ser Pro Leu
                485                 490                 495
Ile Leu Glu Leu Ser Gly Val Gly Asn Pro Thr Ile Leu Lys Lys Asn
            500                 505                 510
Asn Ile Thr Pro Arg Val Asp Leu Pro Thr Val Gly Glu Asn Leu Gln
            515                 520                 525
Asp Gln Phe Asn Asn Gly Met Ala Gly Glu Gly Tyr Gly Val Leu Ala
        530                 535                 540
Gly Ala Ser Thr Val Thr Tyr Pro Ser Ile Ser Asp Val Phe Gly Asn
545                 550                 555                 560
Glu Thr Asp Ser Ile Val Ala Ser Leu Arg Ser Gln Leu Ser Asp Tyr
                565                 570                 575
Ala Ala Ala Thr Val Lys Val Ser Asn Gly His Met Lys Gln Glu Asp
            580                 585                 590
Leu Glu Arg Leu Tyr Gln Leu Gln Phe Asp Leu Ile Val Lys Asp Lys
        595                 600                 605
Val Pro Ile Ala Glu Ile Leu Phe His Pro Gly Gly Asn Ala Val
610                 615                 620
Ser Ser Glu Phe Trp Gly Leu Leu Pro Phe Ala Arg Gly Asn Ile His
625                 630                 635                 640
Ile Ser Ser Asn Asp Pro Thr Ala Pro Ala Ile Asn Pro Asn Tyr
                645                 650                 655
Phe Met Phe Glu Trp Asp Gly Lys Ser Gln Ala Gly Ile Ala Lys Tyr
            660                 665                 670
Ile Arg Lys Ile Leu Arg Ser Ala Pro Leu Asn Lys Leu Ile Ala Lys
        675                 680                 685
Glu Arg Lys Pro Gly Leu Ser Glu Ile Pro Ala Thr Ala Ala Asp Glu
690                 695                 700
Lys Trp Val Glu Trp Leu Lys Ala Asn Tyr Arg Ser Asn Phe His Pro
705                 710                 715                 720
Val Gly Thr Ala Ala Met Met Pro Arg Ser Ile Gly Val Val Asp
                725                 730                 735
Asn Arg Leu Arg Val Tyr Gly Thr Ser Asn Val Arg Val Val Asp Ala
            740                 745                 750
Ser Val Leu Pro Phe Gln Val Cys Gly His Leu Val Ser Thr Leu Tyr
        755                 760                 765
Ala Val Ala Glu Arg Ala Ser Asp Leu Ile Lys Glu Asp Ala Lys Ser
    770                 775                 780
Ala
785

<210> SEQ ID NO 20
<211> LENGTH: 785
<212> TYPE: PRT
<213> ORGANISM: Artificial Sequence
<220> FEATURE:
<223> OTHER INFORMATION: fugion protein

<400> SEQUENCE: 20
```

-continued

```
Gln Ser Ala Ser Gln Phe Thr Asp Pro Thr Gly Phe Gln Phe Thr
1               5                   10                  15

Gly Ile Thr Asp Pro Val His Asp Val Thr Tyr Gly Phe Val Phe Pro
            20                  25                  30

Pro Leu Ala Thr Ser Gly Ala Gln Ser Thr Glu Phe Ile Gly Glu Val
                35                  40                  45

Val Ala Pro Ile Ala Ser Lys Trp Ile Gly Ile Ala Leu Gly Gly Ala
50                  55                  60

Met Asn Asn Asp Leu Leu Leu Val Ala Trp Ala Asn Gly Asn Gln Ile
65                  70                  75                  80

Val Ser Ser Thr Arg Trp Ala Thr Gly Tyr Val Gln Pro Thr Ala Tyr
                85                  90                  95

Thr Gly Thr Ala Thr Leu Thr Thr Leu Pro Glu Thr Thr Ile Asn Ser
                100                 105                 110

Thr His Trp Lys Trp Val Phe Arg Cys Gln Gly Cys Thr Glu Trp Asn
                115                 120                 125

Asn Gly Gly Gly Ile Asp Val Thr Ser Gln Gly Val Leu Ala Trp Ala
            130                 135                 140

Phe Ser Asn Val Ala Val Asp Asp Pro Ser Asp Pro Gln Ser Thr Phe
145                 150                 155                 160

Ser Glu His Thr Asp Phe Gly Phe Phe Gly Ile Asp Tyr Ser Thr Asp
                165                 170                 175

Ser Ala Asn Tyr Gln Asn Tyr Leu Asn Gly Asp Ser Gly Asn Pro Thr
                180                 185                 190

Thr Thr Ser Thr Lys Pro Thr Ser Thr Ser Ser Val Thr Thr Gly
                195                 200                 205

Pro Thr Val Ser Lys Leu Lys Asn Thr Thr Tyr Asp Tyr Ile Val
            210                 215                 220

Val Gly Gly Gly Thr Ser Gly Leu Val Val Ala Asn Arg Leu Ser Glu
225                 230                 235                 240

Asn Pro Asp Val Ser Val Leu Leu Glu Ala Gly Ala Ser Val Phe
                245                 250                 255

Asn Asn Pro Asp Val Thr Asn Ala Asn Gly Tyr Gly Leu Ala Phe Gly
            260                 265                 270

Ser Ala Ile Asp Trp Gln Tyr Gln Ser Ile Asn Gln Ser Tyr Ala Gly
            275                 280                 285

Gly Lys Gln Gln Val Leu Arg Ala Gly Lys Ala Leu Gly Gly Thr Ser
            290                 295                 300

Thr Ile Asn Gly Met Ala Tyr Thr Arg Ala Glu Asp Val Gln Ile Asp
305                 310                 315                 320

Val Trp Gln Lys Leu Gly Asn Glu Gly Trp Thr Trp Lys Asp Leu Leu
                325                 330                 335

Pro Tyr Tyr Leu Lys Ser Glu Asn Leu Thr Ala Pro Thr Ser Ser Gln
                340                 345                 350

Val Ala Ala Gly Ala Ala Tyr Asn Pro Ala Val Asn Gly Lys Glu Gly
                355                 360                 365

Pro Leu Lys Val Gly Trp Ser Gly Ser Leu Ala Ser Gly Asn Leu Ser
    370                 375                 380

Val Ala Leu Asn Arg Thr Phe Gln Ala Ala Gly Val Pro Trp Val Glu
385                 390                 395                 400

Asp Val Asn Gly Gly Lys Met Arg Gly Phe Asn Ile Tyr Pro Ser Thr
                405                 410                 415

Leu Asp Val Asp Leu Asn Val Arg Glu Asp Ala Ala Arg Ala Tyr Tyr
```

```
                420             425             430
Phe Pro Tyr Asp Asp Arg Lys Asn Leu His Leu Leu Glu Asn Thr Thr
            435             440             445
Ala Asn Arg Leu Phe Trp Lys Asn Gly Ser Ala Glu Ala Ile Ala
450             455             460
Asp Gly Val Glu Ile Thr Ser Ala Asp Gly Lys Val Thr Arg Val His
465             470             475             480
Ala Lys Lys Glu Val Ile Ile Ser Ala Gly Ala Leu Arg Ser Pro Leu
            485             490             495
Ile Leu Glu Leu Ser Gly Val Gly Asn Pro Thr Ile Leu Lys Lys Asn
            500             505             510
Asn Ile Thr Pro Arg Val Asp Leu Pro Thr Val Gly Glu Asn Leu Gln
            515             520             525
Asp Gln Phe Asn Asn Gly Met Ala Gly Glu Gly Tyr Gly Val Leu Ala
            530             535             540
Gly Ala Ser Thr Val Thr Tyr Pro Ser Ile Ser Asp Val Phe Gly Asn
545             550             555             560
Glu Thr Asp Ser Ile Val Ala Ser Leu Arg Ser Gln Leu Ser Asp Tyr
            565             570             575
Ala Ala Ala Thr Val Lys Val Ser Asn Gly His Met Lys Gln Glu Asp
            580             585             590
Leu Glu Arg Leu Tyr Gln Leu Gln Phe Asp Leu Ile Val Lys Asp Lys
            595             600             605
Val Pro Ile Ala Glu Ile Leu Phe His Pro Gly Gly Asn Ala Val
            610             615             620
Ser Ser Glu Phe Trp Gly Leu Leu Pro Phe Ala Arg Gly Asn Ile His
625             630             635             640
Ile Ser Ser Asn Asp Pro Thr Ala Pro Ala Ala Ile Asn Pro Asn Tyr
            645             650             655
Phe Met Phe Glu Trp Asp Gly Lys Ser Gln Ala Gly Ile Ala Lys Tyr
            660             665             670
Ile Arg Lys Ile Leu Arg Ser Ala Pro Leu Asn Lys Leu Ile Ala Lys
            675             680             685
Glu Thr Lys Pro Gly Leu Ser Lys Ile Pro Ala Thr Ala Ala Asp Glu
            690             695             700
Lys Trp Val Glu Trp Leu Lys Ala Asn Tyr Arg Ser Asn Phe His Pro
705             710             715             720
Val Gly Thr Ala Ala Met Met Pro Arg Ser Ile Gly Gly Val Val Asp
            725             730             735
Asn Arg Leu Arg Val Tyr Gly Thr Ser Asn Val Arg Val Val Asp Ala
            740             745             750
Ser Val Leu Pro Phe Gln Val Cys Gly His Leu Val Ser Thr Leu Tyr
            755             760             765
Ala Val Ala Glu Arg Ala Ser Asp Leu Ile Lys Glu Asp Ala Lys Ser
            770             775             780
Ala
785

<210> SEQ ID NO 21
<211> LENGTH: 785
<212> TYPE: PRT
<213> ORGANISM: Artificial Sequence
<220> FEATURE:
<223> OTHER INFORMATION: fugion protein
```

```
<400> SEQUENCE: 21

Gln Ser Ala Ser Gln Phe Thr Asp Pro Thr Thr Gly Phe Gln Phe Thr
1               5                   10                  15

Gly Ile Thr Asp Pro Val His Asp Val Thr Tyr Gly Phe Val Phe Pro
            20                  25                  30

Pro Leu Ala Thr Ser Gly Ala Gln Ser Thr Glu Phe Ile Gly Glu Val
            35                  40                  45

Val Ala Pro Ile Ala Ser Lys Trp Ile Gly Ile Ala Leu Gly Gly Ala
        50                  55                  60

Met Asn Asn Asp Leu Leu Val Ala Trp Ala Asn Gly Asn Gln Ile
65                  70                  75                  80

Val Ser Ser Thr Arg Trp Ala Thr Gly Tyr Val Gln Pro Thr Ala Tyr
                    85                  90                  95

Thr Gly Thr Ala Thr Leu Thr Thr Leu Pro Glu Thr Thr Ile Asn Ser
                100                 105                 110

Thr His Trp Lys Trp Val Phe Arg Cys Gln Gly Cys Thr Glu Trp Asn
                115                 120                 125

Asn Gly Gly Gly Ile Asp Val Thr Ser Gln Gly Val Leu Ala Trp Ala
130                 135                 140

Phe Ser Asn Val Ala Val Asp Asp Pro Ser Asp Pro Gln Ser Thr Phe
145                 150                 155                 160

Ser Glu His Thr Asp Phe Gly Phe Phe Gly Ile Asp Tyr Ser Thr Asp
                165                 170                 175

Ser Ala Asn Tyr Gln Asn Tyr Leu Asn Gly Asp Ser Gly Asn Pro Thr
                180                 185                 190

Thr Thr Ser Thr Lys Pro Thr Ser Thr Ser Ser Val Thr Thr Gly
                195                 200                 205

Pro Thr Val Ser Lys Leu Lys Asn Thr Thr Thr Tyr Asp Tyr Ile Val
            210                 215                 220

Val Gly Gly Gly Thr Ser Gly Leu Val Val Ala Asn Arg Leu Ser Glu
225                 230                 235                 240

Asn Pro Asp Val Ser Val Leu Leu Glu Ala Gly Ala Ser Val Phe
                245                 250                 255

Asn Asn Pro Asp Val Thr Asn Ala Asn Gly Tyr Gly Leu Ala Phe Gly
                260                 265                 270

Ser Ala Ile Asp Trp Gln Tyr Gln Ser Ile Asn Gln Ser Tyr Ala Gly
            275                 280                 285

Gly Lys Gln Gln Val Leu Arg Ala Gly Lys Ala Leu Gly Gly Thr Ser
        290                 295                 300

Thr Ile Asn Gly Met Ala Tyr Thr Arg Ala Glu Asp Val Gln Ile Asp
305                 310                 315                 320

Val Trp Gln Lys Leu Gly Asn Glu Gly Trp Thr Trp Lys Asp Leu Leu
                325                 330                 335

Pro Tyr Tyr Leu Lys Ser Glu Asn Leu Thr Ala Pro Thr Ser Ser Gln
                340                 345                 350

Val Ala Ala Gly Ala Ala Tyr Asn Pro Ala Val Asn Gly Lys Glu Gly
            355                 360                 365

Pro Leu Lys Val Gly Trp Ser Gly Ser Leu Ala Ser Gly Asn Leu Ser
        370                 375                 380

Val Ala Leu Asn Arg Thr Phe Gln Ala Ala Gly Val Pro Trp Val Glu
385                 390                 395                 400

Asp Val Asn Gly Gly Lys Met Arg Gly Phe Asn Ile Tyr Pro Ser Thr
                405                 410                 415
```

Leu Asp Val Asp Leu Asn Val Arg Glu Asp Ala Ala Arg Ala Tyr Tyr
             420                 425                 430

Phe Pro Tyr Asp Asp Arg Lys Asn Leu His Leu Leu Glu Asn Thr Thr
         435                 440                 445

Ala Asn Arg Leu Phe Trp Lys Asn Gly Ser Ala Glu Glu Ala Ile Ala
450                 455                 460

Asp Gly Val Glu Ile Thr Ser Ala Asp Gly Lys Val Thr Arg Val His
465                 470                 475                 480

Ala Lys Lys Glu Val Ile Ile Ser Ala Gly Ala Leu Arg Ser Pro Leu
                485                 490                 495

Ile Leu Glu Leu Ser Gly Val Gly Asn Pro Thr Ile Leu Lys Lys Asn
             500                 505                 510

Asn Ile Thr Pro Arg Val Asp Leu Pro Thr Val Gly Glu Asn Leu Gln
         515                 520                 525

Asp Gln Phe Asn Asn Gly Met Ala Gly Glu Gly Tyr Gly Val Leu Ala
530                 535                 540

Gly Ala Ser Thr Val Thr Tyr Pro Ser Ile Ser Asp Val Phe Gly Asn
545                 550                 555                 560

Glu Thr Asp Ser Ile Val Ala Ser Leu Arg Ser Gln Leu Ser Asp Tyr
                565                 570                 575

Ala Ala Ala Thr Val Lys Val Ser Asn Gly His Met Lys Gln Glu Asp
             580                 585                 590

Leu Glu Arg Leu Tyr Gln Leu Gln Phe Asp Leu Ile Val Lys Asp Lys
         595                 600                 605

Val Pro Ile Ala Glu Ile Leu Phe His Pro Gly Gly Gly Asn Ala Val
         610                 615                 620

Ser Ser Glu Phe Trp Gly Leu Leu Pro Phe Ala Arg Gly Asn Ile His
625                 630                 635                 640

Ile Ser Ser Asn Asp Pro Thr Ala Pro Ala Ala Ile Asn Pro Asn Tyr
                645                 650                 655

Phe Met Phe Glu Trp Asp Gly Lys Ser Gln Ala Gly Ile Ala Lys Tyr
             660                 665                 670

Ile Arg Lys Ile Leu Arg Ser Ala Pro Leu Asn Lys Leu Ile Ala Lys
         675                 680                 685

Glu Thr Lys Pro Gly Leu Ser Arg Ile Pro Ala Thr Ala Ala Asp Glu
690                 695                 700

Lys Trp Val Glu Trp Leu Lys Ala Asn Tyr Arg Ser Asn Phe His Pro
705                 710                 715                 720

Val Gly Thr Ala Ala Met Met Pro Arg Ser Ile Gly Gly Val Val Asp
                725                 730                 735

Asn Arg Leu Arg Val Tyr Gly Thr Ser Asn Val Arg Val Val Asp Ala
             740                 745                 750

Ser Val Leu Pro Phe Gln Val Cys Gly His Leu Val Ser Thr Leu Tyr
         755                 760                 765

Ala Val Ala Glu Arg Ala Ser Asp Leu Ile Lys Glu Asp Ala Lys Ser
         770                 775                 780

Ala
785

<210> SEQ ID NO 22
<211> LENGTH: 593
<212> TYPE: PRT
<213> ORGANISM: Artificial Sequence
<220> FEATURE:

<223> OTHER INFORMATION: fugion protein
<220> FEATURE:
<221> NAME/KEY: MUTAGEN
<222> LOCATION: (346)..(346)
<223> OTHER INFORMATION: Xaa is Lys or Arg.

<400> SEQUENCE: 22

Met Leu Phe Ser Leu Ala Phe Leu Ser Ala Leu Ser Leu Ala Thr Ala
1               5                   10                  15

Ser Pro Ala Gly Arg Ala Lys Asn Thr Thr Tyr Asp Tyr Ile Val
            20                  25                  30

Val Gly Gly Gly Thr Ser Gly Leu Val Val Ala Asn Arg Leu Ser Glu
                35                  40                  45

Asn Pro Asp Val Ser Val Leu Leu Leu Glu Ala Gly Ala Ser Val Phe
        50                  55                  60

Asn Asn Pro Asp Val Thr Asn Ala Asn Gly Tyr Gly Leu Ala Phe Gly
65                  70                  75                  80

Ser Ala Ile Asp Trp Gln Tyr Gln Ser Ile Asn Gln Ser Tyr Ala Gly
                85                  90                  95

Gly Lys Gln Gln Val Leu Arg Ala Gly Lys Ala Leu Gly Gly Thr Ser
            100                 105                 110

Thr Ile Asn Gly Met Ala Tyr Thr Arg Ala Glu Asp Val Gln Ile Asp
        115                 120                 125

Val Trp Gln Lys Leu Gly Asn Glu Gly Trp Thr Trp Lys Asp Leu Leu
130                 135                 140

Pro Tyr Tyr Leu Lys Ser Glu Asn Leu Thr Ala Pro Thr Ser Ser Gln
145                 150                 155                 160

Val Ala Ala Gly Ala Ala Tyr Asn Pro Ala Val Asn Gly Lys Glu Gly
                165                 170                 175

Pro Leu Lys Val Gly Trp Ser Gly Ser Leu Ala Ser Gly Asn Leu Ser
            180                 185                 190

Val Ala Leu Asn Arg Thr Phe Gln Ala Ala Gly Val Pro Trp Val Glu
        195                 200                 205

Asp Val Asn Gly Gly Lys Met Arg Gly Phe Asn Ile Tyr Pro Ser Thr
210                 215                 220

Leu Asp Val Asp Leu Asn Val Arg Glu Asp Ala Ala Arg Ala Tyr Tyr
225                 230                 235                 240

Phe Pro Tyr Asp Asp Arg Lys Asn Leu His Leu Leu Glu Asn Thr Thr
                245                 250                 255

Ala Asn Arg Leu Phe Trp Lys Asn Gly Ser Ala Glu Glu Ala Ile Ala
            260                 265                 270

Asp Gly Val Glu Ile Thr Ser Ala Asp Gly Lys Val Thr Arg Val His
        275                 280                 285

Ala Lys Lys Glu Val Ile Ile Ser Ala Gly Ala Leu Arg Ser Pro Leu
290                 295                 300

Ile Leu Glu Leu Ser Gly Val Gly Asn Pro Thr Ile Leu Lys Lys Asn
305                 310                 315                 320

Asn Ile Thr Pro Arg Val Asp Leu Pro Thr Val Gly Glu Asn Leu Gln
                325                 330                 335

Asp Gln Phe Asn Asn Gly Met Ala Gly Xaa Gly Tyr Gly Val Leu Ala
            340                 345                 350

Gly Ala Ser Thr Val Thr Tyr Pro Ser Ile Ser Asp Val Phe Gly Asn
        355                 360                 365

Glu Thr Asp Ser Ile Val Ala Ser Leu Arg Ser Gln Leu Ser Asp Tyr
370                 375                 380

```
Ala Ala Ala Thr Val Lys Val Ser Asn Gly His Met Lys Gln Glu Asp
385                 390                 395                 400

Leu Glu Arg Leu Tyr Gln Leu Gln Phe Asp Leu Ile Val Lys Asp Lys
            405                 410                 415

Val Pro Ile Ala Glu Ile Leu Phe His Pro Gly Gly Gly Asn Ala Val
            420                 425                 430

Ser Ser Glu Phe Trp Gly Leu Leu Pro Phe Ala Arg Gly Asn Ile His
        435                 440                 445

Ile Ser Ser Asn Asp Pro Thr Ala Pro Ala Ile Asn Pro Asn Tyr
    450                 455                 460

Phe Met Phe Glu Trp Asp Gly Lys Ser Gln Ala Gly Ile Ala Lys Tyr
465                 470                 475                 480

Ile Arg Lys Ile Leu Arg Ser Ala Pro Leu Asn Lys Leu Ile Ala Lys
                485                 490                 495

Glu Thr Lys Pro Gly Leu Ser Glu Ile Pro Ala Thr Ala Ala Asp Glu
            500                 505                 510

Lys Trp Val Glu Trp Leu Lys Ala Asn Tyr Arg Ser Asn Phe His Pro
        515                 520                 525

Val Gly Thr Ala Ala Met Met Pro Arg Ser Ile Gly Gly Val Val Asp
    530                 535                 540

Asn Arg Leu Arg Val Tyr Gly Thr Ser Asn Val Arg Val Val Asp Ala
545                 550                 555                 560

Ser Val Leu Pro Phe Gln Val Cys Gly His Leu Val Ser Thr Leu Tyr
                565                 570                 575

Ala Val Ala Glu Arg Ala Ser Asp Leu Ile Lys Glu Asp Ala Lys Ser
            580                 585                 590

Ala

<210> SEQ ID NO 23
<211> LENGTH: 593
<212> TYPE: PRT
<213> ORGANISM: Artificial Sequence
<220> FEATURE:
<223> OTHER INFORMATION: fugion protein
<220> FEATURE:
<221> NAME/KEY: MUTAGEN
<222> LOCATION: (430)..(430)
<223> OTHER INFORMATION: Xaa is Lys or Arg.

<400> SEQUENCE: 23

Met Leu Phe Ser Leu Ala Phe Leu Ser Ala Leu Ser Leu Ala Thr Ala
1               5                   10                  15

Ser Pro Ala Gly Arg Ala Lys Asn Thr Thr Thr Tyr Asp Tyr Ile Val
            20                  25                  30

Val Gly Gly Gly Thr Ser Gly Leu Val Val Ala Asn Arg Leu Ser Glu
        35                  40                  45

Asn Pro Asp Val Ser Val Leu Leu Leu Glu Ala Gly Ala Ser Val Phe
    50                  55                  60

Asn Asn Pro Asp Val Thr Asn Ala Asn Gly Tyr Gly Leu Ala Phe Gly
65                  70                  75                  80

Ser Ala Ile Asp Trp Gln Tyr Gln Ser Ile Asn Gln Ser Tyr Ala Gly
                85                  90                  95

Gly Lys Gln Gln Val Leu Arg Ala Gly Lys Ala Leu Gly Gly Thr Ser
            100                 105                 110

Thr Ile Asn Gly Met Ala Tyr Thr Arg Ala Glu Asp Val Gln Ile Asp
        115                 120                 125
```

Val Trp Gln Lys Leu Gly Asn Glu Gly Trp Thr Trp Lys Asp Leu Leu
130                 135                 140

Pro Tyr Tyr Leu Lys Ser Glu Asn Leu Thr Ala Pro Thr Ser Ser Gln
145                 150                 155                 160

Val Ala Ala Gly Ala Ala Tyr Asn Pro Ala Val Asn Gly Lys Glu Gly
                165                 170                 175

Pro Leu Lys Val Gly Trp Ser Gly Ser Leu Ala Ser Gly Asn Leu Ser
                180                 185                 190

Val Ala Leu Asn Arg Thr Phe Gln Ala Ala Gly Val Pro Trp Val Glu
                195                 200                 205

Asp Val Asn Gly Gly Lys Met Arg Gly Phe Asn Ile Tyr Pro Ser Thr
210                 215                 220

Leu Asp Val Asp Leu Asn Val Arg Glu Asp Ala Ala Arg Ala Tyr Tyr
225                 230                 235                 240

Phe Pro Tyr Asp Asp Arg Lys Asn Leu His Leu Leu Glu Asn Thr Thr
                245                 250                 255

Ala Asn Arg Leu Phe Trp Lys Asn Gly Ser Ala Glu Glu Ala Ile Ala
                260                 265                 270

Asp Gly Val Glu Ile Thr Ser Ala Asp Gly Lys Val Thr Arg Val His
                275                 280                 285

Ala Lys Lys Glu Val Ile Ile Ser Ala Gly Ala Leu Arg Ser Pro Leu
290                 295                 300

Ile Leu Glu Leu Ser Gly Val Gly Asn Pro Thr Ile Leu Lys Lys Asn
305                 310                 315                 320

Asn Ile Thr Pro Arg Val Asp Leu Pro Thr Val Gly Glu Asn Leu Gln
                325                 330                 335

Asp Gln Phe Asn Asn Gly Met Ala Gly Glu Gly Tyr Gly Val Leu Ala
                340                 345                 350

Gly Ala Ser Thr Val Thr Tyr Pro Ser Ile Ser Asp Val Phe Gly Asn
                355                 360                 365

Glu Thr Asp Ser Ile Val Ala Ser Leu Arg Ser Gln Leu Ser Asp Tyr
370                 375                 380

Ala Ala Ala Thr Val Lys Val Ser Asn Gly His Met Lys Gln Glu Asp
385                 390                 395                 400

Leu Glu Arg Leu Tyr Gln Leu Gln Phe Asp Leu Ile Val Lys Asp Lys
                405                 410                 415

Val Pro Ile Ala Glu Ile Leu Phe His Pro Gly Gly Xaa Ala Val
                420                 425                 430

Ser Ser Glu Phe Trp Gly Leu Leu Pro Phe Ala Arg Gly Asn Ile His
                435                 440                 445

Ile Ser Ser Asn Asp Pro Thr Ala Pro Ala Ile Asn Pro Asn Tyr
450                 455                 460

Phe Met Phe Glu Trp Asp Gly Lys Ser Gln Ala Gly Ile Ala Lys Tyr
465                 470                 475                 480

Ile Arg Lys Ile Leu Arg Ser Ala Pro Leu Asn Lys Leu Ile Ala Lys
                485                 490                 495

Glu Thr Lys Pro Gly Leu Ser Glu Ile Pro Ala Thr Ala Ala Asp Glu
                500                 505                 510

Lys Trp Val Glu Trp Leu Lys Ala Asn Tyr Arg Ser Asn Phe His Pro
                515                 520                 525

Val Gly Thr Ala Ala Met Met Pro Arg Ser Ile Gly Gly Val Val Asp
530                 535                 540

-continued

```
Asn Arg Leu Arg Val Tyr Gly Thr Ser Asn Val Arg Val Val Asp Ala
545                 550                 555                 560

Ser Val Leu Pro Phe Gln Val Cys Gly His Leu Val Ser Thr Leu Tyr
                565                 570                 575

Ala Val Ala Glu Arg Ala Ser Asp Leu Ile Lys Glu Asp Ala Lys Ser
            580                 585                 590

Ala

<210> SEQ ID NO 24
<211> LENGTH: 593
<212> TYPE: PRT
<213> ORGANISM: Artificial Sequence
<220> FEATURE:
<223> OTHER INFORMATION: fugion protein
<220> FEATURE:
<221> NAME/KEY: MUTAGEN
<222> LOCATION: (498)..(498)
<223> OTHER INFORMATION: Xaa is Lys or Arg.

<400> SEQUENCE: 24

Met Leu Phe Ser Leu Ala Phe Leu Ser Ala Leu Ser Leu Ala Thr Ala
1               5                   10                  15

Ser Pro Ala Gly Arg Ala Lys Asn Thr Thr Tyr Asp Tyr Ile Val
            20                  25                  30

Val Gly Gly Gly Thr Ser Gly Leu Val Val Ala Asn Arg Leu Ser Glu
        35                  40                  45

Asn Pro Asp Val Ser Val Leu Leu Leu Glu Ala Gly Ala Ser Val Phe
    50                  55                  60

Asn Asn Pro Asp Val Thr Asn Ala Asn Gly Tyr Gly Leu Ala Phe Gly
65                  70                  75                  80

Ser Ala Ile Asp Trp Gln Tyr Gln Ser Ile Asn Gln Ser Tyr Ala Gly
                85                  90                  95

Gly Lys Gln Gln Val Leu Arg Ala Gly Lys Ala Leu Gly Gly Thr Ser
            100                 105                 110

Thr Ile Asn Gly Met Ala Tyr Thr Arg Ala Glu Asp Val Gln Ile Asp
        115                 120                 125

Val Trp Gln Lys Leu Gly Asn Glu Gly Trp Thr Trp Lys Asp Leu Leu
    130                 135                 140

Pro Tyr Tyr Leu Lys Ser Glu Asn Leu Thr Ala Pro Thr Ser Ser Gln
145                 150                 155                 160

Val Ala Ala Gly Ala Ala Tyr Asn Pro Ala Val Asn Gly Lys Glu Gly
                165                 170                 175

Pro Leu Lys Val Gly Trp Ser Gly Ser Leu Ala Ser Gly Asn Leu Ser
            180                 185                 190

Val Ala Leu Asn Arg Thr Phe Gln Ala Ala Gly Val Pro Trp Val Glu
        195                 200                 205

Asp Val Asn Gly Gly Lys Met Arg Gly Phe Asn Ile Tyr Pro Ser Thr
    210                 215                 220

Leu Asp Val Asp Leu Asn Val Arg Glu Asp Ala Ala Arg Ala Tyr Tyr
225                 230                 235                 240

Phe Pro Tyr Asp Asp Arg Lys Asn Leu His Leu Leu Glu Asn Thr Thr
                245                 250                 255

Ala Asn Arg Leu Phe Trp Lys Asn Gly Ser Ala Glu Glu Ala Ile Ala
            260                 265                 270

Asp Gly Val Glu Ile Thr Ser Ala Asp Gly Lys Val Thr Arg Val His
        275                 280                 285
```

```
Ala Lys Lys Glu Val Ile Ile Ser Ala Gly Ala Leu Arg Ser Pro Leu
    290                 295                 300

Ile Leu Glu Leu Ser Gly Val Gly Asn Pro Thr Ile Leu Lys Lys Asn
305                 310                 315                 320

Asn Ile Thr Pro Arg Val Asp Leu Pro Thr Val Gly Glu Asn Leu Gln
                325                 330                 335

Asp Gln Phe Asn Asn Gly Met Ala Gly Glu Gly Tyr Gly Val Leu Ala
            340                 345                 350

Gly Ala Ser Thr Val Thr Tyr Pro Ser Ile Ser Asp Val Phe Gly Asn
        355                 360                 365

Glu Thr Asp Ser Ile Val Ala Ser Leu Arg Ser Gln Leu Ser Asp Tyr
370                 375                 380

Ala Ala Ala Thr Val Lys Val Ser Asn Gly His Met Lys Gln Glu Asp
385                 390                 395                 400

Leu Glu Arg Leu Tyr Gln Leu Gln Phe Asp Leu Ile Val Lys Asp Lys
                405                 410                 415

Val Pro Ile Ala Glu Ile Leu Phe His Pro Gly Gly Gly Asn Ala Val
            420                 425                 430

Ser Ser Glu Phe Trp Gly Leu Leu Pro Phe Ala Arg Gly Asn Ile His
        435                 440                 445

Ile Ser Ser Asn Asp Pro Thr Ala Pro Ala Ala Ile Asn Pro Asn Tyr
450                 455                 460

Phe Met Phe Glu Trp Asp Gly Lys Ser Gln Ala Gly Ile Ala Lys Tyr
465                 470                 475                 480

Ile Arg Lys Ile Leu Arg Ser Ala Pro Leu Asn Lys Leu Ile Ala Lys
                485                 490                 495

Glu Xaa Lys Pro Gly Leu Ser Glu Ile Pro Ala Thr Ala Ala Asp Glu
            500                 505                 510

Lys Trp Val Glu Trp Leu Lys Ala Asn Tyr Arg Ser Asn Phe His Pro
        515                 520                 525

Val Gly Thr Ala Ala Met Met Pro Arg Ser Ile Gly Val Val Asp
530                 535                 540

Asn Arg Leu Arg Val Tyr Gly Thr Ser Asn Val Arg Val Val Asp Ala
545                 550                 555                 560

Ser Val Leu Pro Phe Gln Val Cys Gly His Leu Val Ser Thr Leu Tyr
                565                 570                 575

Ala Val Ala Glu Arg Ala Ser Asp Leu Ile Lys Glu Asp Ala Lys Ser
            580                 585                 590

Ala

<210> SEQ ID NO 25
<211> LENGTH: 593
<212> TYPE: PRT
<213> ORGANISM: Artificial Sequence
<220> FEATURE:
<223> OTHER INFORMATION: fugion protein
<220> FEATURE:
<221> NAME/KEY: MUTAGEN
<222> LOCATION: (504)..(504)
<223> OTHER INFORMATION: Xaa is Lys or Arg.

<400> SEQUENCE: 25

Met Leu Phe Ser Leu Ala Phe Leu Ser Ala Leu Ser Leu Ala Thr Ala
1               5                   10                  15

Ser Pro Ala Gly Arg Ala Lys Asn Thr Thr Tyr Asp Tyr Ile Val
            20                  25                  30
```

-continued

Val Gly Gly Gly Thr Ser Gly Leu Val Val Ala Asn Arg Leu Ser Glu
            35                  40                  45

Asn Pro Asp Val Ser Val Leu Leu Glu Ala Gly Ser Val Phe
 50                  55                  60

Asn Asn Pro Asp Val Thr Asn Ala Asn Gly Tyr Gly Leu Ala Phe Gly
 65                  70                  75                  80

Ser Ala Ile Asp Trp Gln Tyr Gln Ser Ile Asn Gln Ser Tyr Ala Gly
                85                  90                  95

Gly Lys Gln Gln Val Leu Arg Ala Gly Lys Ala Leu Gly Gly Thr Ser
            100                 105                 110

Thr Ile Asn Gly Met Ala Tyr Thr Arg Ala Glu Asp Val Gln Ile Asp
            115                 120                 125

Val Trp Gln Lys Leu Gly Asn Glu Gly Trp Thr Trp Lys Asp Leu Leu
130                 135                 140

Pro Tyr Tyr Leu Lys Ser Glu Asn Leu Thr Ala Pro Thr Ser Ser Gln
145                 150                 155                 160

Val Ala Ala Gly Ala Ala Tyr Asn Pro Ala Val Asn Gly Lys Glu Gly
                165                 170                 175

Pro Leu Lys Val Gly Trp Ser Gly Ser Leu Ala Ser Gly Asn Leu Ser
            180                 185                 190

Val Ala Leu Asn Arg Thr Phe Gln Ala Ala Gly Val Pro Trp Val Glu
            195                 200                 205

Asp Val Asn Gly Gly Lys Met Arg Gly Phe Asn Ile Tyr Pro Ser Thr
            210                 215                 220

Leu Asp Val Asp Leu Asn Val Arg Glu Asp Ala Ala Arg Ala Tyr Tyr
225                 230                 235                 240

Phe Pro Tyr Asp Asp Arg Lys Asn Leu His Leu Leu Glu Asn Thr Thr
                245                 250                 255

Ala Asn Arg Leu Phe Trp Lys Asn Gly Ser Ala Glu Glu Ala Ile Ala
            260                 265                 270

Asp Gly Val Glu Ile Thr Ser Ala Asp Gly Lys Val Thr Arg Val His
            275                 280                 285

Ala Lys Lys Glu Val Ile Ile Ser Ala Gly Ala Leu Arg Ser Pro Leu
            290                 295                 300

Ile Leu Glu Leu Ser Gly Val Gly Asn Pro Thr Ile Leu Lys Lys Asn
305                 310                 315                 320

Asn Ile Thr Pro Arg Val Asp Leu Pro Thr Val Gly Glu Asn Leu Gln
                325                 330                 335

Asp Gln Phe Asn Asn Gly Met Ala Gly Glu Gly Tyr Gly Val Leu Ala
            340                 345                 350

Gly Ala Ser Thr Val Thr Tyr Pro Ser Ile Ser Asp Val Phe Gly Asn
            355                 360                 365

Glu Thr Asp Ser Ile Val Ala Ser Leu Arg Ser Gln Leu Ser Asp Tyr
            370                 375                 380

Ala Ala Ala Thr Val Lys Val Ser Asn Gly His Met Lys Gln Glu Asp
385                 390                 395                 400

Leu Glu Arg Leu Tyr Gln Leu Gln Phe Asp Leu Ile Val Lys Asp Lys
                405                 410                 415

Val Pro Ile Ala Glu Ile Leu Phe His Pro Gly Gly Asn Ala Val
            420                 425                 430

Ser Ser Glu Phe Trp Gly Leu Leu Pro Phe Ala Arg Gly Asn Ile His
            435                 440                 445

Ile Ser Ser Asn Asp Pro Thr Ala Pro Ala Ala Ile Asn Pro Asn Tyr

```
                    450              455              460
Phe Met Phe Glu Trp Asp Gly Lys Ser Gln Ala Gly Ile Ala Lys Tyr
465                 470              475                 480

Ile Arg Lys Ile Leu Arg Ser Ala Pro Leu Asn Lys Leu Ile Ala Lys
                485              490                 495

Glu Thr Lys Pro Gly Leu Ser Xaa Ile Pro Ala Thr Ala Ala Asp Glu
            500              505              510

Lys Trp Val Glu Trp Leu Lys Ala Asn Tyr Arg Ser Asn Phe His Pro
            515              520              525

Val Gly Thr Ala Ala Met Met Pro Arg Ser Ile Gly Gly Val Val Asp
        530              535              540

Asn Arg Leu Arg Val Tyr Gly Thr Ser Asn Val Arg Val Val Asp Ala
545             550              555                 560

Ser Val Leu Pro Phe Gln Val Cys Gly His Leu Val Ser Thr Leu Tyr
                565              570              575

Ala Val Ala Glu Arg Ala Ser Asp Leu Ile Lys Glu Asp Ala Lys Ser
            580              585              590

Ala
```

<210> SEQ ID NO 26
<211> LENGTH: 2112
<212> TYPE: DNA
<213> ORGANISM: Artificial Sequence
<220> FEATURE:
<223> OTHER INFORMATION: DNA coding for fugion protein

<400> SEQUENCE: 26

```
gctgatcttg aagacaatat ggaaaccctc aacgacaatt taaaagtgat cgaaaaagcg      60
gataacgcgg cgcaagtcaa agacgcgtta acgaagatgc gcgccgcagc gctggatgcg     120
caaaaagcaa cgccgccgaa gctcgaagat aaatcaccgg acagcccgga atgaaagat     180
ttccgccacg gtttcgacat tctggtcggt cagattgacg acgcgctgaa gctggcaaat     240
gaaggtaaag taaagaagc gcaggctgct gcagagcaac tgaaaacgac ccgcaacgcc     300
tatcaccaga agtatcgtaa cggcgactcc ggcaacccta cgaccacgag caccaagccc     360
acaagcacga gcagctcagt cacgactgga cccactgttt ctgctacacc ttatgattac     420
atcattgttg gcgctggcac tagcggtctg gtaattgcaa atcgcctgtc tgagctgaac     480
gtcactgtag ctgttatcga ggccggtgat tctggctata ataatccgaa cgtgactaac     540
ccgtccggtt acggttctgc cttcggcact gatatcgatt gggcctatca agcattaat     600
cagaaatacg caggcaacaa aactcaaact ctgcgcgcag gtaaggtgat tggtggcact     660
tccactatca atggtatggc ctacactcgc gcagaggatg tgcagatcga tgcttgggaa     720
gcgattggta atgatggctg aactgggcc aacctgtttc cgtactacaa gaaatcccag     780
actctggaaa ttcctaccac tactcaagct gaagctggcg ctacctacga tgccagcgcc     840
aatggctttg acggtcctct gaaggtaggt tggctgaaca gcctggaaga taccaacaat     900
tttcacacta ctctgaacga tacgtacgct gcactgggtg ttccatccaa cgatgacgtc     960
aataccggca agatggttgg ctacagccgc tatccggcta cctacgatag cgcactgaac    1020
gtgcgccatg acgcaggtcg tgcatactac tatcctattg caaaccgcac caacctgcat    1080
ctgtacccaa acactctggc tcagcgtatc acttggaagt ctaacactga tactccaact    1140
gcgaatggta tcgaggtcct gccgaacgac tctagcactc catacaccat ctatgccaat    1200
tccgaggtca tcctgagcgc tggtgccctg gcgtctccac tgctgctgga actgtctggt    1260
```

| | |
|---|---|
| atcggtaatc cgtccatcct gaacgagcac aatatctctg ttgtggtcga tctgccgacc | 1320 |
| gttggtgaga atctgcaaga ccagaccaat actggtctgg cctacaacag ctctggtaac | 1380 |
| acctccttct ctggtgccgg taccctggtg gcttacccgt ccgcagccca ggtcttcggc | 1440 |
| tctgaagtcc aaaatatctc cgcccatgtt ctgcaatccc tgcctagcta cgctgaacaa | 1500 |
| gtgtccgctg cgtccggtaa catcactaaa gccactgacc tgctggagtt cttcaaagtc | 1560 |
| caacatgacc tgattttctc taccacccac ccggtgccga tggctgagat tctgatcatt | 1620 |
| ccgtctgcaa ccagcttctc ctccgaatac tgggctctgc tgccgtttgc acgtggcagc | 1680 |
| atccacatta ctagctccgt agctggcgag ccggctgcta ttaacccgaa ctattacatg | 1740 |
| tttgactggg acatcactag ccagatcagc actgccaagt tcatccgctc cgtctttgag | 1800 |
| acttctccat ttagctcttt cgtgggctct gagaccaaac caggcctgaa cactgtatct | 1860 |
| gctaatgcaa ccgaggcgga atggtttgat tgggttaaga ctgcttaccg ttctaatttt | 1920 |
| cacccggtgt ctaccgcagc tatgatgcct cgtgaggttg gcggtgttgt ggattctaag | 1980 |
| ctgaaggtat acggcactgc aaacgtgcgc gtggttgatg cgtctatcct gccaatgcag | 2040 |
| gtatctggcc atctggtgtc taccctgtac gctgtggccg aacgtgctgc agacctgatt | 2100 |
| aaggaggata tt | 2112 |

<210> SEQ ID NO 27
<211> LENGTH: 2358
<212> TYPE: DNA
<213> ORGANISM: Artificial Sequence
<220> FEATURE:
<223> OTHER INFORMATION: DNA coding for fugion protein

<400> SEQUENCE: 27

| | |
|---|---|
| cagagtgcct cacagtttac cgaccctacc acaggattcc agttcactgg tatcaccgac | 60 |
| cctgttcatg acgtgaccta cggcttcgtt ttcccccctc tggccaccta cggagcgcaa | 120 |
| tccactgagt tcatcggaga ggttgttgcc cccatcgcat caaaatggat tggtattgcc | 180 |
| ctcggtggcg ccatgaacaa cgacctgcta cttgtggctt gggccaacgg caaccaaatt | 240 |
| gtttcctcca ctcgctgggc tactggctat gtacagccga ctgcatatac gggaactgcc | 300 |
| actttgacaa cactccctga dacaaccatc aactccacgc actggaagtg ggtcttcagg | 360 |
| tgtcagggct gcactgagtg gaacaatggc ggcggaatcg acgtcactag ccagggcgtt | 420 |
| ctggcgtggg cattctccaa cgtcgccgtc gacgacccct ccgacccgca gagtaccttc | 480 |
| agcgagcaca ccgacttcgg cttcttcgga attgactact cgaccgacag cgccaactac | 540 |
| cagaactacc ttaatggcga ctccggcaac cctacgacca cgagcaccaa gcccacaagc | 600 |
| acgagcagct cagtcacgac tggacccact gtttctaagc ttaagaacac tacgacatac | 660 |
| gactacatcg ttgtgggagg cggcacaagt ggtcttgtgg tcgcaaatcg ccttctgag | 720 |
| aaccccgatg tctccgttct tctgcttgag gccggtgctc tgtgttcaa caacccggac | 780 |
| gtaaccaacg ctaacggtta tggattggcc tttggctcgg ccatcgactg cagtaccag | 840 |
| tctattaacc aaagctatgc aggaggtaaa cagcaagttc tgcgtgctgg taaggccctt | 900 |
| ggaggaacca gtacaatcaa tggaatggcc tatacccgcg cagaggatgt ccagattgac | 960 |
| gtttggcaga acttggaaaa cgaaggttgg acgtggaaag atctcctacc atactacctg | 1020 |
| aagagtgaaa acttgacggc ccctaccagc tctcaggttg ctgctggcgc tgcttataac | 1080 |
| cctgccgtga atggaaaaga aggtcctctc aaggtcggct ggtcgggaag cctggcctcc | 1140 |

| | |
|---|---:|
| ggtaatctgt cagttgctct gaaccgtacg ttccaagccg ctggtgttcc atgggttgag | 1200 |
| gatgtcaatg gaggcaagat gcgtggcttc aacatctacc catccaccct cgacgttgac | 1260 |
| ctcaatgtcc gcgaagatgc agcccgggca tactacttcc cttatgatga caggaagaac | 1320 |
| cttcacctgc tggagaacac cactgccaac cgccttttct ggaagaacgg ctctgctgag | 1380 |
| gaagctattg cggatggtgt cgagatcacc tccgctgatg gcaaggtcac tcgtgtgcat | 1440 |
| gcaaagaaag aggtcatcat ctctgctggt gccctgcggt ctcctctcat tctcgagctt | 1500 |
| tcaggagttg aaacccaac catcctcaaa aagaacaaca taaccccacg tgtcgatctc | 1560 |
| cccaccgttg gggagaacct ccaagaccag ttcaacaacg gcatggctgg caaaggatac | 1620 |
| ggcgtccttg ccggtgcctc aaccgtgacc tacccttcca tctccgacgt cttcggtaac | 1680 |
| gagactgact ctatcgttgc atctctccga tctcaactct ccgactacgc cgccgcgacc | 1740 |
| gtcaaggtca gcaacggcca catgaagcag gaggaccttg agcgcctcta ccagctccaa | 1800 |
| tttgacctca tcgtcaagga caaggtccct atcgccgaga tcctcttcca ccccggtggt | 1860 |
| ggaaacgccg tgtcctccga attctggggc ttgcttccct tcgcccgtgg caacatccac | 1920 |
| attagctcca atgacccgac tgctcccgcc gccatcaacc taactactt tatgttcgaa | 1980 |
| tgggacggca gagccaggc cggtatcgcc aagtacatca ggaagattct ccgcagcgca | 2040 |
| ccattgaaca aacttattgc gaaggaaacc aagcccggtc tctctgagat tccggccact | 2100 |
| gctgcgatg agaagtgggt tgaatggctc aaggctaact atcgttccaa cttccacccc | 2160 |
| gtcggaactg ctgccatgat gcctcgttcc attggtggcg ttgttgataa ccgtctccgg | 2220 |
| gtctatggta ccagcaatgt tcgcgtcgta gatgcgtctg tcctgccctt ccaggtttgc | 2280 |
| ggccacttgg ttagcacgct ttatgccgtt gccgagcgcg cttccgactt gattaaggag | 2340 |
| gatgcgaaga gtgcttag | 2358 |

<210> SEQ ID NO 28
<211> LENGTH: 2358
<212> TYPE: DNA
<213> ORGANISM: Artificial Sequence
<220> FEATURE:
<223> OTHER INFORMATION: DNA coding for fugion protein

<400> SEQUENCE: 28

| | |
|---|---:|
| cagagtgcct cacagtttac cgaccctacc acaggattcc agttcactgg tatcaccgac | 60 |
| cctgttcatg acgtgaccta cggcttcgtt ttccccctc tggccacctc cggagcgcaa | 120 |
| tccactgagt tcatcggaga ggttgttgcc cccatcgcat caaaatggat tggtattgcc | 180 |
| ctcggtggcg ccatgaacaa cgacctgcta cttgtggctt gggccaacgg caaccaaatt | 240 |
| gtttcctcca ctcgctgggc tactggctat gtacagccga ctgcatatac gggaactgcc | 300 |
| actttgacaa cactccctga gacaaccatc aactccacgc actggaagtg ggtcttcagg | 360 |
| tgtcagggct gcactgagtg gaacaatggc ggcggaatcg acgtcactag ccagggcgtt | 420 |
| ctggcgtggg cattctccaa cgtcgccgtc gacgaccct cgacccgca gagtaccttc | 480 |
| agcgagcaca ccgacttcgg cttcttcgga attgactact cgaccgacag cgccaactac | 540 |
| cagaactacc ttaatggcga ctccggcaac cctacgacca cgagcaccaa gcccacaagc | 600 |
| acgagcagct cagtcacgac tggacccact gtttctaagc ttaagaacac tacgacatac | 660 |
| gactacatcg ttgtggggagg cggcacaagt ggtcttgtgg tcgcaaatcg cctttctgag | 720 |
| aaccccgatg tctccgttct tctgcttgag gccggtgctt ctgtgttcaa caacccggac | 780 |
| gtaaccaacg ctaacggtta tggattggcc tttggctcgg ccatcgactg gcagtaccag | 840 |

| | |
|---|---:|
| tctattaacc aaagctatgc aggaggtaaa cagcaagttc tgcgtgctgg taaggccctt | 900 |
| ggaggaacca gtacaatcaa tggaatggcc tatacccgcg cagaggatgt ccagattgac | 960 |
| gtttggcaga aacttggaaa cgaaggttgg acgtggaaag atctcctacc atactacctg | 1020 |
| aagagtgaaa acttgacggc ccctaccagc tctcaggttg ctgctggcgc tgcttataac | 1080 |
| cctgccgtga atggaaaaga aggtcctctc aaggtcggct ggtcgggaag cctggcctcc | 1140 |
| ggtaatctgt cagttgctct gaaccgtacg ttccaagccg ctggtgttcc atgggttgag | 1200 |
| gatgtcaatg gaggcaagat gcgtggcttc aacatctacc catccaccct cgacgttgac | 1260 |
| ctcaatgtcc gcgaagatgc agcccgggca tactacttcc cttatgatga caggaagaac | 1320 |
| cttcacctgc tggagaacac cactgccaac cgccttttct ggaagaacgg ctctgctgag | 1380 |
| gaagctattg cggatggtgt cgagatcacc tccgctgatg gcaaggtcac tcgtgtgcat | 1440 |
| gcaaagaaag aggtcatcat ctctgctggt gccctgcggt ctcctctcat tctcgagctt | 1500 |
| tcaggagttg gaaacccaac catcctcaaa aagaacaaca taaccccacg tgtcgatctc | 1560 |
| cccaccgttg gggagaacct ccaagaccag ttcaacaacg gcatggctgg ccgcggatac | 1620 |
| ggcgtccttg ccggtgcctc aaccgtgacc taccccttcca tctccgacgt cttcggtaac | 1680 |
| gagactgact ctatcgttgc atctctccga tctcaactct ccgactacgc cgccgcgacc | 1740 |
| gtcaaggtca gcaacggcca catgaagcag gaggaccttg agcgcctcta ccagctccaa | 1800 |
| tttgacctca tcgtcaagga caaggtccct atcgccgaga tcctcttcca ccccggtggt | 1860 |
| ggaaacgccg tgtcctccga attctgggggc ttgcttccct tcgcccgtgg caacatccac | 1920 |
| attagctcca atgacccgac tgctcccgcc gccatcaacc ctaactactt tatgttcgaa | 1980 |
| tgggacggca agagccaggc cggtatcgcc aagtacatca ggaagattct ccgcagcgca | 2040 |
| ccattgaaca aacttattgc gaaggaaacc aagcccggtc tctctgagat tccggccact | 2100 |
| gctgcggatg agaagtgggt tgaatggctc aaggctaact atcgttccaa cttccacccc | 2160 |
| gtcggaactg ctgccatgat gcctcgttcc attggtggcg ttgttgataa ccgtctccgg | 2220 |
| gtctatggta ccagcaatgt tcgcgtcgta gatgcgtctg tcctgcccctt ccaggtttgc | 2280 |
| ggccacttgg ttagcacgct ttatgccgtt gccgagcgcg cttccgactt gattaaggag | 2340 |
| gatgcgaaga gtgcttag | 2358 |

<210> SEQ ID NO 29
<211> LENGTH: 2358
<212> TYPE: DNA
<213> ORGANISM: Artificial Sequence
<220> FEATURE:
<223> OTHER INFORMATION: DNA coding for fugion protein

<400> SEQUENCE: 29

| | |
|---|---:|
| cagagtgcct cacagtttac cgaccctacc acaggattcc agttcactgg tatcaccgac | 60 |
| cctgttcatg acgtgaccta cggcttcgtt ttccccccctc tggccaccctc cggagcgcaa | 120 |
| tccactgagt tcatcggaga ggttgttgcc cccatcgcat caaaatggat tggtattgcc | 180 |
| ctcggtggcg ccatgaacaa cgacctgcta cttgtggctt gggccaacgg caaccaaatt | 240 |
| gtttcctcca ctcgctgggc tactggctat gtacagccga ctgcatatac gggaactgcc | 300 |
| actttgacaa cactccctga cacaaccatc aactccacgc actggaagtg gtcttcagg | 360 |
| tgtcagggct gcactgagtg gaacaatggc ggcggaatcg acgtcactag ccagggcgtt | 420 |
| ctggcgtggg cattctccaa cgtcgccgtc gacgaccccct ccgacccgca gagtaccttc | 480 |

| | |
|---|---:|
| agcgagcaca ccgacttcgg cttcttcgga attgactact cgaccgacag cgccaactac | 540 |
| cagaactacc ttaatggcga ctccggcaac cctacgacca cgagcaccaa gcccacaagc | 600 |
| acgagcagct cagtcacgac tggacccact gtttctaagc ttaagaacac tacgacatac | 660 |
| gactacatcg ttgtgggagg cggcacaagt ggtcttgtgg tcgcaaatcg cctttctgag | 720 |
| aaccccgatg tctccgttct tctgcttgag gccggtgctt ctgtgttcaa caacccggac | 780 |
| gtaaccaacg ctaacggtta tggattggcc tttggctcgg ccatcgactg gcagtaccag | 840 |
| tctattaacc aaagctatgc aggaggtaaa cagcaagttc tgcgtgctgg taaggccctt | 900 |
| ggaggaacca gtacaatcaa tggaatggcc tatacccgcg cagaggatgt ccagattgac | 960 |
| gtttggcaga aacttggaaa cgaaggttgg acgtggaaag atctcctacc atactacctg | 1020 |
| aagagtgaaa acttgacggc ccctaccagc tctcaggttg ctgctggcgc tgcttataac | 1080 |
| cctgccgtga atggaaaaga aggtcctctc aaggtcggct ggtcgggaag cctggcctcc | 1140 |
| ggtaatctgt cagttgctct gaaccgtacg ttccaagccg ctggtgttcc atgggttgag | 1200 |
| gatgtcaatg gaggcaagat gcgtggcttc aacatctacc catccaccct cgacgttgac | 1260 |
| ctcaatgtcc gcgaagatgc agcccgggca tactacttcc cttatgatga caggaagaac | 1320 |
| cttcacctgc tggagaacac cactgccaac cgccttttct ggaagaacgg ctctgctgag | 1380 |
| gaagctattg cggatggtgt cgagatcacc tccgctgatg gcaaggtcac tcgtgtgcat | 1440 |
| gcaaagaaag aggtcatcat ctctgctggt gccctgcgt ctcctctcat tctcgagctt | 1500 |
| tcaggagttg gaaacccaac catcctcaaa aagaacaaca taaccccacg tgtcgatctc | 1560 |
| cccaccgttg gggagaacct ccaagaccag ttcaacaacg gcatggctgg cgaaggatac | 1620 |
| ggcgtccttg ccggtgcctc aaccgtgacc tacccttcca tctccgacgt cttcggtaac | 1680 |
| gagactgact ctatcgttgc atctctccga tctcaactct ccgactacgc cgccgcgacc | 1740 |
| gtcaaggtca gcaacggcca catgaagcag gaggaccttg agcgcctcta ccagctccaa | 1800 |
| tttgacctca tcgtcaagga caaggtccct atcgccgaga tcctcttcca ccccggtggt | 1860 |
| ggaaaagccg tgtcctccga attctggggc ttgcttccct tcgccgtgg caacatccac | 1920 |
| attagctcca atgaccccga ctgctcccgc gccatcaacc ctaactactt tatgttcgaa | 1980 |
| tgggacggca agagccaggc cggtatcgcc aagtacatca ggaagattct ccgcagcgca | 2040 |
| ccattgaaca aacttattgc gaaggaaacc aagcccggtc tctctgagat ccgccact | 2100 |
| gctgcggatg agaagtgggt tgaatggctc aaggctaact atcgttccaa cttccacccc | 2160 |
| gtcggaactg ctgccatgat gcctcgttcc attggtggcg ttgttgataa ccgtctccgg | 2220 |
| gtctatggta ccagcaatgt tcgcgtcgta gatgcgtctg tcctgccctt ccaggtttgc | 2280 |
| ggccacttgg ttagcacgct ttatgccgtt gccgagcgcg cttccgactt gattaaggag | 2340 |
| gatgcgaaga gtgcttag | 2358 |

<210> SEQ ID NO 30
<211> LENGTH: 2358
<212> TYPE: DNA
<213> ORGANISM: Artificial Sequence
<220> FEATURE:
<223> OTHER INFORMATION: DNA coding for fugion protein

<400> SEQUENCE: 30

| | |
|---|---:|
| cagagtgcct cacagtttac cgaccctacc acaggattcc agttcactgg tatcaccgac | 60 |
| cctgttcatg acgtgaccta cggcttcgtt ttccccctc tggccacctc cggagcgcaa | 120 |
| tccactgagt tcatcggaga ggttgttgcc cccatcgcat caaaatggat tggtattgcc | 180 |

```
ctcggtggcg ccatgaacaa cgacctgcta cttgtggctt gggccaacgg caaccaaatt    240
gtttcctcca ctcgctgggc tactggctat gtacagccga ctgcatatac gggaactgcc    300
actttgacaa cactccctga gacaaccatc aactccacgc actggaagtg ggtcttcagg    360
tgtcagggct gcactgagtg gaacaatggc ggcggaatcg acgtcactag ccagggcgtt    420
ctggcgtggg cattctccaa cgtcgccgtc gacgacccct ccgacccgca gagtaccttc    480
agcgagcaca ccgacttcgg cttcttcgga attgactact cgaccgacag cgccaactac    540
cagaactacc ttaatggcga ctccggcaac cctacgacca cgagcaccaa gcccacaagc    600
acgagcagct cagtcacgac tggacccact gtttctaagc ttaagaacac tacgacatac    660
gactacatcg ttgtgggagg cggcacaagt ggtcttgtgg tcgcaaatcg cctttctgag    720
aaccccgatg tctccgttct tctgcttgag gccggtgctt ctgtgttcaa caacccggac    780
gtaaccaacg ctaacggtta tggattggcc tttggctcgg ccatcgactg cagtaccag     840
tctattaacc aaagctatgc aggaggtaaa cagcaagttc tgcgtgctgg taaggccctt    900
ggaggaacca gtacaatcaa tggaatggcc tatacccgcg cagaggatgt ccagattgac    960
gtttggcaga aacttggaaa cgaaggttgg acgtggaaag atctcctacc atactacctg   1020
aagagtgaaa acttgacggc ccctaccagc tctcaggttg ctgctggcgc tgcttataac   1080
cctgccgtga atggaaaaga aggtcctctc aaggtcggct ggtcgggaag cctggcctcc   1140
ggtaatctgt cagttgctct gaaccgtacg ttccaagccg ctggtgttcc atgggttgag   1200
gatgtcaatg gaggcaagat gcgtggcttc aacatctacc catccaccct cgacgttgac   1260
ctcaatgtcc gcgaagatgc agcccgggca tactacttcc cttatgatga caggaagaac   1320
cttcacctgc tggagaacac cactgccaac cgccttttct ggaagaacgg ctctgctgag   1380
gaagctattg cggatggtgt cgagatcacc tccgctgatg gcaaggtcac tcgtgtgcat   1440
gcaaagaaag aggtcatcat ctctgctggt gccctgcggt ctcctctcat tctcgagctt   1500
tcaggagttg gaaacccaac catcctcaaa aagaacaaca taaccccacg tgtcgatctc   1560
cccaccgttg gggagaacct ccaagaccag ttcaacaacg gcatggctgg cgaaggatac   1620
ggcgtccttg ccggtgcctc aaccgtgacc taccttcca tctccgacgt cttcggtaac    1680
gagactgact ctatcgttgc atctctccga tctcaactct ccgactacgc cgccgcgacc   1740
gtcaaggtca gcaacggcca catgaagcag gaggaccttg agcgcctcta ccagctccaa   1800
tttgacctca tcgtcaagga caaggtccct atcgccgaga tcctcttcca ccccggtggt   1860
ggacgcgccg tgtcctccga attctggggc ttgcttccct tcgcccgtgg caacatccac   1920
attagctcca atgacccgac tgctcccgcc gccatcaacc ctaactactt tatgttcgaa   1980
tgggacggca agagccaggc cggtatcgcc aagtacatca ggaagattct ccgcagcgca   2040
ccattgaaca aacttattgc gaaggaaacc aagcccggtc tctctgagat tccggccact   2100
gctgcggatg agaagtgggt tgaatggctc aaggctaact atcgttccaa cttccacccc   2160
gtcggaactg ctgccatgat gcctcgttcc attggtggcg ttgttgataa ccgtctccgg   2220
gtctatggta ccagcaatgt tcgcgtcgta gatgcgtctg tcctgccctt ccaggtttgc   2280
ggccacttgg ttagcacgct ttatgccgtt gccgagcgcg cttccgactt gattaaggag   2340
gatgcgaaga gtgcttag                                                 2358
```

<210> SEQ ID NO 31
<211> LENGTH: 2358
<212> TYPE: DNA

<213> ORGANISM: Artificial Sequence
<220> FEATURE:
<223> OTHER INFORMATION: DNA coding for fugion protein

<400> SEQUENCE: 31

| | | | | | |
|---|---|---|---|---|---|
| cagagtgcct | cacagtttac | cgaccctacc | acaggattcc | agttcactgg | tatcaccgac | 60 |
| cctgttcatg | acgtgaccta | cggcttcgtt | ttccccctc | tggccacctc | cggagcgcaa | 120 |
| tccactgagt | tcatcggaga | ggttgttgcc | cccatcgcat | caaaatggat | tggtattgcc | 180 |
| ctcggtggcg | ccatgaacaa | cgacctgcta | cttgtggctt | gggccaacgg | caaccaaatt | 240 |
| gtttcctcca | ctcgctgggc | tactggctat | gtacagccga | ctgcatatac | gggaactgcc | 300 |
| actttgacaa | cactccctga | gacaaccatc | aactccacgc | actggaagtg | ggtcttcagg | 360 |
| tgtcagggct | gcactgagtg | gaacaatggc | ggcggaatcg | acgtcactag | ccagggcgtt | 420 |
| ctggcgtggg | cattctccaa | cgtcgccgtc | gacgacccct | ccgacccgca | gagtaccttc | 480 |
| agcgagcaca | ccgacttcgg | cttcttcgga | attgactact | cgaccgacag | cgccaactac | 540 |
| cagaactacc | ttaatggcga | ctccggcaac | cctacgacca | cgagcaccaa | gcccacaagc | 600 |
| acgagcagct | cagtcacgac | tggaccccact | gtttctaagc | ttaagaacac | tacgacatac | 660 |
| gactacatcg | ttgtgggagg | cggcacaagt | ggtcttgtgg | tcgcaaatcg | cctttctgag | 720 |
| aaccccgatg | tctccgttct | tctgcttgag | gccggtgctt | ctgtgttcaa | caacccggac | 780 |
| gtaaccaacg | ctaacggtta | tggattggcc | tttggctcgg | ccatcgactg | gcagtaccag | 840 |
| tctattaacc | aaagctatgc | aggaggtaaa | cagcaagttc | tgcgtgctgg | taaggccctt | 900 |
| ggaggaacca | gtacaatcaa | tggaatggcc | tatcccgcg | cagaggatgt | ccagattgac | 960 |
| gtttggcaga | aacttggaaa | cgaaggttgg | acgtggaaag | atctcctacc | atactacctg | 1020 |
| aagagtgaaa | acttgacggc | ccctaccagc | tctcaggttg | ctgctggcgc | tgcttataac | 1080 |
| cctgccgtga | atggaaaaga | aggtcctctc | aaggtcggct | ggtcgggaag | cctggcctcc | 1140 |
| ggtaatctgt | cagttgctct | gaaccgtacg | ttccaagccg | ctggtgttcc | atgggttgag | 1200 |
| gatgtcaatg | gaggcaagat | gcgtggcttc | aacatctacc | catccaccct | cgacgttgac | 1260 |
| ctcaatgtcc | gcgaagatgc | agcccgggca | tactacttcc | cttatgatga | caggaagaac | 1320 |
| cttcacctgc | tggagaacac | cactgccaac | cgccttttct | ggaagaacgg | ctctgctgag | 1380 |
| gaagctattg | cggatggtgt | cgagatcacc | tccgctgatg | caaggtcac | tcgtgtgcat | 1440 |
| gcaaagaaag | aggtcatcat | ctctgctggt | gccctgcggt | ctcctctcat | tctcgagctt | 1500 |
| tcaggagttg | gaaacccaac | catcctcaaa | aagaacaaca | taaccccacg | tgtcgatctc | 1560 |
| cccaccgttg | gggagaacct | ccaagaccag | ttcaacaacg | gcatggctgg | cgaaggatac | 1620 |
| ggcgtccttg | ccggtgcctc | aaccgtgacc | taccccttcca | tctccgacgt | cttcggtaac | 1680 |
| gagactgact | ctatcgttgc | atctctccga | tctcaactct | ccgactacgc | cgccgcgacc | 1740 |
| gtcaaggtca | gcaacggcca | catgaagcag | gaggaccttg | agcgcctcta | ccagctccaa | 1800 |
| tttgacctca | tcgtcaagga | caaggtccct | atcgccgaga | tcctcttcca | ccccggtggt | 1860 |
| ggaaacgccg | tgtcctccga | attctgggc | ttgcttccct | tcgcccgtgg | caacatccac | 1920 |
| attagctcca | atgacccgac | tgctcccgcc | gccatcaacc | ctaactactt | tatgttcgaa | 1980 |
| tgggacggca | agagccaggc | cggtatcgcc | aagtacatca | ggaagattct | ccgcagcgca | 2040 |
| ccattgaaca | aacttattgc | gaaggaaaaa | aagcccggtc | tctctgagat | tccggccact | 2100 |
| gctgcgatg | agagtgggt | tgaatggctc | aaggctaact | atcgttccaa | cttccacccc | 2160 |
| gtcggaactg | ctgccatgat | gcctcgttcc | attggtggcg | ttgttgataa | ccgtctccgg | 2220 |

```
gtctatggta ccagcaatgt tcgcgtcgta gatgcgtctg tcctgcccct tccaggtttgc    2280 ggccacttgg ttagcacgct ttatgccgtt gccgagcgcg cttccgactt gattaaggag    2340
gatgcgaaga gtgcttag                                                  2358

<210> SEQ ID NO 32
<211> LENGTH: 2358
<212> TYPE: DNA
<213> ORGANISM: Artificial Sequence
<220> FEATURE:
<223> OTHER INFORMATION: DNA coding for fugion protein

<400> SEQUENCE: 32
cagagtgcct cacagtttac cgaccctacc acaggattcc agttcactgg tatcaccgac      60
cctgttcatg acgtgaccta cggcttcgtt ttcccccctc tggccaccct cggagcgcaa     120
tccactgagt tcatcggaga ggttgttgcc cccatcgcat caaaatggat tggtattgcc     180
ctcggtggcg ccatgaacaa cgacctgcta cttgtggctt gggccaacgg caaccaaatt     240
gtttcctcca ctcgctgggc tactggctat gtacagccga ctgcatatac gggaactgcc     300
actttgacaa cactccctga cacaaccatc aactccacgc actggaagtg ggtcttcagg     360
tgtcagggct gcactgagtg aacaatggcg gcggaatcg acgtcactag ccagggcgtt     420
ctggcgtggg cattctccaa cgtcgccgtc gacgacccct ccgacccgca gagtaccttc     480
agcgagcaca ccgacttcgg cttcttcgga attgactact cgaccgacag cgccaactac     540
cagaactacc ttaatggcga ctccggcaac cctacgacca cgagcaccaa gcccacaagc     600
acgagcagct cagtcacgac tggacccact gtttctaagc ttaagaacac tacgacatac     660
gactacatcg ttgtgggagg cggcacaagt ggtcttgtgg tcgcaaatcg cctttctgag     720
aaccccgatg tctccgttct ctgcttgag gccggtgctt ctgtgttcaa caacccggac     780
gtaaccaacg ctaacggtta tggattggcc tttggctcgg ccatcgactg cagtaccag     840 tctattaacc aaagctatgc aggaggtaaa cagcaagttc tgcgtgctgg taaggcccttg    900 ggaggaacca gtacaatcaa tggaatggcc tatacccgcg cagaggatgt ccagattgac     960
gtttggcaga acttggaaaa cgaaggttgg acgtggaaag atctcctacc atactacctg    1020
aagagtgaaa acttgacggc ccctaccagc tctcaggttg ctgctggcgc tgcttataac    1080
cctgccgtga atgaaaagaa aggtcctctc aaggtcggct ggtcgggaag cctggcctcc    1140
ggtaatctgt cagttgctct gaaccgtacg ttccaagccg ctggtgttcc atgggttgag    1200
gatgtcaatg gaggcaagat gcgtggcttc aacatctacc atccaccct cgacgttgac    1260 ctcaatgtcc gcgaagatgc agcccgggca tactacttcc cttatgatga caggaagaac    1320
cttcacctgc tggagaacac cactgccaac cgccttttct ggaagaacgg ctctgctgag    1380
gaagctattg cggatggtgt cgagatcacc tccgctgatg gcaaggtcac tcgtgtgcat    1440
gcaaagaaag aggtcatcat ctctgctggt gccctgcgt ctcctctcat tctcgagctt    1500
tcaggagttg gaaacccaac catcctcaaa agaacaaca taaccccacg tgtcgatctc    1560
cccaccgttg gggagaacct ccaagaccag ttcaacaacg gcatggctgg cgaaggatac    1620
ggcgtccttg ccggtgcctc aaccgtgacc taccttcca tctccgacgt cttcggtaac    1680
gagactgact ctatcgttgc atctctccga tctcaactct ccgactacgc cgccgcgacc    1740
gtcaaggtca gcaacggcca catgaagcag gaggaccttg agcgcctcta ccagctccaa    1800
tttgacctca tcgtcaagga caaggtccct atcgccgaga tcctcttcca cccgtggtggt    1860
```

```
ggaaacgccg tgtcctccga attctggggc ttgcttccct tcgcccgtgg caacatccac    1920
attagctcca atgacccgac tgctcccgcc gccatcaacc ctaactactt tatgttcgaa    1980
tgggacggca agagccaggc cggtatcgcc aagtacatca ggaagattct ccgcagcgca    2040
ccattgaaca aacttattgc gaaggaacgc aagcccggtc tctctgagat ccggccact    2100 gctgcggatg agaagtgggt tgaatggctc aaggctaact atcgttccaa cttccacccc    2160
gtcggaactg ctgccatgat gcctcgttcc attggtggcg ttgttgataa ccgtctccgg    2220
gtctatggta ccagcaatgt tcgcgtcgta gatgcgtctg tcctgcccct tccaggtttgc    2280 ggccacttgg ttagcacgct ttatgccgtt gccgagcgcg cttccgactt gattaaggag    2340
gatgcgaaga gtgcttag                                                  2358
```

<210> SEQ ID NO 33
<211> LENGTH: 2358
<212> TYPE: DNA
<213> ORGANISM: Artificial Sequence
<220> FEATURE:
<223> OTHER INFORMATION: DNA coding for fugion protein

<400> SEQUENCE: 33

```
cagagtgcct cacagtttac cgaccctacc acaggattcc agttcactgg tatcaccgac      60
cctgttcatg acgtgaccta cggcttcgtt ttccccctc tggccacctc cggagcgcaa     120
tccactgagt tcatcggaga ggttgttgcc cccatcgcat caaaatggat tggtattgcc     180
ctcggtggcg ccatgaacaa cgacctgcta cttgtggctt gggccaacgg caaccaaatt     240
gtttcctcca ctcgctgggc tactggctat gtacagccga ctgcatatac gggaactgcc     300
actttgacaa cactccctga cacaaccatc aactccacgc actggaagtg ggtcttcagg     360
tgtcagggct gcactgagtg gaacaatggc ggcggaatcg acgtcactag ccagggcgtt     420
ctggcgtggg cattctccaa cgtcgccgtc gacgaccct ccgacccgca gagtaccttc      480
agcgagcaca ccgacttcgg cttcttcgga attgactact cgaccgacag cgccaactac     540
cagaactacc ttaatggcga ctccggcaac cctacgacca cgagcaccaa gcccacaagc     600
acgagcagct cagtcacgac tggacccact gtttctaagc ttaagaacac tacgacatac     660
gactacatcg ttgtgggagg cggcacaagt ggtcttgtgg tcgcaaatcg cctttctgag     720
aaccccgatg tctccgttct tctgcttgag gccggtgctt ctgtgttcaa caaccccggac    780 gtaaccaacg ctaacggtta tggattggcc tttggctcgg ccatcgactg cagtaccag      840 tctattaacc aaagctatgc aggaggtaaa cagcaagttc tgcgtgctgg taaggccctt     900
ggaggaacca gtacaatcaa tggaatggcc tatacccgcg cagaggatgt ccagattgac     960
gtttggcaga aacttggaaa cgaaggttgg acgtggaaag atctcctacc atactacctg    1020
aagagtgaaa acttgacggc ccctaccagc tctcaggttg ctgctggcgc tgcttataac    1080
cctgccgtga atgaaaaaga aggtcctctc aaggtcggct ggtcgggaag cctggcctcc    1140
ggtaatctgt cagttgctct gaaccgtacg ttccaagccg ctggtgttcc atgggttgag    1200
gatgtcaatg gaggcaagat gcgtggcttc aacatctacc catccaccct cgacgttgac    1260
ctcaatgtcc gcgaagatgc agcccgggca tactacttcc cttatgatga caggaagaac    1320
cttcacctgc tggagaacac cactgccaac cgccttttct ggaagaacgg ctctgctgag    1380
gaagctattg cggatggtgt cgagatcacc tccgctgatg gcaaggtcac tcgtgtgcat    1440
gcaaagaaag aggtcatcat ctctgctggt gccctgcgt ctcctctcat tctcgagctt     1500
tcaggagttg gaaacccaac catcctcaaa aagaacaaca taaccccacg tgtcgatctc    1560
```

| | |
|---|---|
| cccaccgttg gggagaacct ccaagaccag ttcaacaacg gcatggctgg cgaaggatac | 1620 |
| ggcgtccttg ccggtgcctc aaccgtgacc taccctteca tctccgacgt cttcggtaac | 1680 |
| gagactgact ctatcgttgc atctctccga tctcaactct ccgactacgc cgccgcgacc | 1740 |
| gtcaaggtca gcaacggcca catgaagcag gaggaccttg agcgcctcta ccagctccaa | 1800 |
| tttgacctca tcgtcaagga caaggtccct atcgccgaga tcctcttcca ccccggtggt | 1860 |
| ggaaacgccg tgtcctccga attctggggc ttgcttccct tcgcccgtgg caacatccac | 1920 |
| attagctcca atgacccgac tgctcccgcc gccatcaacc ctaactactt tatgttcgaa | 1980 |
| tgggacggca gagccaggc cggtatcgcc aagtacatca ggaagattct ccgcagcgca | 2040 |
| ccattgaaca aacttattgc gaaggaaacc aagcccggtc tctctaaaat tccggccact | 2100 |
| gctgcggatg agaagtgggt tgaatggctc aaggctaact atcgttccaa cttccacccc | 2160 |
| gtcggaactg ctgccatgat gcctcgttcc attggtggcg ttgttgataa ccgtctccgg | 2220 |
| gtctatggta ccagcaatgt tcgcgtcgta gatgcgtctg tcctgcccttccaggtttgc | 2280 |
| ggccacttgg ttagcacgct ttatgccgtt gccgagcgcg cttccgactt gattaaggag | 2340 |
| gatgcgaaga gtgcttag | 2358 |

<210> SEQ ID NO 34
<211> LENGTH: 2358
<212> TYPE: DNA
<213> ORGANISM: Artificial Sequence
<220> FEATURE:
<223> OTHER INFORMATION: DNA coding for fugion protein

<400> SEQUENCE: 34

| | |
|---|---|
| cagagtgcct cacagtttac cgaccctacc acaggattcc agttcactgg tatcaccgac | 60 |
| cctgttcatg acgtgaccta cggcttcgtt ttccccctc tggccaccte cggagcgcaa | 120 |
| tccactgagt tcatcggaga ggttgttgcc cccatcgcat caaaatggat tggtattgcc | 180 |
| ctcggtggcg ccatgaacaa cgacctgcta cttgtggctt gggccaacgg caaccaaatt | 240 |
| gtttcctcca ctcgctgggc tactggctat gtacagccga ctgcatatac gggaactgcc | 300 |
| actttgacaa cactccctga gacaaccatc aactccacgc actggaagtg ggtcttcagg | 360 |
| tgtcagggct gcactgagtg gaacaatggc ggcggaatcg acgtcactag ccagggcgtt | 420 |
| ctggcgtggg cattctccaa cgtcgccgtc gacgaccct ccgacccgca gagtaccttc | 480 |
| agcgagcaca ccgacttcgg cttcttcgga attgactact cgaccgacag cgccaactac | 540 |
| cagaactacc ttaatggcga ctccggcaac cctacgacca cgagcaccaa gcccacaagc | 600 |
| acgagcagct cagtcacgac tggacccact gtttctaagc ttaagaacac tacgacatac | 660 |
| gactacatcg ttgtgggagg cggcacaagt ggtcttgtgg tcgcaaatcg cctttctgag | 720 |
| aaccccgatg tctccgttct tctgcttgag gccggtgctt ctgtgttcaa caacccggac | 780 |
| gtaaccaacg ctaacggtta tggattggcc tttggctcgg ccatcgactg gcagtaccag | 840 |
| tctattaacc aaagctatgc aggaggtaaa cagcaagttc tgcgtgctgg taaggccctt | 900 |
| ggaggaacca gtacaatcaa tggaatggcc tatacccgcg cagaggatgt ccagattgac | 960 |
| gtttggcaga aacttggaaa cgaaggttgg acgtggaaag atctcctacc atactacctg | 1020 |
| aagagtgaaa acttgacggc ccctaccagc tctcaggttg ctgctggcgc tgcttataac | 1080 |
| cctgccgtga atgaaaaga aggtcctctc aaggtcggct ggtcgggaag cctggcctcc | 1140 |
| ggtaatctgt cagttgctct gaaccgtacg ttccaagccg ctggtgttcc atgggttgag | 1200 |

```
gatgtcaatg gaggcaagat gcgtggcttc aacatctacc catccaccct cgacgttgac    1260
ctcaatgtcc gcgaagatgc agcccgggca tactacttcc cttatgatga caggaagaac    1320
cttcacctgc tggagaacac cactgccaac cgccttttct ggaagaacgg ctctgctgag    1380
gaagctattg cggatggtgt cgagatcacc tccgctgatg gcaaggtcac tcgtgtgcat    1440
gcaaagaaag aggtcatcat ctctgctggt gccctgcggt ctcctctcat tctcgagctt    1500
tcaggagttg gaaacccaac catcctcaaa aagaacaaca taaccccacg tgtcgatctc    1560
cccaccgttg gggagaacct ccaagaccag ttcaacaacg gcatggctgg cgaaggatac    1620
ggcgtccttg ccggtgcctc aaccgtgacc taccettcca tctccgacgt cttcggtaac    1680
gagactgact ctatcgttgc atctctccga tctcaactct ccgactacgc cgccgcgacc    1740
gtcaaggtca gcaacggcca catgaagcag gaggaccttg agcgcctcta ccagctccaa    1800
tttgacctca tcgtcaagga caaggtccct atcgccgaga tcctcttcca ccccggtggt    1860
ggaaacgccg tgtcctccga attctggggc ttgcttccct tcgcccgtgg caacatccac    1920
attagctcca atgacccgac tgctcccgcc gccatcaacc ctaactactt tatgttcgaa    1980
tgggacggca agagccaggc cggtatcgcc aagtacatca ggaagattct ccgcagcgca    2040
ccattgaaca aacttattgc gaaggaaacc aagcccggtc tctctcgcat tccggccact    2100
gctgcggatg agaagtgggt tgaatggctc aaggctaact atcgttccaa cttccacccc    2160
gtcggaactg ctgccatgat gcctcgttcc attggtggcg ttgttgataa ccgtctccgg    2220
gtctatggta ccagcaatgt tcgcgtcgta gatgcgtctg tcctgccctt ccaggtttgc    2280
ggccacttgg ttagcacgct ttatgccgtt gccgagcgcg cttccgactt gattaaggag    2340
gatgcgaaga gtgcttag                                                 2358
```

FUSION PROTEIN OF FLAVIN ADENINE DINUCLEOTIDE-GLUCOSE DEHYDROGENASE AND CYTOCHROME MOLECULE

TECHNICAL FIELD

The present disclosure relates to a fusion protein comprising a fungus-derived FADGDH and a cytochrome molecule linked to the N terminus of the FADGDH.

REFERENCES TO THE SEQUENCE LISTING

Reference to the sequence listing that was submitted as an ASCII text file. The sequence listing consists of a file named "JPOXMLDOC01-seql.txt," (160 kilobytes), created on Mar. 8, 2019. The sequence listing appendix is incorporated herein by reference in its entirety.

BACKGROUND ART

In the treatment of diabetes, there is a case in which a diabetic patient needs to control his or her blood glucose level (self-monitoring blood glucose (SMBG)). Nowadays, SMBG has become an important health management method in the treatment of diabetes.

Nowadays, a variety of SMBG methods have been developed and reported. Examples thereof include a method in which an enzyme that uses blood glucose as a substrate is used as a sensing element. According to this method, the sensing element enzyme catalyzes a reaction using blood glucose as a substrate, and the resulting electrons are transferred to an electrode through an electron mediator, thereby generating a current. The level of glucose in the blood may be quantified by measuring the magnitude of the current. Enzymes that are used as sensing elements include glucose oxidase, pyrroloquinoline quinone glucose dehydrogenase (PQQGDH), flavin adenine dinucleotide glucose dehydrogenase (FADGDH), and the like (Patent Documents 1 and 2).

In addition, the use of a fusion protein including the enzyme and a cytochrome molecule as a sensing element has also been reported and reviewed.

Patent Document 3 reported constructing a modified PQQGDH by linking the cytochrome c domain of PQQ ethanol dehydrogenase (PQQEDH), which uses PQQ as a coenzyme, at the gene level to the carboxyl terminus of the PQQGDH, and reported that the fusion protein had direct electron transfer (DET) ability. In addition, Non-Patent Document 1 reported that a fusion protein obtained by connecting the bacteria-derived cytochrome c to the C-terminus of the catalytic subunit of the bacteria-derived FADGDH has DET ability.

In addition, an attempt to link a cytochrome molecule to a fungus-derived FADGDH has not yet been reported.

PRIOR ART DOCUMENTS

Patent Documents

Patent Document 1: Japanese Patent Application Laid-Open No. 2012-210212
Patent Document 2: WO2009/037838
Patent Document 3: Japanese Patent Application Laid-Open No. 2014-207911

Non-Patent Documents

Non-Patent Document 1: J. Am. Chem. Soc., 2017, 139 (48), pp. 17217-17220

DISCLOSURE

Technical Problem

In a fungus-derived FADGDH, the coenzyme FAD is buried deep in the protein molecule. For this reason, in the absence of an external electron acceptor (mediator), (dehydrogenation) of glucose FAD reduced by oxidation cannot be oxidized by an electrode to obtain electrons. With the aim of achieving the above objective, it has been attempted to impart DET ability to fungus-derived FADGDHs by elaborately modifying carbon nanotubes or gold nanoparticles on electrodes or enzymes. However, since there is an error in the interpretation of the obtained phenomenon or a complex chemical modification process is required, good results have not been obtained until now.

Furthermore, GDH or EDH using the above-described PQQ as a coenzyme has a completely different structure from a fungus-derived GDH. In addition, for a fusion protein comprising PQQEDH and a cytochrome molecule, the molecular surface, to which the coenzyme PQQ is bound, has a structure in which the Si side is widely open toward PQQ. For this reason, it is considered that the cytochrome molecule is particularly easy to access, and the fusion protein exhibits DET ability due to the above-described structure.

In addition, for the fusion protein comprising a bacteria-derived FADGDH and a bacteria-derived cytochrome c, iron sulfur clusters present in the bacteria-derived FADGDH accept electrons from FAD, and furthermore, transfer the accepted electrons to cytochrome c or other external electron acceptors (Bio electro chemistry Volume 112, December 2016, Pages 178-183). That is, it is considered that the DET ability in the fusion protein is based on the iron sulfur clusters in the bacteria-derived FADGDH, and is a unique phenomenon based on the enzyme. In addition, it is considered that the bacteria-derived FADGDH has a remarkably different primary structure from the fungus-derived FADGDH, and that the three-dimensional structures of the two proteins differ from each other.

From the above, a fungus-derived FADGDH having direct electron transfer ability has not yet been obtained. Therefore, an objective of the present disclosure is to provide a fungus-derived FADGDH having direct electron transfer ability.

Technical Solution

The present inventors have worked hard to solve the above problem, and as a result, have found that a fusion protein comprising a fungus-derived flavin adenine dinucleotide glucose dehydrogenase (FADGDH) and a cytochrome molecule linked to the N-terminus of the FADGDH enables direct electron transfer without requiring an electron mediator.

The present disclosure is based on the above understanding, and includes the following inventions.

A fusion protein comprising: a fungus-derived flavin adenine dinucleotide glucose dehydrogenase (FADGDH) or a variant (or mutant) thereof; and a cytochrome molecule linked to the N-terminus of the FADGDH or variant thereof.

[2] The fusion protein of [1], wherein the FADGDH is an FADGDH derived from *Aspergillus* sp., *Botryotinia* sp., *Mucor* sp., *Parasitella* sp., or *Rhizopus* sp.

[3] The fusion protein of [1] or [2], wherein the cytochrome molecule is derived from *E. coli* or oxidoreductase.

[4] The fusion protein of any one of [1] to [3], wherein the cytochrome molecule is cytochrome b.

[5] The fusion protein of any one of [1] to [4] of any one of the following (a) to (c):
  (a) a protein which consists of the amino acid sequence set forth in at least one of SEQ ID NOs: 2, 3 and 13 to 21;
  (b) a protein which consists of an amino acid sequence resulting from deletion, substitution, insertion or addition of one amino acid or a plurality of amino acids in the amino acid sequence (a), and which has glucose dehydrogenase activity and electron transfer function; and
  (c) a protein which consists of an amino acid sequence having a sequence identity of 80% or higher to the amino acid sequence and which (a), has glucose dehydrogenase activity and electron transfer function.

[6] A gene encoding the fusion protein of any one of [1] to [5].

[7] A vector comprising the gene of [6].

[8] A transformant comprising the gene of [6].

[9] A transformant in which the gene of [6] is integrated into the main chromosome of the transformant.

[10] An enzyme electrode comprising the fusion protein of any one of [1] to [5] attached thereto.

[11] A method for measuring glucose concentration in a sample, the method comprising:
  bringing the sample into contact with the enzyme electrode of [10]; and
  measuring electrons generated by oxidation of glucose.

[12] A glucose sensor which uses the enzyme electrode of [10] of as a working electrode.

The present specification includes the contents disclosed in the specification and/or drawings of Japanese Patent Application No. 2018-042275 based on which the present application claims priority.

All publications, patents and patent applications mentioned in the present disclosure are incorporated herein by reference in their entirety.

Advantageous Effects

According to the present disclosure, there may be provided a fungus-derived FADGDH having direct electron transfer ability.

DESCRIPTION OF DRAWINGS

FIG. 1 illustrates the amino acid sequence (SEQ ID NO: 1) of a fusion protein (BFU/b562) obtained by linking *E. coli*-derived cytochrome b562 (b562) to the C-terminus of a fungus-derived FADGDH (BFU) via a linker sequence. The boxed sequence indicates the linker sequence, and the underlined portion indicates the sequence of b562.

FIG. 2A illustrates the amino acid sequence (SEQ ID NO: 2) of a fusion protein (b562/BFU) obtained by linking *E. coli*-derived cytochrome b562 (b562) to the N-terminus of a fungus-derived FADGDH (BFU) via a linker sequence. The boxed sequence indicates the linker sequence, and the underlined portion indicates the sequence of b562.

FIG. 2B illustrates the amino acid sequence (SEQ ID NO: 13) of a fusion protein (b562/BFU wild-type) obtained by linking *E. coli*-derived cytochrome b562 (b562) to the N-terminus of a fungus-derived FADGDH (BFU wild-type) via a linker sequence. The boxed sequence indicates the linker sequence, and the underlined portion indicates the sequence of b562.

Figure 3:
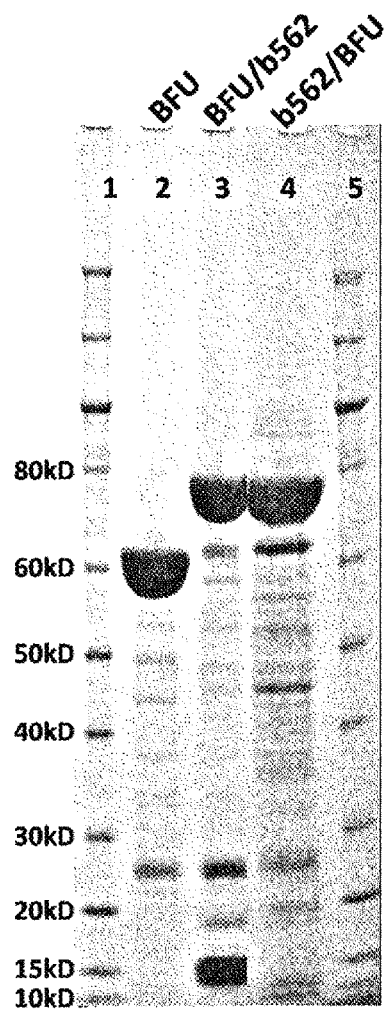
FIG. 3 is a photograph illustrating the results of SDS-PAGE analysis of the fungus-derived FADGDH (BFU), fusion protein (BFU/b562) and fusion protein (b562/BFU) expressed in transformants.

(A) illustrates the response results obtained when adding glucose at various concentrations. (B) illustrates a calibration curve.

FIG. 6A illustrates the amino acid sequence (SEQ ID NO: 3) of a fusion protein (PcCDH heme-AfGDH) obtained by linking the cytochrome of domain fungal cellobiose dehydrogenase to the N-terminus of a fungus-derived FADGDH (AfGDH) via a linker sequence. The underlined portion indicates the sequence of the cytochrome domain, and the boxed sequence indicates the linker sequence. This sequence lacks the N-terminal signal sequence of the cytochrome domain, and the signal sequence of an α-factor derived from an expression vector may be added.

FIG. 6B illustrates the amino acid sequence (SEQ ID NOs: 14 and 15) of a fusion protein (PCCDH heme-AfGDHGlu346Lys or Arg) obtained by linking the cytochrome domain of fungal cellobiose dehydrogenase to the N-terminus of a fungus-derived FADGDH (AfGDHGlu346Lys or Arg) via a linker sequence. The underlined portion indicates the sequence of the cytochrome domain, and the boxed sequence indicates the linker sequence. The bold letter indicates mutation. This sequence lacks the N-terminal signal sequence of the cytochrome domain, and the signal sequence of an α-factor derived from an expression vector may be added.

FIG. 6C illustrates the amino acid sequence (SEQ ID NOs: 16 and 17) of a fusion protein (PCCDH heme-AfGDHAsn430Lys or Arg) obtained by linking the cytochrome domain of fungal cellobiose dehydrogenase to the N-terminus of a fungus-derived FADGDH (AfGDHAsn430Lys or Arg) via a linker. The underlined portion illustrates the sequence of the cytochrome domain, and the boxed sequence indicates the linker sequence. The underlined portion indicates the sequence of the cytochrome domain, and the boxed sequence illustrates the linker sequence. The bold letter indicates mutation. This sequence lacks the N-terminal signal sequence of the cytochrome domain, and the signal sequence of an α-factor derived from an expression vector may be added.

FIG. 6D illustrates the amino acid sequence (SEQ ID NOs: 18 and 19) a of fusion protein (PcCDH heme-AfGDHThr498Lys or Arg) obtained by linking the cytochrome domain of fungal cellobiose dehydrogenase to the N-terminus of a fungus-derived FADGDH (AfGDHThr498Lys or Arg) via a linker. The underlined portion indicates the sequence of the cytochrome domain, and the boxed sequence indicates the linker sequence. The bold letter indicates mutation. This sequence lacks the N-terminal signal sequence of the cytochrome domain, and the signal sequence of an α-factor derived from an expression vector may be added.

FIG. 6E illustrates the amino acid sequence (SEQ ID NOS: 20 and 21) of a fusion protein (PcCDH heme-AfGDHGlu504Lys or Arg) obtained by linking the cytochrome domain of fungal cellobiose dehydrogenase to the N-terminus of a fungus-derived FADGDH (AfGDHGlu504Lys or Arg) via a linker. The underlined portion indicates the sequence of the cytochrome domain, and the boxed sequence indicates the linker sequence. The bold letter indicates mutation. This sequence lacks the N-terminal signal sequence of the cytochrome domain, and the signal sequence of an α-factor derived from an expression vector may be added.

Figure 7:
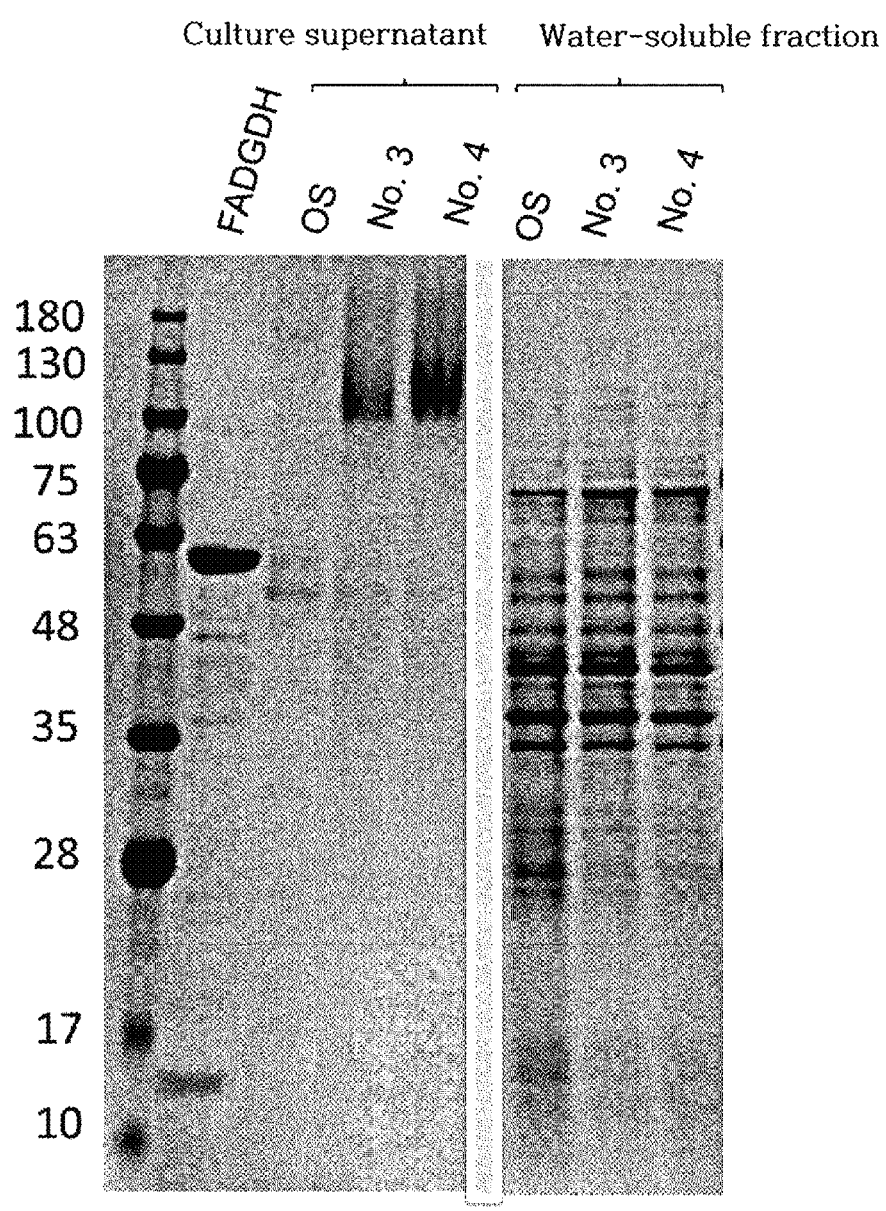

FIG. 7 is a photograph illustrating the results of SDS-PAGE analysis of the culture supernatant fraction of each of non-transformed host cells (OS), and transformants (sample No. 3 and No. 4) introduced with a gene encoding a fusion protein (PcCDH heme-AfGDH), and each water-soluble fraction obtained after dialyzing each of the supernatants.

Figure 8:
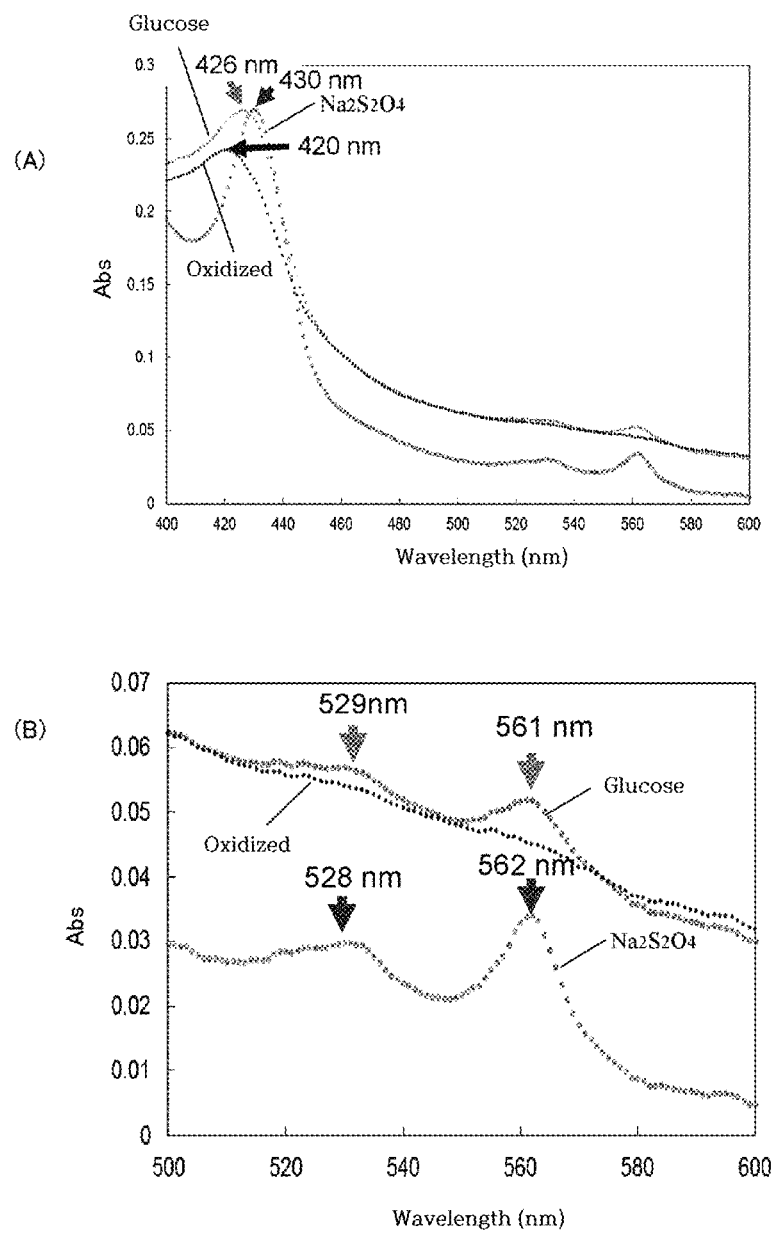

FIG. 8 illustrates the results of measuring the UV-VIS spectrum of a fusion protein (PcCDH heme-AfGDH) at 400 to 600 nm.

(A) illustrates the results of measurement in the range of 400 to 600 nm, and (B) illustrates the results of measurement in the range of 500 to 600 nm.

Figure 9:
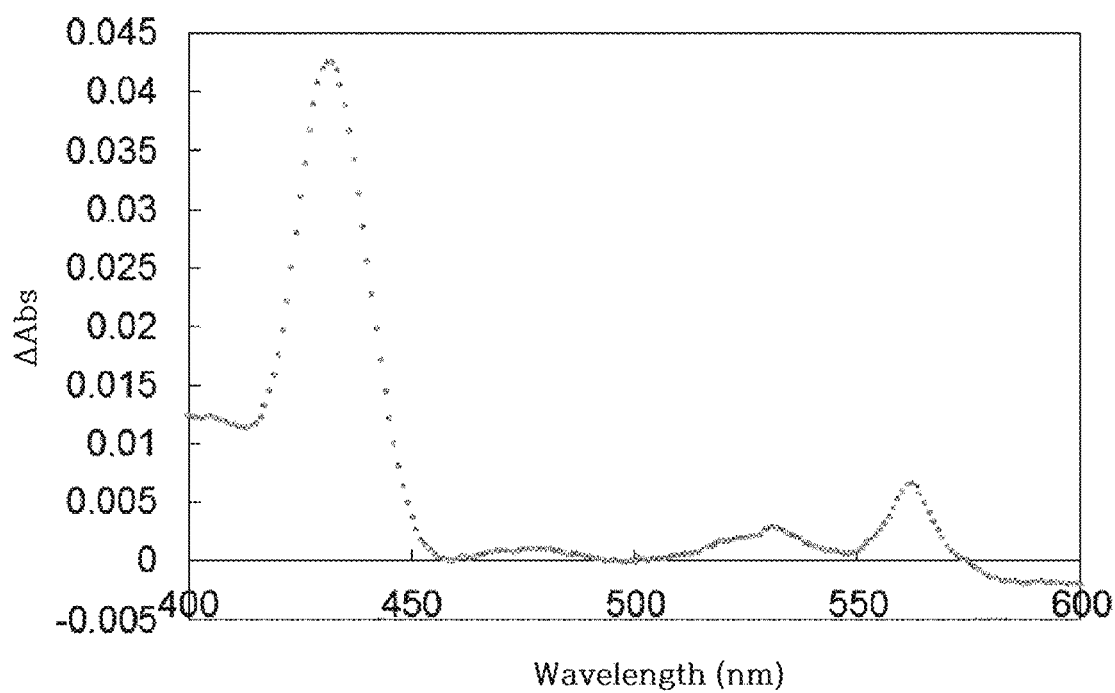

FIG. 9 illustrates the spectral difference in the UV-VIS spectral measurement (400 to 600 nm) of a fusion protein (PCCDH heme-AfGDH) between before and after addition of glucose.

Figure 10:
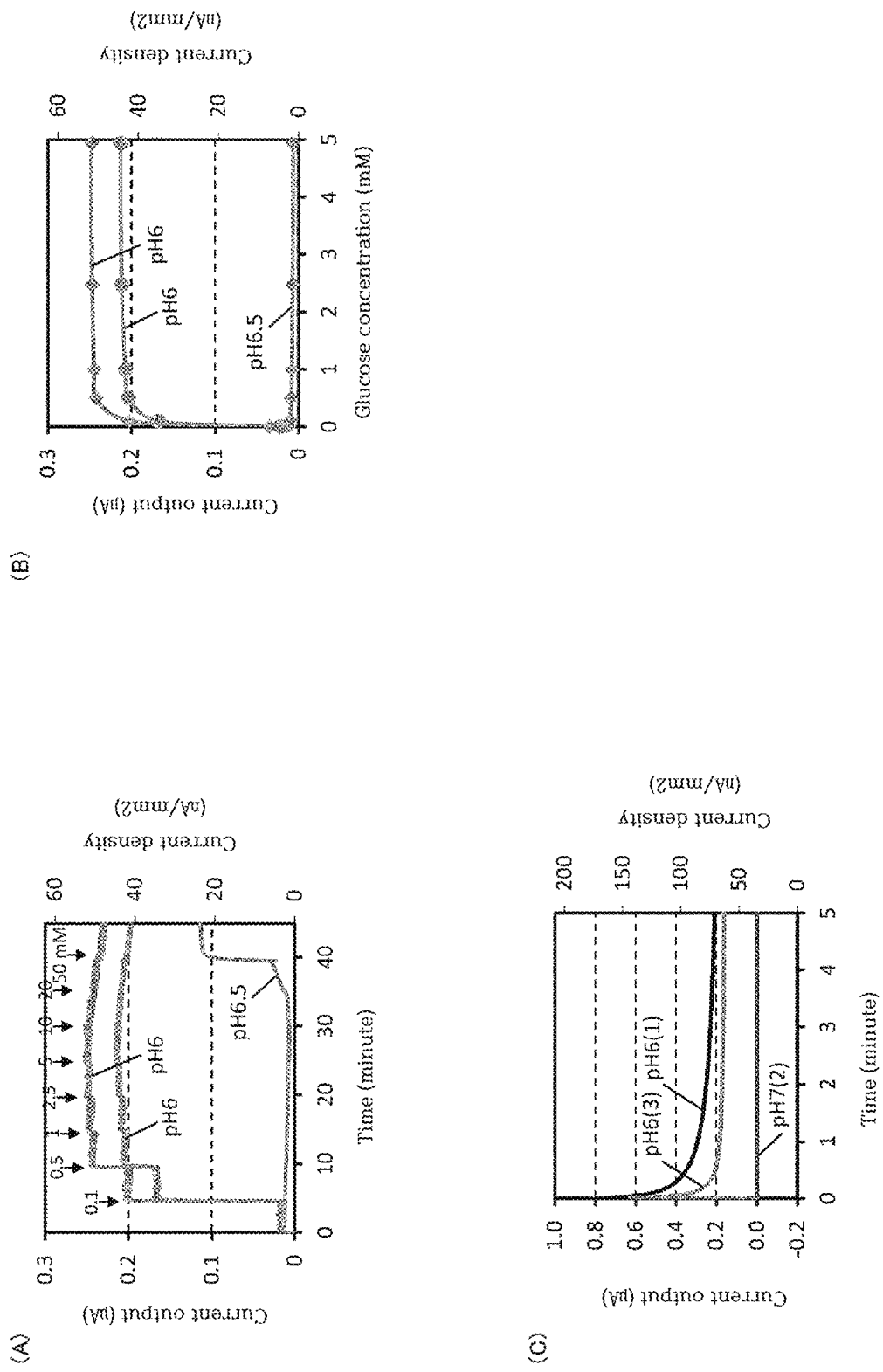

FIG. 10 depicts graphs illustrating the results of electrochemical measurement performed using electrodes having a fusion protein (PcCDH heme-AfGDH) immobilized thereon.

(A) illustrates the response results obtained when adding glucose at various pHs, and (B) illustrates a calibration curve.

(A) and (B) illustrate the results of electrochemical measurement at pH 6, performed using two separately fabricated electrodes. (C) illustrates the response results obtained when changing the pH of the reaction solution in the order of (1) pH 6, (2) pH 7, and (3) pH 6.

Figure 11:
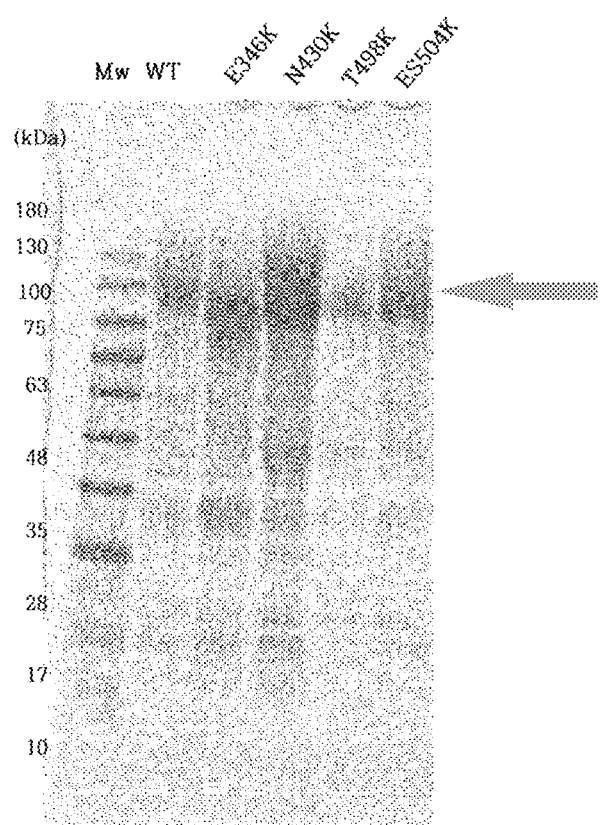

FIG. 11 is a photograph illustrating the results of SDS-PAGE of a wild-type AfGDH fusion protein and fusion proteins including AfGDH variants (E346K, N430K, T498K, and E504K), expressed in transformants.

Figure 12:
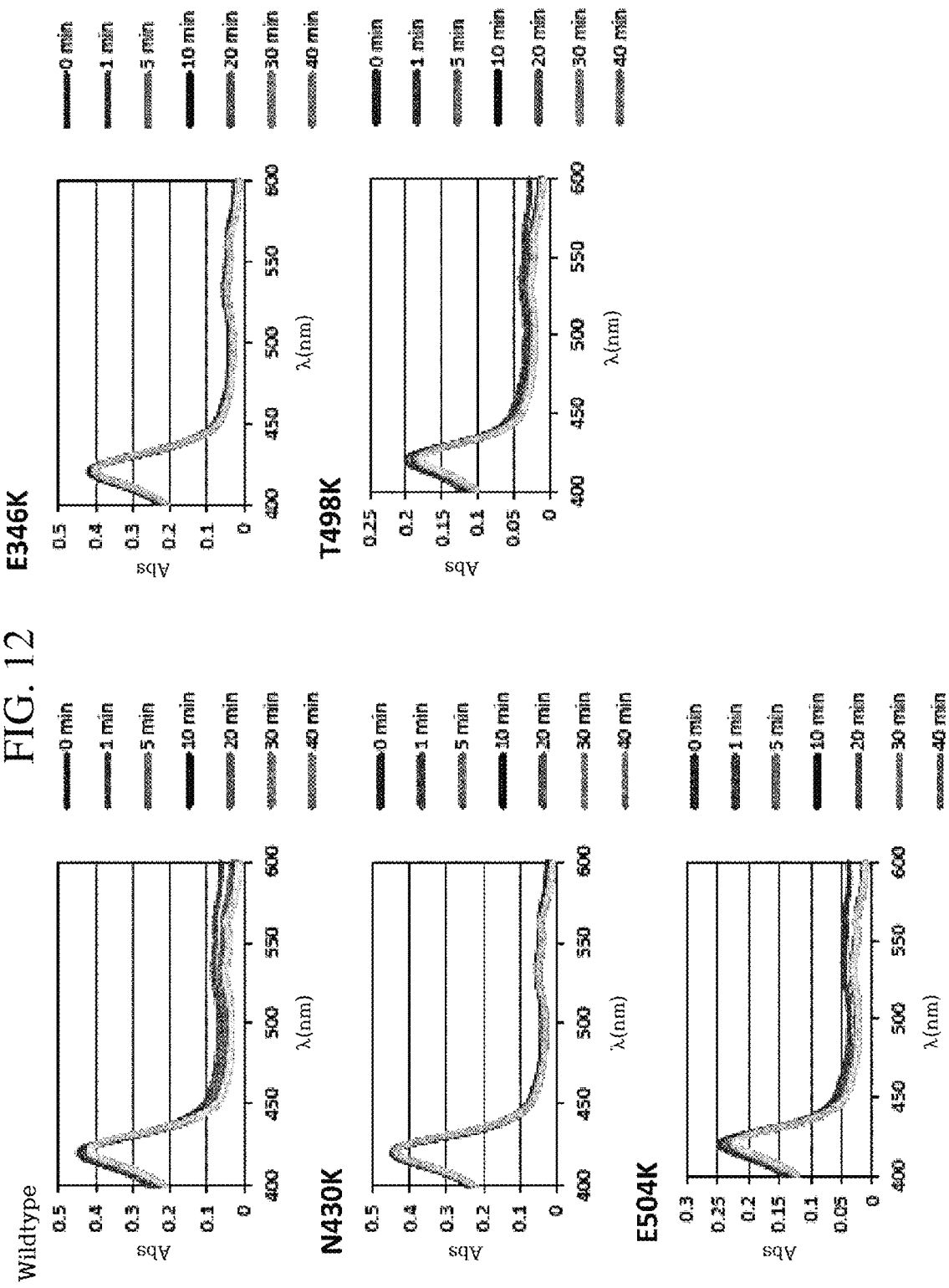

FIG. 12 illustrates the results of measuring the UV-VIS spectra (400 to 600 nm) of a wild-type AfGDH fusion protein and fusion proteins including AfGDH variants (E346K, N430K, T498K, and E504K).

Figure 13:
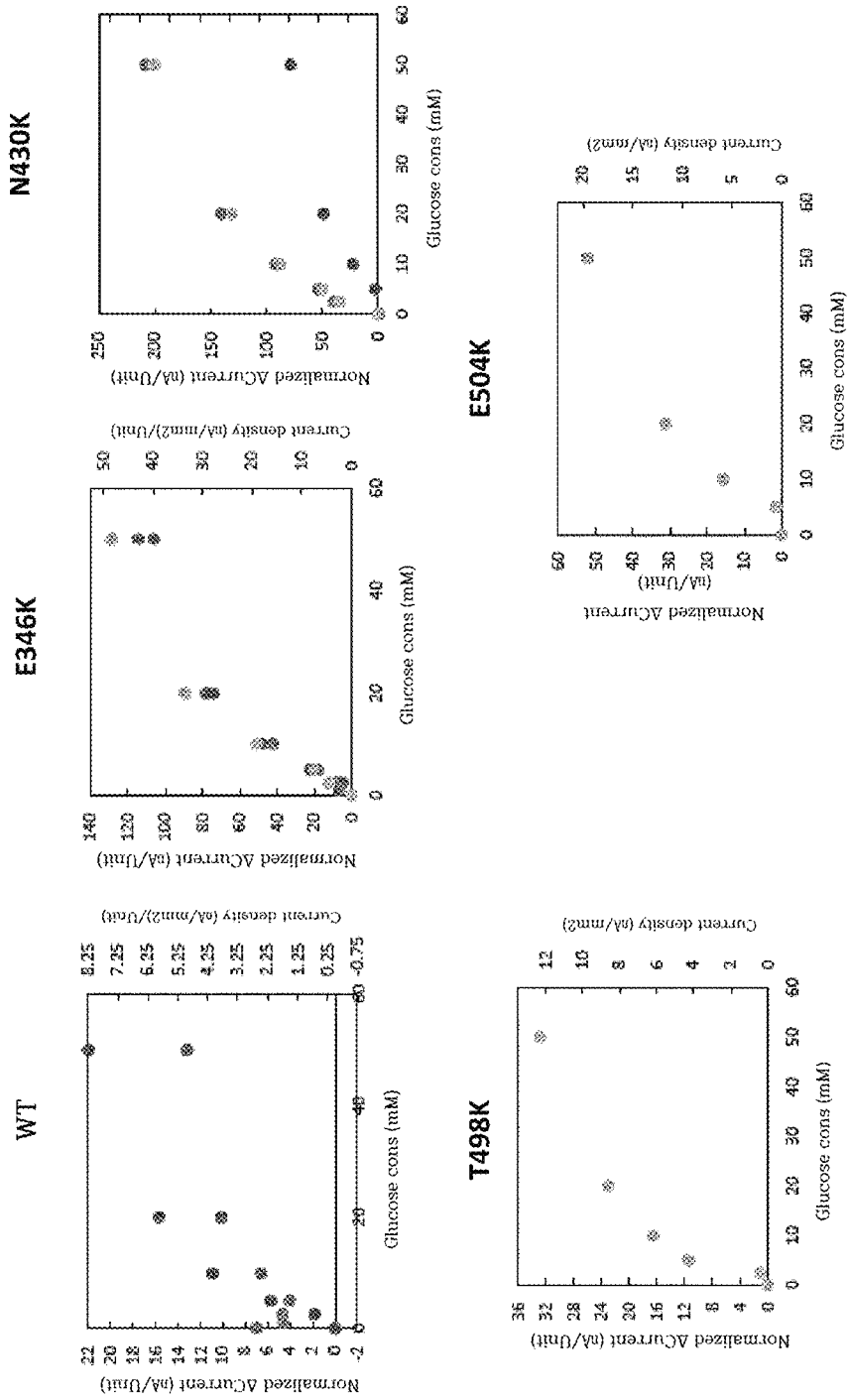

FIG. 13 depicts graphs illustrating the results of electrochemical measurement at pH 6, performed using a wild-type AfGDH fusion protein and fusion proteins including AfGDH variants (E346K, N430K, T498K, and E504K).

MODE FOR INVENTION

1. Fusion Protein

The fusion protein of the present disclosure is a fusion protein comprising: a fungus-derived FADGDH or a variant thereof; and a cytochrome molecule linked to the N-terminus of the FADGDH or variant thereof.

Flavin adenine dinucleotide glucose dehydrogenase (FADGDH) is a glucose dehydrogenase that uses flavin adenine dinucleotide (FAD) as a coenzyme, and has an activity of catalyzing a reaction that produces gluconolactone by oxidizing glucose in the presence of an electron acceptor.

In the present disclosure, FADGDH is a fungus-derived FADGDH. As the fungus-derived FADGDH, one derived from *Aspergillus* sp., *Botryotinia* sp., *Sclerotinia* sp., *Glomerella* sp., *Mucor* sp., *Parasitella* sp., *Rhizopus* sp., *Penicillium* sp., *Trichoderma* sp., *Colletotrichum* sp., *Talaromyces* sp., *Absidia* sp., *Actinomucor* sp., *Circinella* sp., *Aureobasidium* sp., *Kabatiella* sp., *Cladosporium* sp., *Fusicladium* sp., *Dumontinia* sp., *Ovulinia* sp., *Sclerotinia* sp., *Botrytis* sp., *Ciborinia* sp., or the like may be used. Among them, an FADGDH derived from *Aspergillus* sp., *Botryotinia* sp., *Mucor* sp., *Parasitella* sp., or *Rhizopus* sp. may be very properly used. In particular, the fungus-derived FADGDH is preferably FADGDH derived from *Aspergillus flavus*, *Botryotinia fuckeliana*, *Mucor prainii*, *Mucor circinelloides*, *Mucor subtilissimus*, *Mucor guilliermondii*, *Mucor javanicus*, *Parasitella parasitica*, *Rhizopus microspores*, or the like.

Fungus-derived FADGDHs are known. Sequence information on the FADGDH derived from *Aspergillus flavus* is available from known databases. For example, the sequence information is available under XP_002372599.1 from the database of NCBI (National Center for Biotechnology Information). Furthermore, sequence information on the FADGDH derived from *Botryotinia fuckeliana* is disclosed in WO2012/001976. In addition, sequence information on the FADGDHs derived from *Mucor prainii*, *Mucor guilliermondii* and *Mucor hiemalis* NBRC6754 are disclosed in Japanese Patent Application Laid-Open Nos. 2014-18096, 2017-000137 and 2015-84676, respectively. In the present disclosure, these known FADGDHs may also be used.

According to one aspect, an FADGDH that may be used in the present disclosure may be an FADGDH comprising or consisting of a protein represented by SEQ ID NO: 4 (FADGDH derived from *Aspergillus flavus*), SEQ ID NO: 5 (FADGDH derived from *Botryotinia fuckeliana*) SEQ ID NO: 6 (FADGDH derived from *Mucor prainii*).

In addition, the FADGDH in the present disclosure also includes a variant thereof, as long as it retains the catalytic activity. The variant of the FADGDH may generally be represented by the following (I) or (II):

(I) a protein which consists of an amino acid sequence resulting from deletion, substitution, insertion or addition of one amino acid or a plurality of amino acids in the amino acid sequence of the FADGDH, and which has the catalytic activity; and (II) a protein which consists of an amino acid sequence having a sequence identity of 80% or higher to the amino acid sequence of the FADGDH, and which has the catalytic activity.

The "plurality of amino acids" in (I) refers to about 2 to 120, preferably about 2 to 60, more preferably about 2 to 30 amino acids.

In addition, the "sequence identity" in (II) may be obtained according to a known sequence comparison method. For example, the sequence identity may be obtained by using BLAST (Basic Local Alignment Search Tool at the National Center for Biological Information), for example, as a default setting. The "sequence identity of 80% or higher" refers to a sequence identity of, for example, 85% or higher, preferably 90% or higher, more preferably 95% or higher, even more preferably 99% or higher.

Variants of the FADGDH include known FADGDH variants. These variants include variants of *Aspergillus flavus*-derived FADGDH, which are disclosed in WO2013/164477 and Japanese Patent Application Laid-Open Nos. 2016-208915, 2016-7193 and 2016-7192; variants of *Botryotinia fuckeliana*-derived FADGDH, which are disclosed in WO2012/001976; variants of *Mucor prainii*-derived FADGDH, which are disclosed in WO2016/076364, Japanese Patent Application Laid-Open No. 2015-084676, WO2015/129475, WO2015/099112, WO2013/065770, WO2012/169512, WO2012/073987, WO2012/073986, and WO2010/140431; and variants of FADGDHS derived from other fungi, which are disclosed in WO2014/045912, WO2013/147206, WO2013/031664 and Japanese Patent Application Laid-Open Nos. 2016-208916, 2016-7191 and 2015-167506, and these disclosed variants may be used. According to an aspect, an FADGDH variant that may be used in the present disclosure may comprise or consist of a protein represented by an amino acid sequence having one or more mutations selected from the group consisting of Glu346Lys or Arg, Asn430Lys or Arg, Thr498Lys or Arg, and Glu504Lys or Arg in the amino acid sequence of *Aspergillus flavus* FADGDH (e.g., the amino acid sequence of SEQ ID NO: 4). In other embodiments, an FADGDH variant that may be used in the present disclosure may comprise or consist of a protein represented by the amino acid sequence of at least one of SEQ ID NO: 7 and SEQ ID NOs: 22 to 25.

The "cytochrome molecule" refers to a heme protein functioning as an electron carrier, and in particular, it refers to a protein molecule to which one or more heme irons are covalently or non-covalently bound. In addition, the "cytochrome molecule" in the present disclosure also includes a part of a protein that retains electron transfer function, called an electron transfer subunit, a heme-containing domain, or a quinohemoprotein subunit or domain in oxidoreductase. Hereinafter, a part of the protein that retains electron transfer function is sometimes referred to as a "cytochrome domain". Examples of the oxidoreductase include, but are not limited to, cellobiose dehydrogenase, ethanol dehydrogenase, oligosaccharide dehydrogenase, and the like.

Various kinds of cytochrome molecules have been isolated and identified from various organisms. In the present disclosure, any cytochrome molecule may be used without particular limitation. Preferably, cytochrome b is used.

For example, cytochrome molecules that may be used in the present disclosure include cytochrome molecules derived from bacteria. The bacteria include, but are not limited to, *Escherichia* sp., *Pseudomonas* sp., *Acinetobacter* sp., *Klebsiella* sp., *Salmonella* sp., *Yersinia* sp., *Pasteurella* sp., *Rhizobium* sp., *Comamonas* sp., and the like. Preferably, a cytochrome molecule derived from *Escherichia coli, Pseudomonas stutzeri, Acinetobacter calcoaceticus, Klebsiella pneumoniae, Salmonella typhi, Salmonella typhinulium*, or *Yersinia pestis* may be used. In particular, cytochrome b562 derived from *Escherichia coli* is preferably used. Cytochrome molecules derived from bacteria are known. Sequence information on cytochrome b562 is available from known database. For example, the sequence information is available under WP_057688639.1 from the database of NCBI. In the present disclosure, these known cytochrome molecules derived from bacteria may also be used.

In addition, examples of cytochrome molecules that may be used in the present disclosure include the cytochrome domains of oxidoreductases derived from fungi or bacteria. The fungi include, but are not limited to, filamentous fungi, such as *Phanerochaete* sp., *Grifola* sp., *Pycnoporus* sp., *Trametes* sp., *Humicola* sp., *Thielavia* sp., *Irpex* sp., *Schizophyllum* sp., *Coniophora* sp., and *Sclerotium* sp. Examples of the bacteria include the above-described bacteria. Preferably, the cytochrome molecule of cellobiose dehydrogenase derived from filamentous fungi, such as *Phanerochaete* sp., *Grifola* sp., *Pycnoporus* sp., *Trametes* sp., *Humicola* sp., or *Thielavia* sp., may be used. In particular, the cytochrome molecule is preferably the cytochrome domain of cellobiose dehydrogenase from *Phanerochaete chrysosporium, Grifola frondosa, Pycnoporus cinnabarinus, Trametes versicolor, Humicola insolens*, or *Thielavia heterothallica*.

The cytochrome domains of oxidoreductases from fungi or bacteria are known. Sequence information on cellobiose dehydrogenase from *Phanerochaete chrysosporium* is available from known databases. For example, the sequence information is available under GenBank: AAB61455.1, GenBank: AAC49277.1, or the like. In the present disclosure, these known cytochrome domains of oxidoreductases from fungi or bacteria may also be used.

According to an aspect, a cytochrome molecule that may be used in the present disclosure may comprise or consist of a protein represented by the amino acid sequence of SEQ ID NO: 8 (the amino acid sequence of cytochrome b562 from *E. coli*) or SEQ ID NO: 9 (the amino acid sequence of the cytochrome domain (classified as cytochrome b) of cellobiose dehydrogenase from *Phanerochaete chrysosporium*).

In addition, the cytochrome molecule in the present disclosure also includes a variant thereof, as long as it retains electron carrier function. A variant of the cytochrome molecule may be represented by the following (i) or (ii):

(i) a protein which consists of an amino acid sequence resulting from deletion, substitution, insertion or addition of one amino acid or a plurality of amino acids in the amino acid sequence of the cytochrome molecule, and which has the above-described function; and (ii) a protein which consists of an amino acid sequence having a sequence identity of 80% or higher to the amino acid sequence of the cytochrome molecule, and which has the above-described function.

The "plurality of amino acids" in (i) refers to 2 to 40, preferably 2 to 20, more preferably 2 to 10 amino acids.

In addition, the "sequence identity" in (ii) is as defined above. The "sequence identity of 80% or higher" refers to a sequence identity of, for example, 85% or higher, preferably 90% or higher, more preferably 95% or higher, even more preferably 99% or higher.

In the present disclosure, regarding the "linking", the FADGDH or variant thereof and the cytochrome molecule may be bound directly to each other or may be bound to each other via a linker sequence.

As the linker sequence, a peptide linker may be used, and the number and type of amino acids thereof are not particularly limited. For example, a linker sequence having about 1 to 100 amino acids, preferably about 5 to 50 amino acids, or particularly preferably about 10 to 30 amino acids may be used. As the linker sequence, any peptide linker known in the related art may be used, or the loop sequence of oxidoreductase may be very preferably used. For example, a polypeptide comprising an amino acid sequence (e.g., the amino acid sequence represented by SEQ ID NO: 12) selected from the loop sequence of cellobiose dehydrogenase from *Phanerochaete chrysosporium* may be used as the peptide linker.

In one embodiment of the fusion protein of the present disclosure, the fusion protein comprises an FADGDH or from *Botryotinia fuckeliana* or a variant thereof and cytochrome b562 from *E. coli*, and has a structure in which the cytochrome b562 and the FADGDH are sequentially linked at the N terminus via a linker. One embodiment of this fusion protein may have a structure illustrated in at least one of FIGS. 2A and 2B.

In other embodiments of the fusion protein of the present disclosure, the fusion protein comprises an FADGDH from *Aspergillus flavus* or a variant thereof and a cytochrome domain of cellobiose dehydrogenase from *Phanerochaete chrysosporium*, and has a structure in which the cytochrome domain and the FADGDH are sequentially linked at the N terminus via a linker. One embodiment of this fusion protein may have a structure illustrated in at least one of FIGS. 6A to 6E.

The fusion protein of the present disclosure is a protein having glucose dehydrogenase activity in the moiety of the FADGDH or the variant thereof and having electron transfer function in the cytochrome molecule moiety. The moiety of the FADGDH or the variant thereof recognizes glucose and catalyzes the redox reaction thereof, and electrons generated by the redox reaction are transferred to the heme of the cytochrome molecule by internal electron transfer (IET), and then transferred directly to an external electron acceptor.

According to an aspect, the fusion protein of the present disclosure comprises or consists of (a) an amino acid sequence set forth in at least one of SEQ ID NOs: 2, 3 and 13 to 21.

In addition, the fusion protein in the present disclosure also includes a variant thereof, as long as it retains the glucose dehydrogenase activity and electron transfer function. The variant may generally be represented by the following (b) or (c):

(b) a protein which consists of an amino acid sequence resulting from deletion, substitution, insertion or addition of one amino acid or a plurality of amino acids in the amino acid sequence of (a), and which has glucose dehydrogenase activity and electron transfer function;

(c) a protein which has a sequence identity of 80% or higher to the amino acid sequence of (a) and which has glucose dehydrogenase activity and electron transfer function.

The "plurality of amino acids" in (b) refers to 2 to 160, preferably 2 to 80, more preferably 2 to 40 amino acids.

In addition, the "sequence identity" in (c) is as defined above. The "sequence identity of 80% or higher" refers to a sequence identity of, for example, 85% or higher, preferably 90% or higher, more preferably 95% or higher, even more preferably 99% or higher.

Preferably, if the amino acid residues at positions 538, 622, 690 and 696 in SEQ ID NOs: 14 to 21 are Lys or Arg, any of the amino acid residues (Lys or Arg) at these positions does not change.

The fusion protein of the present disclosure may have, at the N-terminus or C-terminus thereof, an additional sequence such as a tag sequence (e.g., a histidine tag sequence, etc.) for purification or a signal sequence (e.g., an α-factor secretion signal sequence) for secretion, if necessary.

2. Method for Production of Fusion Protein

Production of the fusion protein may be performed based on a general gene recombination method known to those skilled in the art (Green, M. R. and Sambrook, J., 2012, Molecular Cloning: A Laboratory Manual Fourth Ed., Cold Spring Harbor Laboratory Press, Cold Spring Harbor, New York).

That is, the fusion protein of the present disclosure may be obtained by inserting a nucleic acid encoding the fusion protein a into suitable expression vector, introducing and expressing the nucleic acid in a suitable host cell, and isolating and purifying the expressed fusion protein. As used herein, the "nucleic acid" refers to DNA, RNA, a DNA/RNA hybrid, and the form thereof is not particularly limited as long as it encodes a desired protein.

The nucleic acid encoding the fusion protein of the present disclosure may be produced by linking a nucleic acid encoding the FADGDH or the variant thereof in-frame to a nucleic acid encoding the cytochrome molecule, if necessary, through a nucleic acid encoding a linker.

The nucleic acid encoding each of the proteins may be prepared based on a general method known in the related art. For example, from a cDNA library or genome library prepared from cells containing each protein, PCR may be performed using primers designed and synthesized based on the nucleotide sequences of nucleic acids encoding each protein, whereby the desired nucleic acid may be amplified from the library and isolated. Since the primers may have restriction enzyme recognition sequences, the restriction enzyme recognition sequences may be provided in the nucleic acid isolated thereby, and inter-ligation and/or ligation to a vector may be performed d using the sequences. Alternatively, the nucleic acid encoding the fusion protein of the present disclosure may also be a chemically synthesized nucleic acid having a desired sequence. In addition, if desired mutation is introduced into each nucleic acid, a site-specific mutation introduction method using a PCR method may be used.

The obtained nucleic acids encoding each protein are linked into a suitable expression vector in a desired order by restriction enzymes and DNA ligases. The nucleic acid encoding the fusion protein of the present disclosure is operably linked to expression control sequences comprising a promoter. The "operably linked" means that the inserted nucleic acid is expressed under the control of a promoter in a host cell.

The expression vector may be any one capable of replicating or surviving in a host cell, and examples thereof include, but are not particularly limited to, plasmid vectors, phage vectors, cosmid vectors, phagemid vectors, viral vectors, etc. The promoter contained in the expression vector may be any promoter as long as it is appropriate for the host cell to be used. For example, if the host cell is *E. coli*, lac promoter, Trp promoter, PL promoter, PR promoter or the like may be used, and if the host cell is yeast, AOX1 promoter, TEF1 promoter, ADE2 promoter, CYC1 promoter, GAL-L1 promoter, or the like may be used. (However, the present disclosure is not limited thereto.)

The expression vector may additionally contain a selectable marker (e.g., an antibiotic resistance gene, an auxotrophic gene, etc.) for selecting transformants, a replication origin enabling replication in the host, an enhancer, a terminator region, a poly A addition signal, a tag sequence for purification, a signal sequence for secretion, or the like.

The host cell into which the expression vector is to be introduced may be any host cell that may express the fusion protein of the present disclosure. As the host cell, bacteria, fungi, insect cells, animal cells (e.g., mammalian cells), plant cells, or the like may be used. Preferably, the host cell is of the same type as the cell from which the cytochrome molecule is derived. If the cytochrome molecule is derived from bacteria, bacteria may preferably be used as the host cell, and if the cytochrome molecule is derived from fungi, fungi may preferably be used as the host cell. (However, the levels of the genus or species of the host cell and the cell from which the cytochrome molecule is derived may be the same or different.) For example, if the host cell is bacteria, *E. coli* may be used, and if the host cell is fungi, yeasts, such as *Pichia, Saccharomyces* or *Schizosaccharomyces*, or fungi, such as *Aspergillus* or *Trichoderma*, may be used.

Transformation of the host cell with the expression vector may be performed by a known method, such as a calcium phosphate method, an electroporation method, a lipofection method, a particle gun method, or a PEG method.

The transformed host cell may be cultured according to a conventional method. If the fusion protein of the present disclosure has a signal sequence for secretion and is secreted extracellularly after production by expression, a desired peptide may be recovered from the cell culture. Alternatively, a desired peptide accumulated in the cell may also be recovered. In this case, the cell is physically or chemically disrupted (e.g., by sonication, homogenization, lysis, etc.), and a desired peptide is recovered using protein purification technology.

The recovered fusion protein of the present disclosure may be purified by a conventional method, for example, chromatography, such as gel filtration chromatography, ion exchange column chromatography, affinity chromatography, reverse phase chromatography, or HPLC, ammonium sulfate fractionation, ultrafiltration, or immunoadsorption.

According to an aspect, the nucleic acid encoding the protein that may be used in production of the fusion protein of the present disclosure comprises or consists of (A) a polynucleotide represented by a nucleotide sequence represented by at least one of SEQ ID NOS: 10, 11 and 26 to 34. The nucleotide sequences represented by SEQ ID NOs: 10, 11, 26, 27, 28, 29, 30, 31, 32, 33 and 34 encode the amino acid sequences represented by SEQ ID NOs: 2, 3, 13, 14, 15, 16, 17, 18, 19, 20 and 21, respectively.

In addition, the nucleic acid protein of the present disclosure also includes a variant thereof, as long as it encodes a protein having glucose dehydrogenase activity and electron transfer function. A variant of the nucleic acid may generally be represented by at least one of the following (B) to (D):
  (B) a polynucleotide which consists of a nucleotide sequence resulting from deletion, substitution, insertion or addition of one nucleotide or a plurality of nucleotides in the nucleotide sequence of (A), and which has glucose dehydrogenase activity and electron transfer function;
  (C) a polynucleotide which consists of a nucleotide sequence having a sequence identity of 80% or higher to the nucleotide sequence of (A), and which has glucose dehydrogenase activity and electron transfer function; and
  (D) a polynucleotide which consists of a nucleotide sequence that hybridizes completely or at least 80% with a sequence complementary to the nucleotide sequence of (A) under stringent conditions, which and has glucose dehydrogenase activity and electron transfer function.

The "plurality of nucleotides" in (B) refers to 2 to 400, preferably 2 to 200, more preferably 2 to 100 nucleotides.

In addition, the "sequence identity" in (C) is as defined above. The "sequence identity of 80% or higher" refers to a sequence identity of, for example, 85% or higher, preferably 90% or higher, more preferably 95% or higher, even more preferably 99% or higher.

In addition, the "stringent conditions" in (D) refers to conditions under which a specific hybrid is formed whereas a non-specific hybrid is not formed. For example, the "stringent conditions" refers to conditions under which hybridization is performed in a solution containing 2 to 6×SSC (the composition of 1×SSC: 0.15 M NaCl, 0.015 M sodium citrate, and pH 7.0) and 0.1 to 0.5% SDS at 42 to 55° C., and washing is performed in a solution containing 0.1 to 0.2×SSC and 0.1 to 0.5% SDS at 55 to 65° C. The "80% or higher" refers to 85% or higher, preferably 90% or higher, more preferably 95% or higher, even more preferably 99% or higher, of the entire nucleotide sequence.

Preferably, if the amino acid residues at positions 538, 622, 690 and 696 in SEQ ID NOs: 14 to 21 are Lys or Arg, any of the amino acid resides (Lys or Arg) at these positions in the amino acid sequence encoded by the variant of the nucleic acid does not change.

3. Enzyme Electrode

The present disclosure also relates to an enzyme electrode having the fusion protein of the present disclosure immobilized thereon. The "enzyme electrode" refers to an electrode having an enzyme immobilized on the surface of an electrode, such as a gold electrode, a platinum electrode or a carbon electrode. The enzyme electrode may be widely used as a biosensor that uses the reaction specificity of an enzyme to specifically detect a variety 41 biologically active substances. The fusion protein immobilized on the surface of the enzyme electrode of the present disclosure recognizes the presence of an analyte (e.g., glucose) in a sample, and catalyzes the redox reaction of the analyte. The electrodes resulting from the redox reaction are transferred to the heme of the cytochrome molecule by internal electron transfer, and then transferred directly to the external electron acceptor electrode.

The enzyme electrode of the present disclosure may be fabricated by immobilizing the fusion protein of the present disclosure on the surface of an electrode. The method of immobilizing the fusion protein on the electrode surface may use one of a method using a crosslinking reagent, a method of encapsulating the fusion protein into a polymer matrix, a method of coating the fusion protein with a dialysis membrane, a method of immobilizing the fusion protein in a polymer, such as a photo-crosslinking polymer, an electrically conductive polymer or a redox polymer, and combinations thereof. Typically, fabrication of the enzyme electrode may be performed by immobilizing the fusion protein of the present disclosure on a carbon electrode using glutaraldehyde, and then blocking the glutaraldehyde by treatment with a reagent having an amine group. The obtained enzyme electrode may be used as a working electrode of a glucose sensor.

4. Glucose Sensor

The "glucose sensor" in the present disclosure refers to a measurement system for electrochemically measuring the concentration of glucose in a sample. Examples of the sample include blood samples, blood dialysis samples, blood, or blood or interstitial fluids.

The glucose sensor of the present disclosure may have a two-electrode structure comprising the enzyme electrode of the present disclosure as a working electrode and a counter electrode (e.g., a platinum electrode), or may have a three-electrode structure further comprising a reference electrode (e.g., an Ag/AgCl electrode). The working electrode may be one working electrode and may comprise a plurality of lines. The glucose sensor may further comprise a power source for applying a voltage to the working electrode, an ampere meter, a recorder, and a display unit. The configuration of the glucose sensor of the present disclosure is not particularly limited, and a known configuration (e.g., WO2005/030807, WO2005/023111, etc.) may be adopted. In addition, the glucose sensor of the present disclosure may also be referred to as being disposable.

5. Measurement of Glucose Concentration

Measurement of the glucose concentration using the glucose sensor of the present disclosure may be performed as follows. That is, as a working electrode, an enzyme electrode having the fusion protein of the present disclosure immobilized thereon is used, and as a counter electrode, a platinum electrode, for example, is used, and as a reference electrode, an Ag/AgCl electrode, for example, is used. After a constant voltage is applied to the working electrode and the current reaches a steady state, a sample is brought into contact with the enzyme electrode, and then electrons generated by the oxidation of glucose in the sample are measured using an increase in the current as an index. The glucose concentration in the sample may be calculated according to the calibration curve of the current increase, prepared using a standard-concentration glucose solution.

EXAMPLES

Hereinafter, the present disclosure will be described in detail with reference to examples, but the present disclosure is not limited to these examples.

Example 1: Fusion Protein Comprising Fungus-Derived FADGDH and Ethanol Dehydrogenase-Derived Cytochrome Molecule

(1) Construction of Fusion Protein

An examination of whether or not an enzyme having direct electron transfer (DET) ability could be constructed by linking a cytochrome molecule to a fungus-derived FADGDH was made. First, an examination of whether or not an enzyme having DET ability could be constructed by linking a cytochrome molecule at the gene level to the C-terminus of a fungus-derived FADGDH according to a previously reported configuration was made.

In addition, an examination of whether or not an enzyme having DET ability could be constructed by linking a cytochrome molecule at the gene level to the N-terminus of a fungus-derived FADGDH was made according to a completely new idea.

FIG. 1 illustrates the amino acid sequence of a fusion protein which is recombinantly produced based on a gene constructed by linking *E. coli*-derived cytochrome b562 at the gene level to the C-terminus of a fungus-derived FADGDH in this Example. In addition, the "fungus-derived FADGDH" used in this Example is a variant (BFU) of *Botryotinia fuckeliana*-derived glucose dehydrogenase (BFUGDH) (WO2012/001976).

It was aimed at constructing a fusion protein (BFU/b562) in which electron transfer from the FAD of GDH to the heme occurs, by linking cytochrome b562 to the C-terminus of the FADGDH via the loop sequence of quinohemoprotein ethanol dehydrogenase (QHEDH) from *Comamonas testosteroni* as a linker sequence.

In addition, FIG. 2A illustrates the amino acid sequence of a fusion protein which is recombinantly produced based on a gene constructed by linking *E. coli*-derived cytochrome b562 at the gene level to the N-terminus of a fungus-derived FADGDH in this Example.

It was aimed at constructing a fusion protein (b562/BFU) in which electron transfer from the FAD of GDH to the heme occurs, by linking cytochrome b562 to the N-terminus of the FADGDH via the loop sequence of cellobiose dehydrogenase from *Phanerochaete chrysosporium* as a linker sequence.

Genes encoding each fusion protein designed as described above were constructed, and each of the genes was inserted into the expression vector pET30c, thereby constructing fusion protein expression vectors. An *E. coli* BL21 (DE3) strain was transformed with each of the obtained expression vectors. As a control, transformation was performed using an expression vector comprising the FADGDH (Bfu)-encoding gene that does not comprise *E. coli*-derived cytochrome b562.

(2) Recovery of Fusion Protein and Evaluation of Enzymatic Activity

2-1. Recovery Method

*E. coli* transformed with each expression vector was precultured, and 1% was inoculated into 60 mL of a Km-containing autoinduction LB liquid medium in a 300-mL baffled flask, and then shake-cultured at 125 rpm at 20° C. for 28 hours (two cultures each).

50 mL of the cell culture was collected, and 1 g of the cells were added to and suspended to 5 mL of BugBuster protein extraction reagent and incubated at room temperature for 20 minutes while gently shaking.

After the insoluble fraction was removed by centrifugation at 15 Krpm at 4° C. for 20 minutes, the obtained supernatant was dialyzed using 20 mM sodium phosphate buffer/0.5 M NaCl/20 mM imidazole (pH7.0) at 4° C.

After dialysis, the precipitate was removed by centrifugation (at 15 Krpm at 4° C. for 20 minutes), and the supernatant was applied to an open column containing 1 mL Ni-NTA gel. After application, washing was performed with 10 ml of buffer A, and stepwise elution (5 mL each) was performed with (buffer A):(buffer B)=90.5:9.5 to (buffer A):(buffer B)=75:25.

The supernatant and non-adsorbed fractions were placed in a microdialyzer (EasySep) and dialyzed against 20 mM potassium phosphate buffer (pH 6.5) at 4° C.

In addition, the 9.5% and 25% eluates were placed in a 3.5-kDa cutoff dialysis membrane and dialyzed against 20 mM potassium phosphate buffer (pH6.5) at 4° C.

The compositions of the buffer A and buffer B used are as follows.

Buffer A: 20 mM sodium phosphate buffer/0.5 MNaCl/20 mM imidazole (pH 7.0)

Buffer B: 20 mM sodium phosphate buffer/0.5 M NaCl/500 mM imidazole (pH 7.0)

After dialysis, the 25% eluate was concentrated with a 10-kDa cutoff ultrafiltration membrane to obtain a purified sample.

A sample for SDS-PAGE was prepared by mixing the eluate (5 μL), loading buffer (5 μL), mercaptoethanol (1 μL) and H$_2$O (9 μL) and heating the mixture at 95° C. for 10 minutes, and 5 μL of the sample was applied.

2-2. Method of the Evaluation of Enzymatic Activity

The GDH enzyme activity of the obtained fusion protein was measured using 0.06 mM DCIP and 0.6 mM MPMS in 20 mM potassium phosphate buffer (pH 6.5). As a substrate, 40 mM glucose (final concentration) was used. The activity of the enzyme that oxidizes 1 μmol of glucose for 1 minute was defined as 1 unit.

2-3. Results and Discussion

After culture, the obtained transformants expressing BFU/b562 and the wet cells of the transformants expressing b562/BFU had a reddish color. After each of the wet cells was lysed, the red color of the lysed supernatant was very small, while the precipitate had a reddish color. In addition, the red color of the lysed supernatant was slightly strong in BFU/b562.

FIG. 3 illustrates the results of SDS-PAGE analysis. In SDS-PAGE, it could be confirmed that the fusion proteins (BFU/b562 and b562/BFU) were all expressed and produced as planned (a band around 75 kD). It was confirmed that BFU/b562 was partially cleaved (a band around 15 kD), the band was thick, indicating that the proportion of the cleavage was very small. In addition, in b562/BFU, the band of Bfu alone could hardly be seen, indicating that the cleavage of the protein hardly occurred.

Tables 1-1 and 1-2 below represent the results of measuring the production of each of BFU/b562 and b562/BFU and the activity of each enzyme.

The recovery rate of each fusion protein was 113.5% for BFU/b562 and 107.2% for b562/BFU, indicating that each fusion protein was almost all recovered.

In addition, the recovery of activity for the total activity was 96.4% for BFU/b562 and 72.5% for b562/BFU. Since the enzyme activity was low in some cases, it is suggested that adsorption or the like occurred during measurement or deactivation occurred in the purification step.

μg fusion protein/L) in 20 mM potassium phosphate buffer (pH 6.5) to a total volume of 200 μL, and after 0, 0.5, 2, 4, 6, 8, 10 and 16 minutes, spectral measurement was performed. In addition, a reducing agent (final concentration: 5 mM sodium dithionite) was added to the sample (0.9 μg fusion protein/L) to a final volume of 200 μL, and spectral measurement upon complete reduction was performed

3-2. Results

Figure 4:
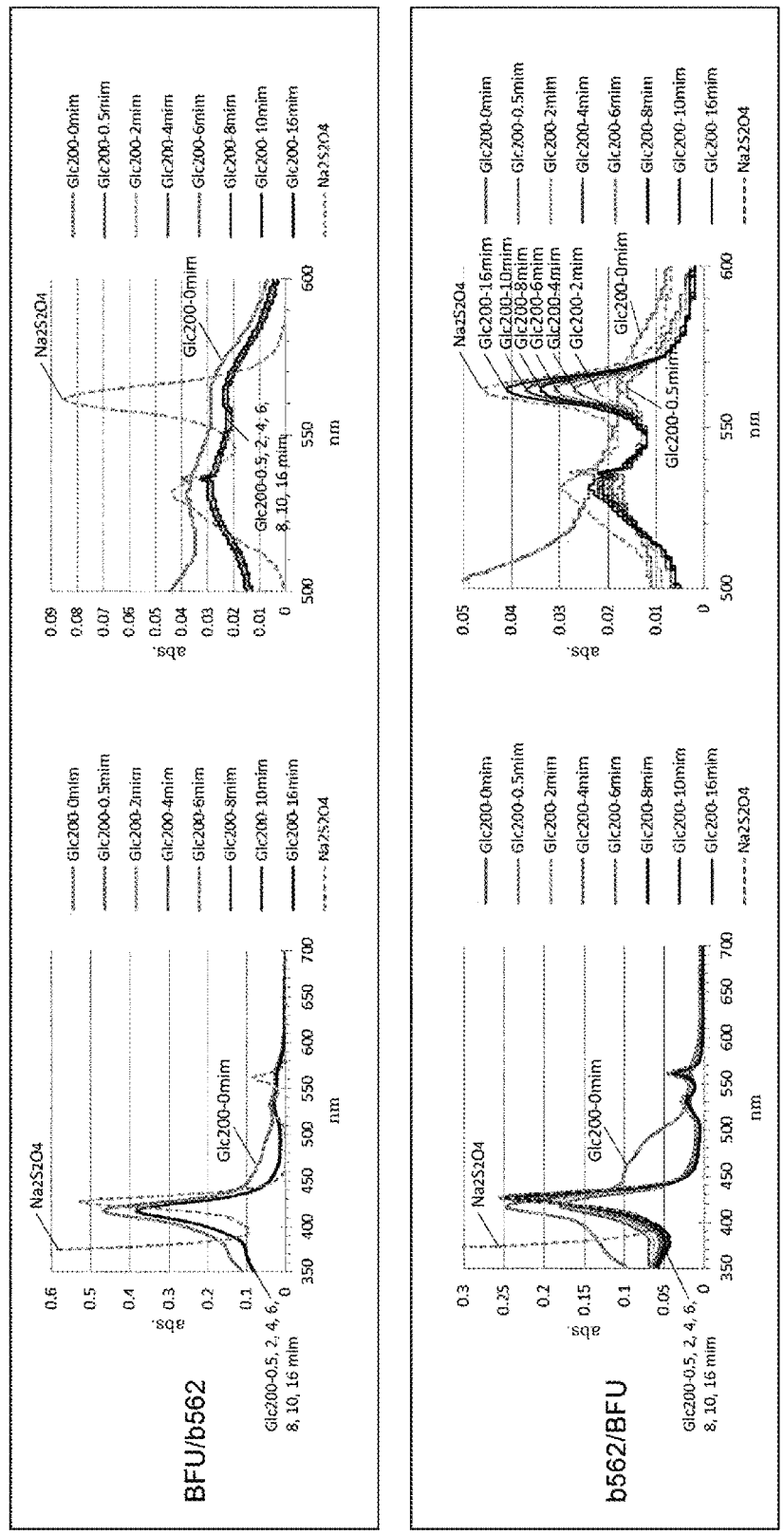
FIG. 4 illustrates the results of measuring the UV-VIS spectra of a fusion protein (BFU/b562) and a fusion protein at 350 to 700 nm. Top: BFU/b562, bottom: b562/BFU. In each of the top and the bottom, left figure: the results of measurement in the range of 350 to 700 nm, right figure: the results of measurement in the range of 500 to 600 nm.

FIG. 4 illustrates the results of measurement of the UV-VIS spectrum. It could be confirmed that the fusion proteins all exhibited a reduction peak by the addition of the reducing agent, and thus contained heme having a function.

However, for BFU/b562, the reduction peak of heme could not be found even when glucose was added (FIG. 4, top). This result indicates that, when the cytochrome molecule was linked to the C-terminus of the fungus-derived FADGDH, electron transfer from FAD to heme did not occur. That is, for this fusion protein, the cytochrome molecule having DET ability was not reduced by addition of glucose. That is, it has become clear that, in the previously reported configuration, DET ability cannot be imparted to the fungus-derived FADGDH.

In addition, for b562/BFU, the reduction peak of heme by the addition of glucose could be found (FIG. 4, bottom). Thus, it was shown that, when heme was linked to the N-terminus of the fungus-derived FADGDH, electron transfer from FAD to the heme became possible.

As described above, the DET ability could be imparted to the fungus-derived FADGDH by linking the cytochrome molecule to the N-terminus of the FADGDH protein.

TABLE 1-1

| Glc 40 mM PMS/DCIP | Amount (ml) | Protein (mg/ml) | Total protein (mg) | Protein yield (%) | | U/ml | Total U | | Total U % | U/mg | |
|---|---|---|---|---|---|---|---|---|---|---|---|
| BFU/b562 | 8.0 | 4.61 | 36.9 | 100 | — | 121.7 | 973.6 | 100 | — | 27.09 | 1.00 |
| Through | 11.0 | 3.24 | 35.7 | 96.7 | 96.7 | 21.0 | 231.1 | 23.7 | 23.7 | 6.58 | 0.24 |
| 9.5% | 5.0 | 0.90 | 4.5 | 12.2 | 16.8 | 118.4 | 592.2 | 60.8 | 72.7 | 134.95 | 4.98 |
| 25% | 5.0 | 0.33 | 1.7 | 4.6 | | 23.2 | 115.7 | 11.9 | | 70.42 | 2.60 |
| Conc 25% | 4.51 | 4.51 | 1.1 | — | — | 823.9 | 206.0 | — | — | 189.95 | — |

TABLE 1-2

| Glc 40 mM PMS/DCIP | Amount (ml) | Protein (mg/ml) | Total protein (mg) | Protein yield (%) | | U/ml | Total U | | Total U % | U/mg | |
|---|---|---|---|---|---|---|---|---|---|---|---|
| b562/BFU | 8.0 | 3.84 | 30.7 | 100 | — | 54.3 | 434.0 | 100 | — | 14.99 | 1.00 |
| Through | 11.0 | 2.75 | 30.3 | 98.7 | 98.7 | 4.1 | 44.9 | 10.3 | 10.3 | 1.60 | 0.11 |
| 9.5% | 5.0 | 0.44 | 2.2 | 7.2 | 8.5 | 49.0 | 244.8 | 56.4 | 52.2 | 118.18 | 7.89 |
| 25% | 5.0 | 0.07 | 0.4 | 1.3 | | 5.1 | 25.3 | 5.8 | | 71.87 | 4.79 |
| Conc 25% | 0.25 | 6.14 | 1.5 | — | — | 1100.3 | 275.1 | — | — | 184.61 | — |

(3) Measurement of UV-VIS Spectrum

3-1. Method

Measurement of the spectrum of reduced heme was performed according to a conventional known method. The 25% elution fraction concentrate of each fusion protein was diluted 5 times to obtain a sample, and the absorption spectrum at 350 to 700 nm was measured. That is, glucose (final concentration: 200 mM) was added to the sample (0.9

(4) Electrochemical Evaluation of DET Ability

4-1. Method

The DET ability of b562/BFU was evaluated by the following method.

A 4% mesoporous carbon dispersion (10 μL) prepared by mixing mesoporous carbon (manufactured by Toyo Carbon Co., Ltd.) with acetone was dried to obtain mesoporous carbon particles. The mesoporous carbon particles and 8 μL of b562/BFU (4.9 mg/ml) were added to 1 μL of 100 mM potassium phosphate buffer (pH 7.0) and incubated at 25° C. for 1 hour. 1 μL of 20% sucrose was added thereto to obtain ink, and 7 μL of the ink was dropped onto an Au electrode (7 mm²) and crosslinked (1 hour under a 25% glutaraldehyde atmosphere). The obtained material was blocked and washed with Tris buffer, and then stored in 100 mM potassium phosphate buffer (pH 7.0) until use.

Measurement was performed at 37° C. in 100 mM potassium phosphate buffer (pH 7.0) using an electrode immobilized with a b562/BFU-immobilized electrode as a working electrode, a platinum electrode as a counter electrode, and an Ag/AgCl electrode as a reference electrode. A voltage of +0.4 V vs. Ag/AgCl was applied, and the increase in the current value by the addition of glucose was measured.

4-2. Results

Figure 5:
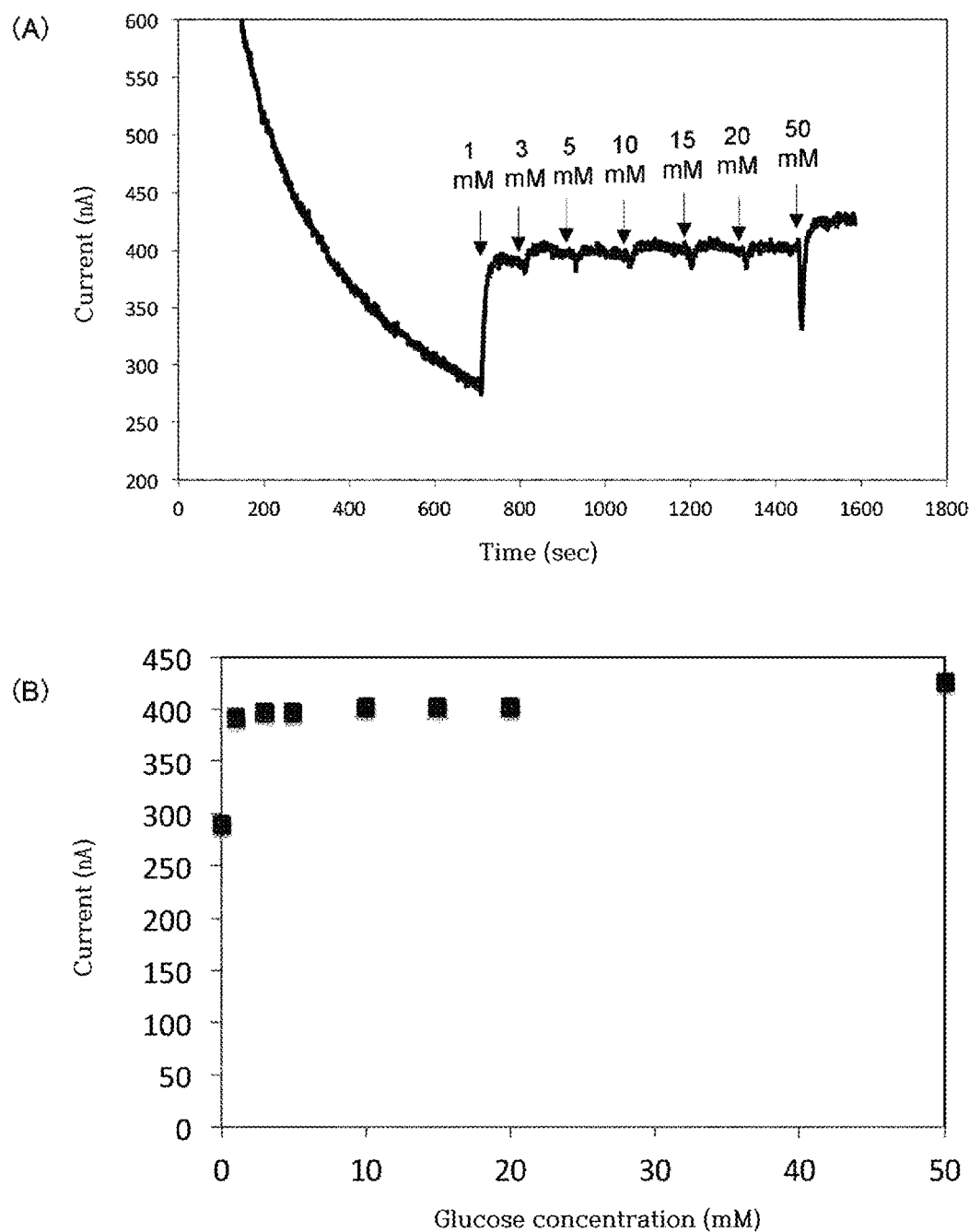
FIG. 5 depicts graphs illustrating the results of electrochemical measurement using an electrode having a fusion protein (b562/BFU) immobilized thereon.

FIG. 5 illustrates the response results of the b562/BFU-immobilized electrode. The rapid increase in the current value by the addition of 1 mM glucose was observed, indicating that b562/BFU had DET ability (FIG. 5(A)). In contrast, in the electrode fabricated in the same shape using the BFU alone, this response could not be seen.

These results clearly show that the DET ability could be imparted to the fungus-derived FADGDH by linking the cytochrome molecule to the N terminus.

Example 2: Fusion Protein Comprising Fungus-Derived FADGDH and Cytochrome Molecule from Cellobiose Dehydrogenase (I) Construction of Fusion Protein An examination of whether or not an enzyme having electron transfer ability could be constructed by linking the heme domain of fungal cellobiose dehydrogenase as a cytochrome molecule to the N-terminus of a fungus-derived FADGDH was made.

FIG. 6A illustrates the amino acid sequence of a fusion protein which is recombinantly produced based on a gene constructed by linking the cytochrome domain of cellobiose dehydrogenase from *Phanerochaete chrysosporium* (PcCDH heme) at the gene level to the N-terminus of a fungus-derived FADGDH in this Example. In addition, the "fungus-derived FADGDH" used in this Example is an FADGDH (AfGDH) from *Aspergillus flavus*.

It was aimed at constructing a desired fusion protein (PcCDH heme-AfGDH) by linking the cytochrome domain to the N-terminus of the FADGDH via the loop sequence of cellobiose dehydrogenase derived from *Phanerochaete chrysosporium* as a linker sequence. In addition, in this fusion protein, the cytochrome domain lacked the N-terminal signal sequence.

A fusion protein expression vector was constructed by inserting genes, which encode each fusion protein designed as described above, into the expression vector pPIC9 that causes homologous reconstitution on the genome. To the N-terminus of the gene encoding the cytochrome domain, the gene encoding the signal sequence of an α-factor derived from the expression vector was linked. Yeast (*Pichia pastoris*) was transformed with the obtained expression vector.

(II) Gene Expression

II-1. Method

Expression of the fusion protein in the transformants obtained by transformation with the expression vector was analyzed, and culture was performed using the transformants (sample No. 3 and No. 4) showing high activity. For culture, each transformant was inoculated into 3 mL BMGY medium (1% yeast extract, 2% peptone, 1.34% yeast nitrogen base (containing no amino acid), 0.002% biotin, 100 mM sodium phosphate buffer (pH 6.0), 1% glycerol) and cultured at 150 rpm at 30° C. for 12 hours. Thereafter, the cells were inoculated into 50 mL BMGY medium and additionally cultured at 30° C. at 150 rpm for 24 hours. After completion of culture, the cells were harvested (1500 g, 10 min, room temperature), suspended in BMMY medium (1% yeast extract, 2% peptone, 1.34% yeast nitrogen base (containing no amino acid), 0.002% biotin, 100 mM potassium phosphate buffer (pH 6.0), and induced in a 100-mL scale (at 30° C. at 190 rpm for 72 hours). For induction, 5% methanol was added every 24 hours to a final concentration of 0.5%.

After completion of induction, the cells were harvested, and the obtained supernatant was subjected to ammonium sulfate precipitation (60% and 80% saturation). At 80% saturation with ammonium sulfate, the precipitate was dissolved in 20 mM potassium sulfate buffer (pH 6.5), and the obtained solution was dialyzed against 20 mM potassium phosphate buffer (pH 6.5) (2 hours at 4° C. for the first time, 2 hours at 4° C. for the second time, and overnight at 4° C. for the third time). The solution after dialysis was used as a culture supernatant fraction. After dialysis, the solution was purified by anion exchange chromatography under the conditions of Resource Q column, Linear gradient 40CV 0-100 mM NaCl (20 mM potassium phosphate buffer (pH 6.5)).

After purification, the fraction was analyzed by SDS-PAGE, and the fraction including the target band was dialyzed against 20 mM potassium phosphate buffer (pH 6.5) (overnight at 4° C.) to obtain a purified enzyme.

The wet cells were lysed with a French press, centrifuged (at 13,000 g at 4° C. for 20 minutes), and then ultracentrifuged (at 108,000 g at 4° C. for 1 hour). The supernatant was dialyzed to obtain a water-soluble fraction. The obtained water-soluble fraction and culture supernatant fraction were subjected to SDS-PAGE analysis as described above.

II-2. Results and Discussion

FIG. 7 illustrates the results of SDS-PAGE analysis. Compared to the culture supernatant (OS) of non-transformed host cells (*P. pastoris*), in samples No. 3 and No. 4, a smeared band was observed around 100 to 120 kDa. The predicted molecular weight of the fusion protein (PcCDH heme-AfGDH) of this Example was about 83 kDa, and this result suggests that a band shift due to sugar chain modification occurred.

(III) Evaluation of Enzymatic Activity

III-1. Method

The GDH activity of the obtained fusion protein was evaluated using the following systems.

DCIP (0.06 mM (final concentration))/PMS (0.6 mM (final concentration)) system: for evaluation, 20 potassium phosphate buffer (pH 6.5) was used as a buffer, and glucose (5, 10, 20, 50, 100, and 200 mM (final concentrations)) was used as a substrate.

Ru ((w/v) 2% Ru (III))/MTT (1 mM MTT (final concentration)) system: for evaluation, 20 mM potassium phosphate buffer (pH 6.5) was used as a buffer, and glucose (20 and 200 mM (final concentrations)) was used as a substrate.

MTT (1 mM MTT (final concentration)) system: for evaluation, 20 mM potassium phosphate buffer (pH 6.5) was used as a buffer, and glucose (20 and 200 mM (final concentrations)) was used as a substrate.

For evaluation, the activity of the enzyme that oxidizes 1 μmol of glucose for 1 minute was defined as 1 unit.

III-2. Results

The $K_m$ and $V_{max}$ of the obtained PcCDH heme-AfGDH were calculated from the Lineweaver-Burk plot, and as a result, the $K_m$ was 53 mM and the $V_{max}$ was 250 U/mg. Compared to AfGDH produced recombinantly in E. coli ($K_m$=45.8 mM, and $V_{max}$=400 U/mg), it was confirmed that the $V_{max}$ was reduced to 63%. This is considered to be due to sugar chain modification or the linking of the cytochrome domain to the N-terminus.

In addition, almost no activity was observed in the Ru/MTT system (200 mM glucose: $2.0 \times 10^{-3}$ U/mg; 20 mM glucose: $3.2 \times 10^{-3}$ U/mg).

In addition, the MTT system showed an activity equal to about 1/1000 of the PMS/DCIP system, but showed a 10-fold activity compared to the Ru/MTT system. Furthermore, when Ru was added after the evaluation of the activity in the MTT system, the reaction greatly decreased.

These results suggest that Ru functions as an inhibitor and the efficiency of electron transfer from the FAD of AfGDH to the heme of cytochrome domain is low. Furthermore, when the substrate concentration in the MTT system was changed, the maximum activity could be obtained for 20 mM glucose, and when the substrate concentration was high, a decrease in the activity was observed. This occurs at a suggests that substrate inhibition concentration of 20 mM glucose or higher in the MTT system.

(IV) Measurement of UV-VIS Spectrum

IV-1. Method

Glucose (final concentration: 20 mM) was added to the obtained PcCDH heme-AfGDH in 20 mM potassium phosphate buffer (pH 6.5), and after 0, 1, 5, 10, 30, 60, 120 and 180 minutes, the absorption spectrum at 400 to 600 nm was measured.

IV-2. Results

FIG. 8 illustrates the results of measurement of the spectrum, and the absorption spectrum of the solet band (420 to 430 nm) derived from the heme was observed. In addition, after the addition of glucose, a shift of the peak to 432 nm over 0 to 180 minutes was observed. In addition, reduction peaks of the cytochrome domain were observed at 530 nm and 560 nm.

From these results, it was confirmed that electron transfer within the molecule of the fusion protein takes place FIG. 9 illustrates the spectral difference (the value of reduction by glucose addition—the value of oxidation) in the UV-VIS spectral measurement between before and after addition of glucose. The reduction peak of the cytochrome domain was clearly observed. From this, it was confirmed that, after glucose was added and oxidized and the FAD of AfGDH was reduced by the addition of glucose, electrons were transferred from the reduced FAD to the cytochrome domain and the cytochrome domain was reduced.

(V) Electrochemical Evaluation of DET Ability

V-1. Method 0.8 μL of a 2% (w/w) MWNT (MW-I, Meijo Nano Carbon Co., Ltd.) dispersion was applied once or twice onto the CE (4.8 mm²) of a carbon printed electrode (DEP chip) and dried. Furthermore, 1.0 μL of 10 mM 1-pyrenebutyric acid N-hydroxysuccinimide ester (PyNHS in DMF) was applied to the applied MWNT and dried. Thereafter, 3 μL of 5 mg/mL PcCDH heme-AfGDH in 20 mM potassium phosphate buffer (pH 7.5) was dropped onto the MWNT/PyNHS-applied chip and allowed to stand at 25° C. for 2 hours under high humidity, and then the enzyme solution on the chip was naturally dried. After drying, crosslinking was performed at 25° C. for 30 minutes under a glutaraldehyde atmosphere. The fabricated electrode chip was stored under low humidity (McDry: 1% RH) until use. For measurement, the electrode chip was washed with a 100 mM potassium phosphate buffer (pH 7.0) for 20 minutes, and then electrochemical measurement was performed.

The electrochemical measurement was performed in a batch cell (2.0 mL in 5 mL volume cell) at room temperature (25° C.±2° C.) using the PcCDH heme-AfGDH-immobilized electrode as a working electrode, a platinum electrode as a counter electrode, and an Ag/AgCl electrode (BAS RE-1 B) electrode as a reference electrode.

The CA measurement was performed at a stirring speed of 300 rpm in 100 mM potassium phosphate buffer (pH 6.0, 6.5 and 7.0). As for the calibration curve, a potential of +400 mV vs. Ag/AgCl was applied, and the response current was measured by adding a glucose solution, prepared in the buffer as that for the measurement solution, same sequentially at 0.1, 0.5, 1, 2.5, 5, 10, 20 and 50 mM in order. After the measurement, CA measurement was performed using the same chip in the measurement solution (50 mM glucose, 100 mM potassium phosphate buffer (pH 6.0)) at an applied potential of +400 mV.

V-2. Results

FIG. 10 illustrates the results of CA measurement in the measurement solution at pH 6.0, and a clear response by the addition of the substrate could be confirmed. When the enzyme concentration at the time of immobilization was low and the pH of the measurement solution was 6.5, almost no response was observed (FIGS. 10(A) and 10(B)). Furthermore, the measurement solution was replaced and the pH value was changed in the order of (1) pH 6, (2) pH 7, and (3) pH 6, and then the current value was measured, and as a result, no response was observed at pH 7 (FIG. 10(C)). From this, it was suggested that, even in the fusion with AflGDH, electron transfer to PcCDH heme is pH-dependent, and that the electron transfer occurs at a low pH.

As described above, the fungus-derived FADGDH having direct electron transfer ability could be obtained by linking the heme domain of fungal cellobiose dehydrogenase as a cytochrome molecule to the N-terminus of FADGDH. Furthermore, it was confirmed that the FADGDH may be used as an element for a glucose sensor having direct electron transfer ability, which does not require an electron mediator.

Example 3: Fusion Protein Comprising Fungus-Derived FADGDH Variant and Cytochrome Molecule from Cellobiose Dehydrogenase

(I) Construction of Fusion Protein

An examination of whether or not an enzyme having direct electron transfer ability could be constructed by linking the heme domain of fungal cellobiose dehydrogenase as a cytochrome molecule to the N-terminus of a fungus-derived FADGDH variant was made.

FIGS. 6B, 6C, 6D and 6E illustrate the amino acid sequences of fusion proteins which are each produced recombinantly based on a gene constructed by linking the cytochrome domain of cellobiose dehydrogenase from *Phanerochaete chrysosporium* at the gene level to the N-terminus of a fungus-derived FADGDH variant in this Example. In addition, the "fungus-derived FADGDH" used in this Example is an FADGDH (AfGDH) derived from *Aspergillus flavus*.

It was aimed at constructing a desired fusion protein (PcCDH heme-AfGDH variant) by linking the cytochrome domain to the N-terminus of the FADGDH variant via the loop sequence of cellobiose dehydrogenase derived from *Phanerochaete chrysosporium* as a linker sequence. In addition, this fusion protein lacks the N-terminal signal sequence of the cytochrome domain.

A fusion protein expression vector was constructed by inserting genes, which encode each variant fusion protein designed as described above, into the expression vector pPIC9 that causes homologous reconstitution on the genome. To the N-terminus of the gene encoding the cytochrome domain, the gene encoding the signal sequence of an α-factor derived from the expression vector was linked. Yeast (*Pichia pastoris*) was transformed with the obtained expression vector.

(II) Gene Expression

II-1. Method

Expression of the fusion protein in the transformants obtained by transformation with the expression vector was analyzed, and culture was performed using the transformants showing high activity. For culture, each transformant was inoculated into 3 mL BMGY medium (1% yeast extract, 2% peptone, 1.34% yeast nitrogen base (containing no amino acid), 0.002% biotin, 100 mM sodium phosphate buffer (pH 6.0), 1% glycerol) and cultured at 150 rpm at 30° C. for 12 hours. Thereafter, the cells were inoculated into 50 mL BMGY medium and additionally cultured at 30° C. at 150 rpm for 24 hours. After completion of culture, the cells were harvested (1500 g, 10 min, room temperature), suspended in BMMY medium (1% yeast extract, 2% peptone, 1.34% yeast nitrogen base (containing no amino acid), 0.002% biotin, 100 mM potassium phosphate buffer (pH 6.0)), and induced in a 100-mL scale (at 30° C. at 190 rpm for 72 hours). For induction, 5% methanol was added every 24 hours to a final concentration of 0.5%.

After completion of induction, the cells were harvested, and the obtained supernatant was subjected to ammonium sulfate precipitation (60% and 80% saturation). At 80% saturation with ammonium sulfate, the precipitate was dissolved in 20 mM potassium sulfate buffer (pH 6.5), and the obtained solution was dialyzed against 20 mM potassium phosphate buffer (pH 6.5) (2 hours at 4° C. for the first time, 2 hours at 4° C. for the second time, and overnight at 4° C. for the third time). The solution after dialysis was used as a culture supernatant fraction. After dialysis, the solution was purified by anion exchange chromatography under the conditions of Resource Q column, Linear gradient 40CV 0-100 mM NaCl (20 mM potassium phosphate buffer (pH 6.5)).

After purification, the fraction was analyzed by SDS-PAGE, and the fraction including the target band was dialyzed against 20 mM potassium phosphate buffer (pH 6.5) (overnight at 4° C.) to obtain a purified enzyme.

The wet cells were lysed with a French press, centrifuged (at 13,000 g at 4° C. for 20 minutes), and then ultracentrifuged (at 108,000 g at 4° C. for 1 hour). The supernatant was dialyzed to obtain a water-soluble fraction. The enzymatic activities of the obtained water-soluble fraction and culture supernatant fraction were measured.

(III) Evaluation of Enzymatic Activity

III-1. Method

The GDH activity of the obtained variant fusion protein was evaluated using the following systems.

DCIP (0.06 mM (final concentration))/PMS (0.6 mM (final concentration)) system: for evaluation, 20 mM potassium phosphate buffer (pH 6.5) was used as a buffer, and glucose (5, 10, 20, 50, 100 and 200 mM (final concentrations)) was used as a substrate.

Ru ((w/v) 2% Ru (III))/MTT (1 mM MTT (final concentration)) system: for evaluation, 20 mM potassium phosphate buffer (pH 6.5) was used as a buffer, and glucose (20 and 200 mM (final concentrations)) was used as a substrate.

MTT (1 mM MTT (final concentration)) system: for evaluation, 20 mM potassium phosphate buffer (pH 6.5) was used as a buffer, and glucose (20 and 200 mM (final concentrations)) was used as a substrate. For evaluation, the activity of the enzyme that oxidizes 1 μmol of glucose for 1 minute was defined as 1 unit.

III-2. Results

The enzymatic activities of the obtained PcCDH heme-AfGDH (variants) were measured. As a result, fusion enzymes of AfGDH variants, including Glu346Lys (E346K), Glu346Arg (E346R), Asn430Lys (N430K), Asn430Arg (N430R), Thr498Lys (T498K), Thr498Arg (T498R), Glu504Lys (E504K), and Glu504Arg (E504R), all achieved enzyme production equivalent to or higher than that of the wild-type enzyme (Table 2).

TABLE 2

|  | PMS/DCIP (U/L culture) | MTT (U/L culture) |  | PMS/DCIP (U/L culture) | MTT (U/L culture) |
| --- | --- | --- | --- | --- | --- |
| WT | 12576.7 | 2.2 |  |  |  |
| E346K | 13441.7 | 0.15 | E346R | 11693.3 | 0.1 |
| N430K | 17049.1 | 0.2 | N430R | 19699.4 | 0.4 |
| T498K | 12374.2 | 0.15 | T498R | 8914.1 | 0.1 |
| E504K | 13674.8 | 0.15 | E504R | 14429.5 | 0.35 |

Thus, as a representative of the variants at each position, Glu346Lys (E346K), Asn430Lys (N430K), Thr498Lys (T498K) and Glu504Lys (E504K), in which each residue was substituted with Lys, were purified by anion exchange chromatography and evaluated in detail.

The enzyme samples prepared as described above were subjected to SDS-PAGE analysis, and as a result, it was confirmed that these variant fusion enzymes all had the same molecular weight as that of the wild-type AfGDH, and were clearly recovered as fusion proteins (FIG. 11).

The $K_m$ and $V_{max}$ of the variant fusion enzymes were calculated from the Lineweaver-Burk plot, and as a result, it was observed that these variant enzymes all had higher activity than the fusion enzyme constructed based on the wild-type FADGDH.

(IV) Measurement of UV-VIS Spectrum

IV-1. Method

Glucose (final concentration: 20 mM) was added to the obtained PcCDH heme-AfGDH (variant) in 20 mM potassium phosphate buffer (pH 6.5), and after 0, 1, 5, 10, 30, 60, 120 and 180 minutes, the absorption spectrum at 400 to 600 nm was measured.

IV-2. Results

FIG. 12 illustrates the results of measurement of the spectrum, and the absorption spectrum of the solet band (420 to 430 nm) derived from the heme was observed. In addition, after the addition of glucose, a shift of the peak to 432 nm over 0 to 180 minutes was observed. In addition, reduction peaks of the cytochrome domain were observed at 530 nm and 560 nm.

From these results, it was confirmed that electron transfer within the molecule of the variant fusion protein takes place.

(V) Electrochemical Evaluation of DET Ability

V-1. Method 0.8 μL of a 2% (w/w) MWNT (MW-I, Meijo Nano Carbon Co., Ltd.) dispersion was applied onto the CE (4.8 mm$^2$) of a carbon printed electrode (DEP chip) and dried. Furthermore, 1.0 μL of 10 mM 1-pyrenebutyric acid N-hydroxysuccinimide ester (PyNHS in DMF) was applied to the applied MWNT and dried. Thereafter, 0.25 U of the wild-type fusion protein or 0.1 U of the variant fusion protein (Glu346Lys (E346K), Asn430Lys (N430K), Thr498Lys (T498K), or Glu504Lys (E504K)), prepared in 20 mM potassium phosphate buffer (pH 7.5), was dropped onto the MWNT/PyNHS-applied chip and allowed to stand at 25° C. for 2 hours under high humidity, and then the enzyme solution on the chip was naturally dried. The fabricated electrode chip was stored under low humidity (McDry: 1% RH) until use. For measurement, the electrode chip was washed with 100 mM potassium phosphate buffer (pH 7.0) for 20 minutes, and then electrochemical measurement was performed.

Electrochemical measurement was performed in a batch cell (2.0 mL in 5 mL volume cell) at room temperature (25° C.±2° C.) using the PcCDH heme-AfGDH (variant)-immobilized electrode as a working electrode, a platinum electrode as a counter electrode, and an Ag/AgCl electrode (BAS RE-1 B) electrode as a reference electrode.

CA measurement was performed at a stirring speed of 300 rpm in 100 mM potassium phosphate buffer (pH 6.0, 6.5 and 7.0). As for the calibration curve, a potential of +400 mV vs. Ag/AgCl was applied, and the response current was measured by adding a glucose solution, prepared in the same buffer as that for the measurement solution, sequentially at 0.1, 0.5, 1, 2.5, 5, 10, 20 and 50 mM in order. After the measurement, CA measurement was performed using the same chip in the measurement solution (50 mM glucose, 100 mM potassium phosphate buffer (pH 6.0)) at an applied potential of +400 mV.

V-2. Results

FIG. 13 illustrates the results of CA measurement in the measurement solution at pH 6.0, and a clear response by the addition of the substrate could be confirmed. The constructed fusion proteins, comprising each of the AfGDH variants (Glu346Lys (E346K), Asn430Lys (N430K), Thr498Lys (T498K), and Glu504Lys (E504K)), all exhibited direct electron transfer ability. In addition, the variant fusion proteins, including Glu346Lys (E346K), Asn430Lys (N430K), Thr498Lys (T498K) and Glu504Lys (E504K), exhibited the response based on direct electron transfer at a higher current density than the fusion protein comprising the wild-type AfGDH. From this, it was suggested that these variant fusion proteins had improved direct electron transfer ability.

As described above, the FADGDH variant fusion protein having improved direct electron transfer ability compared to the wild-type protein could be obtained by linking the heme domain of fungal cellobiose dehydrogenase as a cytochrome molecule to the N-terminus of each of the FADGDH variants (Glu346Lys (E346K), Asn430Lys (N430K), Thr498Lys (T498K), and Glu504Lys (E504K)). In addition, it was confirmed that this FADGDH variant fusion protein may be used an element for a glucose sensor having direct electron transfer ability, which does not require an electron mediator.

The invention claimed is:

1. A fusion protein comprising: a variant of fungus-derived flavin adenine dinucleotide glucose dehydrogenase (FADGDH); and a cytochrome molecule linked to the N-terminus of the variant,
    wherein the variant comprises an amino acid sequence having one mutation selected from the group consisting of Glu346Lys, Asn430Lys, Asn430Arg, Thr498Lys, Glu504Lys, and Glu504Arg in the amino acid sequence of SEQ ID No: 4.

2. The fusion protein of claim 1, wherein the cytochrome molecule is a cytochrome domain of cellobiose dehydrogenase.

3. The fusion protein of claim 1, wherein the cytochrome molecule is (1) a cytochrome molecule derived from *E. coli* or (2) a cytochrome domain of oxidoreductase.

4. The fusion protein of claim 1, wherein the cytochrome molecule is cytochrome b.

5. The fusion protein of claim 1, wherein the fusion protein comprises an amino acid sequence of SEQ ID NO: 14, 16, 17, 18, 20, or 21.

6. A gene encoding the fusion protein set forth in claim 1.

7. A vector comprising the gene set forth in claim 6.

8. A transformant comprising the gene set forth in claim 6.

9. A transformant in which the gene set forth in claim 6 is integrated into the main chromosome of the transformant.

10. An enzyme electrode comprising the fusion protein set forth in claim 1 attached thereto.

11. A method for measuring glucose concentration in a sample, the method comprising:
    bringing the sample into contact with the enzyme electrode set forth in claim 10; and measuring electrons generated by oxidation of glucose.

12. A glucose sensor comprising the enzyme electrode set forth in claim 10 as a working electrode.

* * * * *